United States Patent [19]
Moriyama

[11] Patent Number: 5,885,208
[45] Date of Patent: Mar. 23, 1999

[54] ENDOSCOPE SYSTEM

[75] Inventor: Hiroki Moriyama, Yokohama, Japan

[73] Assignee: Olympus Optical Co., Ltd., Tokyo, Japan

[21] Appl. No.: 997,354

[22] Filed: Dec. 23, 1997

[30] Foreign Application Priority Data

| Dec. 24, 1996 | [JP] | Japan | 8-344051 |
| Jan. 7, 1997 | [JP] | Japan | 9-000803 |
| May 7, 1997 | [JP] | Japan | 9-116936 |
| May 20, 1997 | [JP] | Japan | 9-129981 |
| Jul. 24, 1997 | [JP] | Japan | 9-198515 |

[51] Int. Cl.$^6$ .................................................. A61B 1/005
[52] U.S. Cl. ........................................ 600/144; 600/146
[58] Field of Search .................................. 600/139, 144, 600/146, 149, 113

[56] References Cited

U.S. PATENT DOCUMENTS

| 3,948,251 | 4/1976 | Hosono | 600/144 |
| 4,890,602 | 1/1990 | Hake | 600/144 |
| 4,919,112 | 4/1990 | Siegmund | 600/146 |
| 4,977,887 | 12/1990 | Gouda . | |
| 5,168,864 | 12/1992 | Shockey | 600/144 |
| 5,179,935 | 1/1993 | Miyagi | 600/144 |
| 5,386,816 | 2/1995 | Inoue et al. | 600/149 |
| 5,520,272 | 5/1996 | Chikama | 600/146 |
| 5,676,635 | 10/1997 | Levin | 600/144 |

FOREIGN PATENT DOCUMENTS

| 3-43802 | 4/1991 | Japan . |
| 5-91971 | 4/1993 | Japan . |

*Primary Examiner*—Paul J. Hirsch
*Attorney, Agent, or Firm*—Louis Weinstein

[57] ABSTRACT

An endoscope system has a first endoscope in which a hardness variation mechanism for use in adjusting the hardness level of a soft part of an insertion unit is incorporated in the soft part, and at least one second endoscope having a soft part. A range of levels of the adjustable hardness of the soft part of the first endoscope includes the hardness level of the soft part of the second endoscope. Another endoscope system has a first endoscope in which a hardness variation mechanism for use in adjusting the hardness level of a soft part of an insertion unit is incorporated in the soft part, and at least one second endoscope usable for examination of the same region as the first endoscope and having a soft part. A range of levels of the adjustable hardness of the soft part of the first endoscope includes the hardness level of the soft part of the second endoscope.

43 Claims, 33 Drawing Sheets

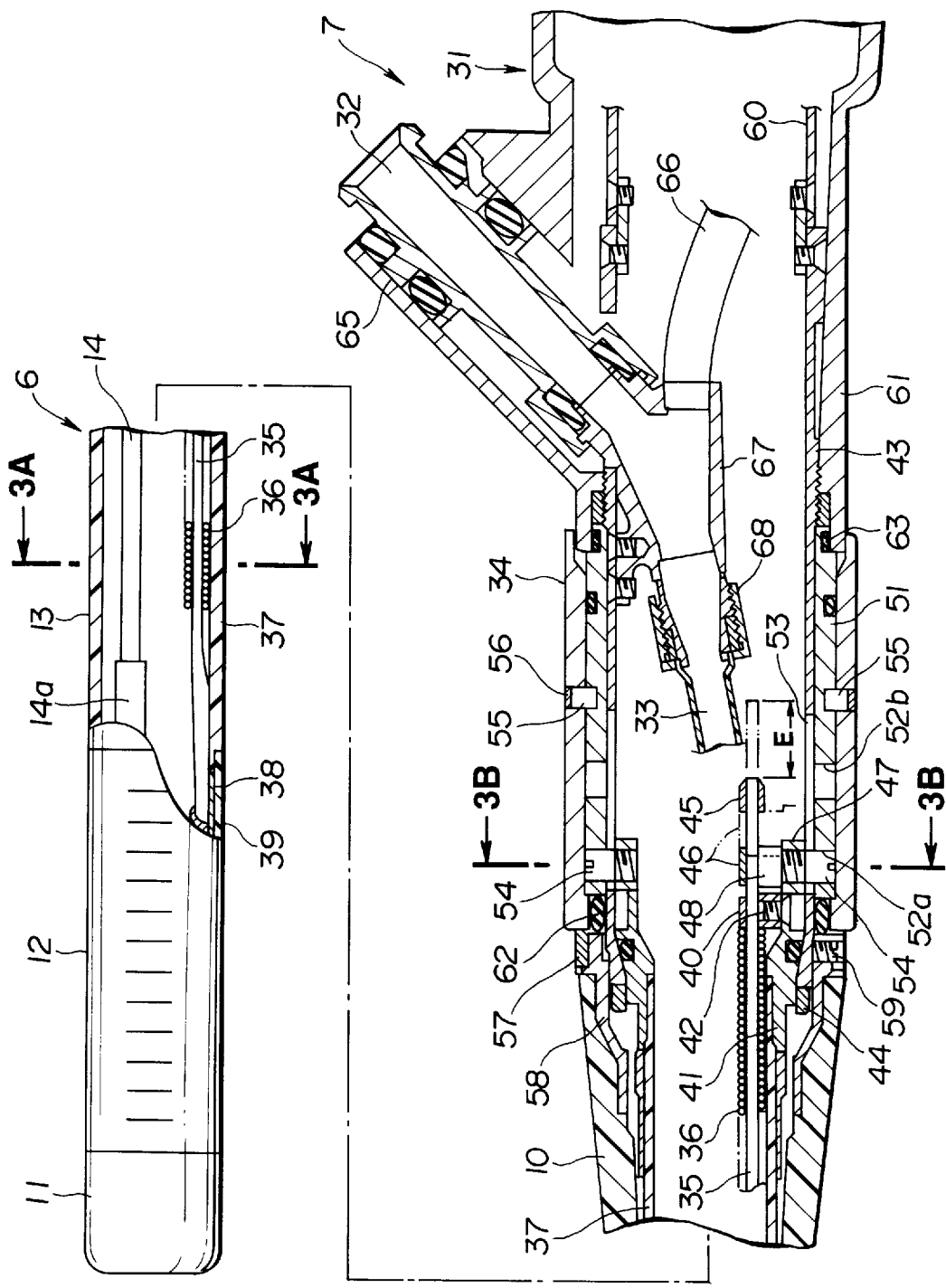

ENDOSCOPE SYSTEM

BACKGROUND OF THE INVENTION

1. Field of the Invention

The present invention relates to an endoscope system having an endoscope in which a hardness variation mechanism enabling adjustment of the hardness level of an elongated flexible insertion unit is incorporated.

2. Description of the Related Art

In recent years, an endoscope whose elongated insertion unit having flexibility is inserted into a region to be examined in a body cavity through the mouth or anus in order to observe the region to be examined in the body cavity without resection, or if necessary, to carry out a therapeutic procedure using a treatment appliance has been adopted widely.

The insertion unit of the endoscope has a flexible soft part so that the insertion unit can be passed through even a tortuous path. However, since the soft part has flexibility, a manipulation made proximally to the insertion unit is hardly conveyed to the distal part. The position or orientation of the distal side of the insertion unit cannot be determined as an operator intends. There is a problem that it is difficult to insert the distal part of the insertion unit smoothly into a region to be examined.

In an effort to cope with the above problem, for example, Japanese Unexamined Utility Model Publication No. 3-43802 has disclosed an endoscope in which: a coil pipe and wire constituting a hardness variation mechanism serving as a hardness varying means are incorporated in an insertion unit; and when an operator who conducts an endoscopic examination carries out a simple manipulation, if necessary, so as to adjust the degree of flexibility of the insertion unit properly, it becomes easier to insert the insertion unit into a tortuous path.

However, when the distal part of the hardness variation mechanism is located in, for example, the proximal side of a soft part composed of a distal side having high flexibility and the proximal side whose hardness level is set to a rather high level, the hardness variation mechanism works effectively in further hardening the proximal side, but fails to help adjust the hardness of the highly flexible distal side. The distal side therefore remains highly flexible. For inserting the endoscope into the rectum, sigmoid colon, descending colon, transverse colon, and ascending colon in that order through the anus for observation, an operator's manipulations made proximally are not fully conveyed to the distal part. Satisfactory obedience cannot therefore be expected. This poses a problem that it is difficult to insert the endoscope smoothly to a region to be examined.

Moreover, when the distal part of a hardness variation mechanism is located substantially at the same position as a hardness variation point of a soft part at which the hardness level of the soft part varies, if the hardness variation mechanism is hardened, an area of the soft part behind the hardness variation point gets rapidly harder while the distal side remains soft. The soft part does not therefore bend in a smooth form but bends near the hardness variation point to lose the insertional smoothness. When the soft part is bent, there is a fear that the contents of the soft part, that is, light guide fibers and channels lying through the soft part may be damaged.

In short, no mention has been made of where the distal part of the hardness variation mechanism should be located in the soft part or the practical position of the distal part.

Furthermore, in an endoscope in which the variable hardness level of a soft part of an insertion unit is adjustable, to what extent a range of levels of the variable hardness should be set has not been discussed at all.

In general, as far as a bar-like member is concerned, the harder it is, the more readily it is plastically deformed due even to a small bend. Even when a flexible variation member is hardened, the harder the member is, the more readily it buckles due to a small bend. When the coil-like flexible variation member is hardened, not only if an insertion unit is bent fiercely abruptly but also if the insertion unit is bent by a normal manipulation, the coil-like flexible variation member may be buckled depending on a hardness level present at the time of bend.

Moreover, in the case of an endoscope whose insertion unit has flexibility, the hardness level of a soft part of the insertion unit is not produced by setting the hardness level to a certain value. Assuming that a certain endoscope is regarded as a reference, when a hardness variation mechanism is added to another endoscope, generally speaking, the addition of the hardness variation mechanism to an insertion unit causes the diameter of the insertion unit to get larger or the filling factor of the contents of the insertion unit to increase. The resultant hardness level of the endoscope becomes higher than the hardness level of the endoscope used as a reference. Furthermore, the hardness variation mechanism itself exhibits a certain hardness level by nature even when it is softened most. Even from this viewpoint, the resultant hardness level gets higher than that of the reference endoscope. In other words, an endoscope having the hardness of a soft part thereof made adjustable is harder than the reference endoscope even when it is softened. With the addition of the hardness variation mechanism, the hardness level of the soft part gets even higher.

In an endoscope system having a plurality of endoscopes, when an operator uses an endoscope with a hardness adjustment function and an endoscope without the hardness adjustment function, since there is a difference in hardness level of a soft part between the endoscopes with and without the hardness adjustment function, the endoscopes lose compatibility. Since the endoscopes have no compatibility because of a difference in hardness level, an operator has a strong sense of incompatibility. Until the operator gets accustomed to the usage of the endoscope having the hardness adjustment function and exhibiting a different hardness level, the maneuverability of the endoscope deteriorates.

Furthermore, among operators using endoscope systems, of whatever types endoscopes are; a type to be used through the mouth, a type to be used through the anus, or any other types having different specifications, user-friendly endoscopes are highly demanded. Talking of, especially, endoscopes used as components of an endoscope system, there is a demand for endoscopes capable of being inserted into a region to be examined in a body cavity through the mouth or anus while giving an operator nearly the same feeling of insertion.

OBJECTS AND SUMMARY OF THE INVENTION

An object of the present invention is to provide an endoscope system in which a plurality of types of endoscopes being designed to be used as components of a system and having different specifications can be routed to a region to be examined in a body cavity while giving an operator nearly the same feeling of insertion.

Another object of the present invention is to provide an endoscope system in which a greatest possible effort is made so that it will not take place that when the same region to be examined is an object of examination, an endoscope with a hardness variation mechanism and an endoscope without it give an operator a sense of incompatibility in terms of insertional smoothness.

Another object of the present invention is to provide an endoscope system having an endoscope designed to convey proximally-made manipulations to a distal part by making the most of the capability of a hardness variation mechanism and to thus offer excellent obedience while putting emphasis on the softness of a soft part of an insertion unit.

Yet another object of the present invention is to provide an endoscope system having an endoscope of which insertion unit has a soft part capable of bending in a smooth form, of which insertional smoothness is excellent, and in which a hardness variation mechanism will not be damaged even in a use situation in which the insertion unit is bent to the greatest extent while the contents of the insertion unit are not damaged.

Still another object of the present invention is to provide an endoscope system having an endoscope in which an insertion unit can exhibit excellent insertional smoothness even when hardened using a hardness variation mechanism when the endoscope system is used to examine a region having a sharply bent part.

Briefly, an endoscope system in accordance with the present invention comprises a first endoscope in which a hardness variation mechanism for use in adjusting the hardness level of a soft part of an insertion unit is incorporated in the soft part, and at least one second endoscope having a soft part. The hardness level of the soft part of the second endoscope falls within a range of levels of the adjustable hardness of the soft part of the first endoscope.

BRIEF DESCRIPTION OF THE DRAWINGS

FIGS. 1 to 6 are diagrams for explaining the first embodiment of the present invention;

FIG. 1 is an explanatory diagram showing the schematic configuration of an endoscope system;

FIG. 2 is a sectional view of a major portion showing the more practical structure of a first endoscope;

FIG. 5 is a diagram expressing the characteristic balances in hardness of the first endoscope and second endoscope included in the endoscope system in relation to lengths from the tips of the endoscopes;

FIG. 6A is a diagram showing a state in which the distal part of the endoscope is routed to a region near the splenic curvature;

FIG. 6B is a diagram showing a state in which the tortuous part of the sigmoid colon is collapsed to be contracted and the sigmoid colon is thus substantially straightened;

FIG. 6C is a diagram showing a state in which the endoscope is inserted into the deep region in the large intestine;

FIGS. 8 to 9B are diagrams for explaining the third embodiment of the present invention;

FIG. 8 is a diagram expressing the characteristic balances in hardness of endoscopes included in the endoscope system;

FIG. 9B is an explanatory diagram showing another example of the hardness adjustment coil in the first embodiment;

FIG. 10 is an explanatory diagram showing the schematic configuration of an endoscope system;

FIG. 11 is a diagram expressing the characteristic balances in hardness of endoscopes included in the endoscope system;

FIG. 13 is a diagram showing the structure of an annulus ring substituted for a coil;

FIG. 14 is a diagram for explaining the structure of the hardness adjustment mechanism;

FIGS. 16 to 18 are diagrams for explaining the relationship between the position of the distal part of a coil included in a hardness variation mechanism in a soft part and insertion smoothness;

FIG. 16 is a diagram for explaining the operation of an endoscope;

FIG. 18 is an enlarged diagram showing a state in which the endoscope shown in FIG. 6B is inserted into the large intestine;

FIGS. 19 to 25D are explanatory diagrams showing an example of the structure of an endoscope having a hardness adjustment mechanism employed in an endoscope system in accordance with the present invention;

FIG. 19 is a diagram for explaining the schematic structure of an electronic endoscope;

FIG. 20 is a 20—20 sectional view of the electronic endoscope shown in FIG. 19;

FIG. 21 is a diagram showing a model for explaining the position of a coil pipe in a soft part;

FIG. 22 is a 22—22 sectional view of the soft part shown in FIG. 21;

FIG. 23 is a diagram expressing the characteristic balance in hardness of an endoscope having a soft part that includes a variable hardness point while showing the relationship between distances from the tip of the soft part and hardness levels;

FIG. 24 is a diagram expressing the characteristic balance in hardness of an endoscope having a soft part that includes a hardness variation area while showing the relationship between distances from the tip of the soft part and hardness levels;

FIGS. 25A to 25D are diagrams showing inserted states in which an endoscope is inserted through the anus;

FIG. 25A is a diagram showing a state in which the endoscope is inserted through the anus, passed through the rectum, and routed to the sigmoid colon;

FIG. 25B is a diagram showing a state in which the distal part of the endoscope is routed to a region near the splenic curvature;

FIG. 25C is a diagram showing a state in which the large intestine is collapsed to be contracted and thus substantially straightened and the endoscope is inserted into a deep region in the large intestine;

FIG. 25D is a diagram showing a state in which a first soft part of the endoscope is thrust forward in line with the shapes of the transverse colon and hepatic curvature and thus inserted into a deep region in the large intestine;

FIGS. 26 to 28C are explanatory diagrams showing another example of an endoscope having a hardness adjustment mechanism employed in an endoscope system in accordance with the present invention;

FIG. 26 is a diagram expressing the characteristic balance in hardness of an endoscope having a soft part that includes a variable hardness point while showing the relationship between distances from the tip of the soft part and hardness levels;

FIG. 27 is a diagram expressing the characteristic balance in hardness of an endoscope having a soft part that includes a variable hardness area while showing the relationship between distances from the tip of the soft part and hardness levels;

FIGS. 28A to 28C are diagrams showing inserted states in which an endoscope is inserted through the anus;

FIG. 28A is a diagram showing a state in which the endoscope is inserted through the anus, passed through the rectum, and routed to the sigmoid colon;

FIG. 28B is a diagram showing a state in which the distal part of the endoscope is routed to a region near the splenic curvature;

FIG. 28C is a diagram showing a state in which the large intestine is collapsed to be contracted and thus substantially straightened and the endoscope is inserted into a deep region in the large intestine;

FIG. 29 is a diagram expressing the characteristic balance in hardness of an endoscope having a soft part that includes a plurality of variable hardness areas while showing the relationship between distances from the tip of the soft part and hardness levels;

FIG. 30 is a diagram expressing the characteristic balance in hardness of an endoscope having a soft part whose variable hardness area has a large length while showing the relationship between distances from the tip of the soft part and hardness levels;

FIGS. 35 to 42 are explanatory diagrams showing a structure in which a hardness variation mechanism can exert the capability thereof even in a use situation in which the insertion unit of an endoscope having the hardness adjustment mechanism and employed in an endoscope system in accordance with the present invention is bent with a given minimum radius of curvature, and the contents of the endoscope will not be damaged;

FIG. 35 is a diagram for explaining a hardness adjustment mechanism incorporated in an operation unit of an endoscope;

FIG. 36 is a sectional view of the portion of the endoscope on a 36—36 plane shown in FIG. 35;

FIG. 39 is a diagram for explaining a locked state in which a coil and wire constituting the hardness adjustment mechanism are locked;

FIG. 40 is a diagram for explaining a hardness variation range or a range of levels of the variable hardness of a soft part of an insertion unit which is attained when the soft part is hardened using a coil included in a hardness adjustment member by rotating a hardness adjustment knob;

FIG. 41 is a diagram for explaining a use scene in which the endoscope is inserted into the large intestine of a patient;

FIG. 42 is a diagram showing a state in which the coil is buckled due to a small bend;

DESCRIPTION OF THE PREFERRED EMBODIMENTS

Referring to FIGS. 1 to 6, the first embodiment of the present invention will be described.

Figure 1:
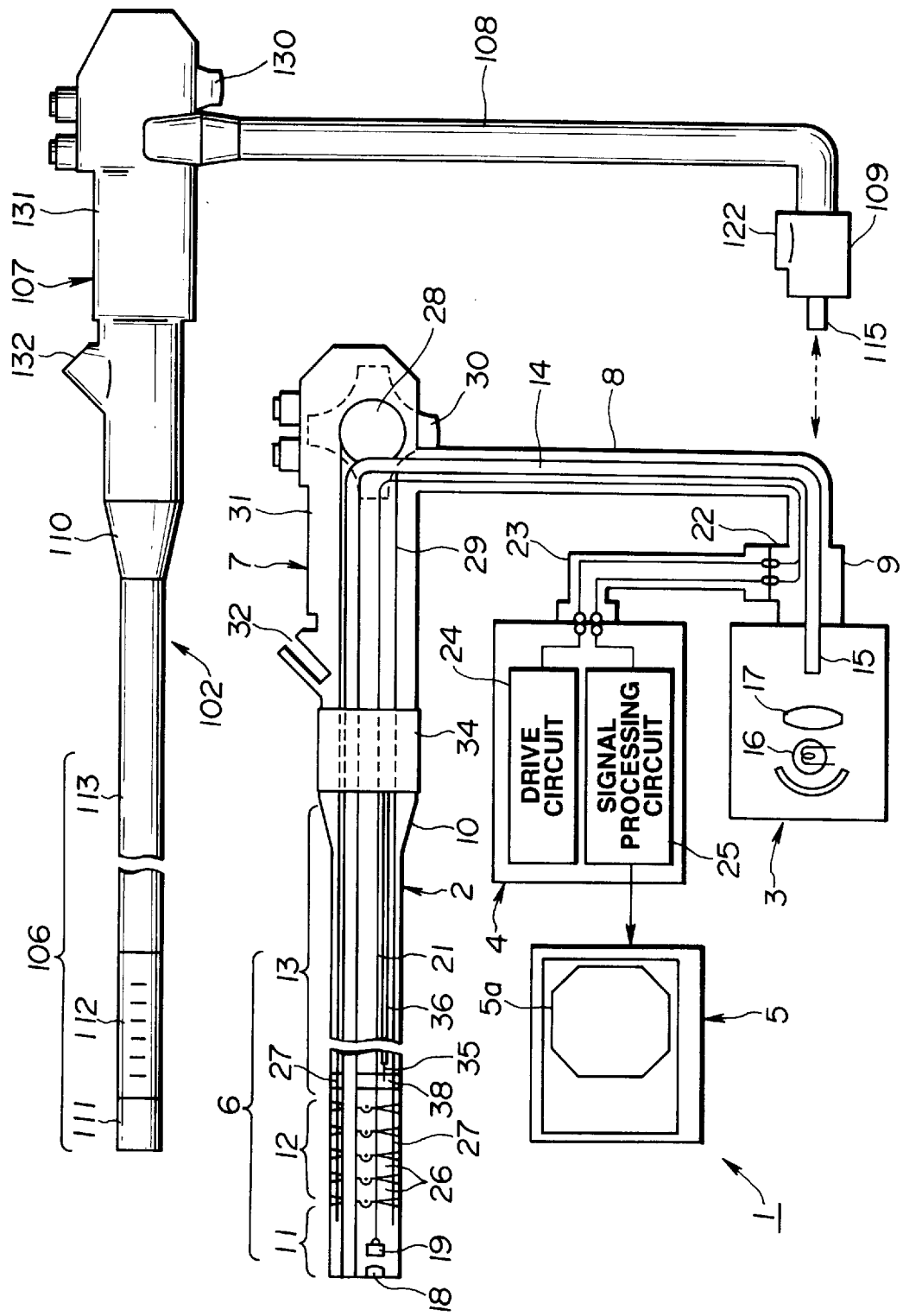

As shown in FIG. 1, an endoscope system 1 of this embodiment comprises a first endoscope 2 of an electronic type having an insertion unit 6 that is elongated and has flexibility, a second endoscope 102, a light source apparatus 3, a signal processing apparatus 4, and a color monitor 5.

The first endoscope 2 includes the insertion unit 6, an operation unit 7, and a universal cord 8. A connector 9 that is freely attachable or detachable to or from the light source apparatus 3 is attached to the tip of the extending universal cord 8. The proximal end of the insertion unit 6 is joined with the operation unit 7. An anti-bending member 10 is formed at the joint end.

The insertion unit 6 is formed by concatenating a distal part 11, bending portion 12, and a soft part 13 in that order from the distal side. Light guides 14 over which illumination light propagates and other contents extend through the insertion unit. The light guides 14 extend through the insertion unit 6, operation unit 7, and universal cord 8 and extends from the distal part 11 to a light guide connector 15 in the connector 9.

An imaging unit 20 composed of an objective lens 18 and an imaging device 19 such as a charge-coupled device is incorporated in the distal part 11 of the insertion unit 6. A signal cable 21 is linked to the imaging device 19 of the imaging unit 20. The signal cable 21 extends through the insertion unit 6, operation unit 7, and universal cord 8 and is linked to a connector 22 for electrical coupling included in the connector 9. An external cable 23 leading to the signal processing apparatus 4 is linked to the electrical-coupling connector 22.

A drive circuit 24 and signal processing circuit 25 are incorporated in the signal processing apparatus 4. The drive circuit 24 drives the imaging unit 20 over the external cable 23 and signal cable 21, and the signal processing circuit 25 processes an imaging signal sent from the imaging unit over the external cable 23 and signal cable 21, produces a video signal, and outputs the video signal to the color monitor 5.

The bending portion 12 of the insertion unit 6 is formed by concatenating a plurality of bending pieces 26 arranged in the longitudinal direction of the insertion unit. The bending pieces 26 have adjoining ends thereof fixed mutually, thus allowing the bending portion 12 to bend as a whole. The tips of pairs of bending wires 27 located right and left, and up and down are attached to a bending piece 26 located at the distal end of the bending portion 12. The backs of the bending wires 27 are linked to a towage wire 29 wound about a sprocket 28. By rotating the sprocket 28 using the bending knob 30, the bending wires 27 are thrust or pulled to tow the bending portion 12. This causes the bending portion 12 to bend as a whole in a direction in which the bending portion is towed.

A treatment appliance insertion port 32 is formed in a grip portion 31 of the operation unit 7. The treatment appliance insertion port 32 communicates with a treatment appliance passage channel 33 in the insertion unit 6. The treatment appliance passage channel 33 opens onto the distal part 11 of the insertion unit 6.

In the first endoscope 2, the flexibility (hereinafter expressed using the term "a hardness level") of the soft part 13 of the insertion unit 6 is adjustable. A hardness adjustment mechanism for use in adjusting the hardness level of the soft part 13 will be described.

In the first endoscope 2, a cylindrical hardness level adjustment knob (which hereinafter may be abbreviated as an adjustment knob) 34 is formed as a manipulation member to be manipulated for adjusting a hardness level at the front end of the operation unit 7 adjoining the anti-bending member 10 in such a way that the adjustment knob can be rotated.

By rotating the adjustment knob 34, the hardness level of the soft part 13 can be varied using a hardness variation wire 35 (which hereinafter may be abbreviated as a wire) included in a hardness variation mechanism and an elongated sheath, for example, a hardness variation coil 36 (which hereinafter may be abbreviated as a coil), which are located in the soft part 13.

As shown in FIG. 2, the wire 35 and coil 36 are located in a soft tube 37 serving as an armor that outlines the soft part 13 of the insertion unit 6 of the first endoscope 2. The coil 36 is formed with a single wire or a plurality of wires that are wound densely. The wire 35 is passed through the coil 36. The wire 35 is a single wire or strand and applies a force exerted by manipulating the adjustment knob 34 as a compressing force to the coil 36.

The back end of the bending portion 12 and the front end of the soft part 13 are linked by a hard linking tube 38. The linking tube 38 is fixed to the bending piece 26 located at the extreme back end of the bending portion 12. The bending piece 26 having the linking tube 38 is covered with an armor 39 having elasticity, such as, a rubber tube. The bending piece 26 at the extreme back end may be designed to have the capability of the linking tube 38.

The tip of the wire 35 jutting out of the tip of the coil 36 is fixed firmly to the linking tube 38 by performing brazing or the like. The distal part of the coil 36 is fixed firmly to the wire 35 passed through the coil at an intermediate position slightly behind the tip of the wire 35 by performing brazing or the like.

The proximal end of the coil 36 abuts on a coil stopper 40 located in the front part of the operation unit 7 and is secured at that position by performing brazing or soldering or using an adhesive. Thus, the movement of the coil behind the position or the rotation thereof is restricted i.e. prevented. By contrast, the wire 35 passed through the coil 36 passes through a bore in the coil stopper 40 and extends behind i.e. to the right of the coil stopper. The wire 35 is placed so that the wire can slide inside the coil 36 and thus move freely back and forth relative to the coil 36. Incidentally, the coil 36 is attached in a state in which it will not rotate largely.

The coil stopper 40 is fixed to a back base 41, by which the back end of the soft tube 37 is linked to the operation unit 7, using a screw 42. The back base 41 is fastened near the front end of a cylindrical tube 43 placed on the outer circumference of the back base using a screw 42 and nut 44. A sword guard-like wire stopper 45 is fixed firmly to the proximal end of the wire 35, that is, the back end thereof.

A towage member 46 movable back and forth is interposed between the coil stopper 40 and wire stopper 45. The towage member 46 has a groove 48 (or a bore), which allows the wire 35 to pass through the groove 48, and is fixed to a tubular movable ring 47 placed coaxially in the grip portion 31. In other words, as shown in FIG. 3B, the towage member 46 having the groove 48, which is formed by boring the towage member from the outer circumference thereof to the center thereof and through which the wire 35 is passed, is fixed to the inner circumferential surface of the tubular movable ring 47 by means of a screw 49.

The movable ring 47 is movable in the distal or proximal direction while sliding in the longitudinal direction of the insertion unit over the inner circumferential surface of the cylindrical tube 43 locked in the grip portion 31. When the towage member 46 moves backward with the movement of the movable ring 47, the towage member 46 abuts on the wire stopper 45 as indicated with an alternate long and two short dashes line in FIG. 2. When the towage member 46 is moved further backward, the wire stopper 45 is moved further backward.

In a state in which the wire stopper 45 is not moved backward, the coil 36 that is restrained from moving backward by means of the coil stopper 40 is most highly flexible, that is, is softened so that the soft part 13 can be bent most readily and exhibit a low hardness level.

By contrast, when the wire stopper 45 is moved backward, the back end of the wire 35 moves backward at the same time. The stationary coil stopper 40 exerts a compressing force that thrusts the coil 36 relatively forward. In other words, when a force moving the back end of the wire 35 backward is applied, a compressing force is applied to the coil 36. With the compressing force, the coil 36 having elasticity becomes less flexible, that is, gets hardened so that the soft part can exhibit a high hardness level hindering the coil from being bent smoothly, or more accurately, exhibit hardness that is high enough to resist bending. In this case, the hardness level of the soft part 13 can be varied by changing the magnitude of compressing force to be applied to the coil 36 according to the magnitude of backward movement of the towage member 46.

Next, a mechanism for moving the wire stopper 45 will be described.

The cylindrical tube 43 is covered with a cam cylinder 51. Two cam grooves 52a and 52b are formed spirally in the cylindrical part of the cam cylinder 51 overlying the cylindrical tube 42 with a phase difference of 180° between them. In other words, the two cam grooves 52a and 52b are mutually opposed and symmetrical. Two elongated holes 53 that are mutually parallel are bored in the longitudinal direction of the cylindrical tube 43. The movable ring 47 has two pins 54 fixed with screws. The pins 54 move together with the movable ring 47. The pins 54 are fitted into associated elongated holes 53 in the cylindrical tube 43 and engaged with the cam grooves 52a and 52b in the cam cylinder 51. The elongated holes 53 have a width and length enabling the holes to cover a range within which the back end of the wire 35 or of the wire stopper 45 is movable (range E in FIG. 2).

The adjustment knob 34 is formed on the outer circumference of the cam cylinder 51. The adjustment knob and cam cylinder are fixed and coupled to each other by means of a plurality of pins 55 arranged in the circumferential direction. Specifically, pin holes are bored in the adjustment knob 34. The pins 55 that are long enough to reach the cam cylinder 51 lying inside are fitted and locked into the pin holes, and the pin holes are blocked by a filler 56.

The adjustment knob 34 has the front end thereof abutted on an abutment member 57 shaped like an annulus ring and is thus restrained from moving forwards. The abutment member 57 is located outside the front end of the cylindrical tube 43, and fixed to the outer circumference of a support member 58 for supporting the back end of the anti-bending member 10 by means of a screw 59.

At the back end of the adjustment knob 34, the inner circumferential surface of the front end of a grip-portion cylinder 61 is engaged with the outer circumferential surface of the cam cylinder 51. The outer circumferential surface of the front end of the grip-portion cylinder 61 is engaged with a notched portion of the inner circumferential surface of the back end of the adjustment knob 34. That is to say, the adjustment knob 34 is freely rotatable about the cylindrical tube 43 while being restraining from moving back and forth, and located to engage with the outer circumferential surface of the cylindrical tube 43 with the cam cylinder 51 between them. Thus, the adjustment knob 34 can be rotated about the axis thereof, while the abutment member 57 is so as not to rotate by means of the screw 59.

Figure 4A:
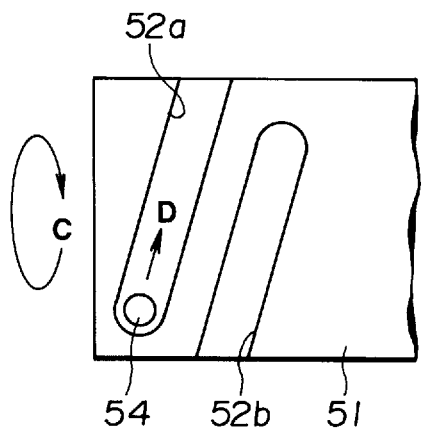
FIG. 4A is an explanatory diagram showing an example of the shape of cam grooves formed in a cam cylinder in the first endoscope.

As shown in FIG. 4A, the cam grooves 52a and 52b formed in the cam cylinder 51 constitute a double-groove cam. One of the two grooves is the cam groove 52a and the other one is the cam groove 52b. As mentioned previously, the cam grooves 52a and 52b have the same shape and are located at symmetrical positions so that when one of the cam grooves is rotated by 180° relative to the axis of the cam cylinder 51, the cam groove will coincide with the other cam groove.

Figure 4B:
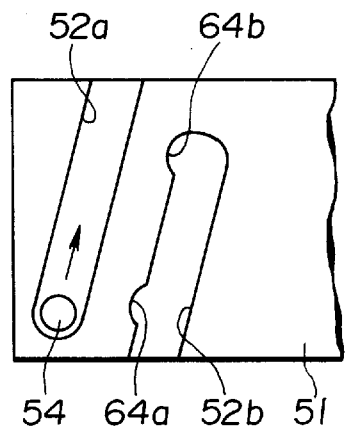
FIG. 4B is an explanatory diagram showing another example of the shape of the cam grooves formed in the cam cylinder in the first endoscope.

The cam grooves 52a and 52b shown in FIG. 4A are shaped like a simple smooth spiral groove. The cam grooves 52a and 52b may not have the structure shown in FIG. 4A. Alternatively, for example, as shown in FIG. 4B, the cam groove 52b may have a recess 64a in the middle thereof or the cam groove 52b may have a recess 64b at an end thereof. In this case, when the pins 54 are trapped into the recesses 64a and 64b, an operator will perceive a click.

Owing to the insertion unit 6 having the foregoing hardness adjustment mechanism, the hardness level of the insertion unit 6 is generally raised. In the first endoscope 2 of this embodiment, measures described below are taken to prevent the insertion unit 6 from getting harder.

Specifically, an example of a structure preventing the insertion unit 6 from getting harder is a structure in which the armor of the soft tube 37 outlining the soft part 13 is made of a soft resin or the thickness of the soft tube 37 is decreased. Thus, the soft tube may be made softer than a conventional tube. Furthermore, a reticulate tube or spiral tube inside the resin armor may be made of a soft material.

Moreover, a tube member forming the treatment appliance passage channel 33 may be made of a material softer than a conventionally used one. For example, although a single-ply tube made of a fluoroethylene resin such as Teflon has been employed in the past, a very thin tube made of Teflon may be used as an inner tube and a two-ply tube made of a porous elastomer may be used as an outer tube.

Moreover, the wire of the coil 36 is made so thin as to have a diameter ranging from 0.45 to 0.7 mm and an outer diameter ranging from 2.0 to 2.5 mm, whereby an adverse effect on the flexibility of the soft part 13 is suppressed. By the way, the wire 35 is designed to enjoy softness and high strength by adopting a strand whose outer diameter ranges from 0.8 to 1.3 mm. When a strand is used as the wire 35, as long as the diameter of the wire is unchanged, the wire 35 formed with a strand gets softer than the one formed with a single wire.

Although a certain degree of deterioration in performance is thinkable, when the diameter of a treatment appliance channel tube and the diameters of other contents are made smaller in order to incorporate a hardness variation means in a vacated area, it can be prevented that the contents get harder as a whole. When the outer diameter of the soft part 13 is made equal to or smaller than a conventionally adopted one, it can be prevented that the soft part gets harder.

As shown in FIG. 2, an insertion port frame 65 for defining the treatment appliance insertion port 32 is located in front of the adjoining grip portion 31 of the operation unit 7. The insertion port frame 65 is joined with a branching member 67 that is, inside the operation unit 7, branching into a portion leading to the treatment appliance insertion port 32 and a portion communicating with a suction tube 66 extending through the universal cord 8. The proximal end of the treatment appliance passage channel 33 lying through the insertion unit 6 is linked to the front end of the branching member 67 by a linkage 68.

The branching member 67 is locked in the cylindrical tube 43 using screws. The cylindrical tube 43 has the back end thereof screwed to a frame 60 to which a bending mechanism included in the operation unit 7 is attached. The cylindrical tube 43 is unitedly fixed to the operation unit 7. Even when the adjustment knob 34 is rotated, the cylindrical tube 43 will not rotate.

Figure 3A:
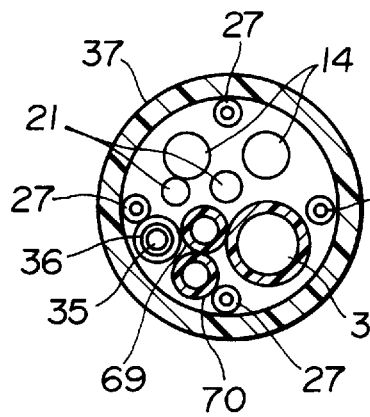
FIG. 3A is a sectional view of the portion of the first endoscope on a 3A—3A plane shown in FIG. 2.
Figure 3B:
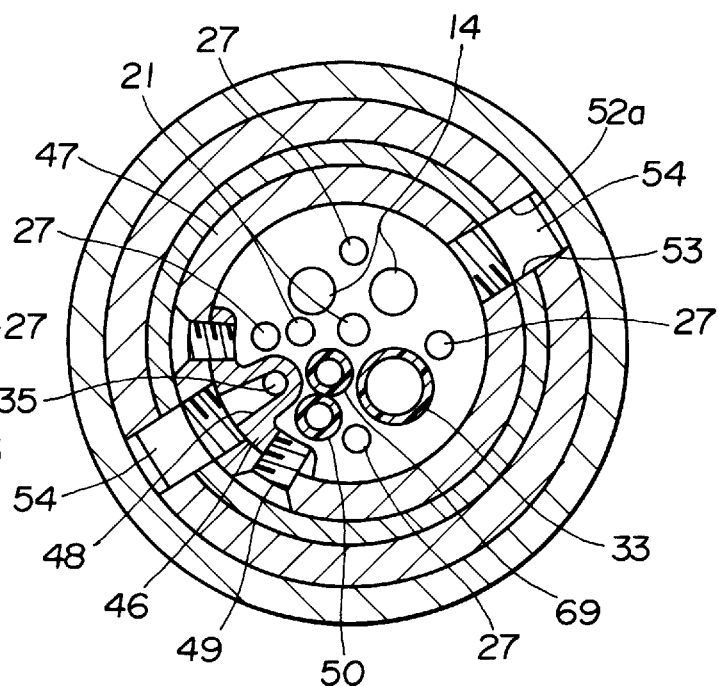
FIG. 3B is a sectional view of the portion of the first endoscope on a 3B—3B plane shown in FIG. 2.

As shown in FIG. 3A, various contents are arranged in the insertion unit 6. Specifically, the four bending wires 27 are arranged up and down at ends of a vertical diameter, and right and left at ends of a horizontal diameter. Two signal cables 21 are arranged near the center of the insertion unit. Two light guides 14 are arranged in an area above the center of the insertion unit. The treatment appliance passage channel 33 is located in an area below the center thereof. The coil 36 and wire 35 are located in the left-hand side of the insertion unit. An aeration tube 69 used to supply air and a perfusion tube 70 used to supply water are adjoining the coil 36 and wire 35. Contents shown in FIG. 3B are arranged in the operation unit 7. The contents are identical to those shown in FIG. 3A though the positions thereof may be different.

As mentioned above, the first endoscope 2 has a function for adjusting the hardness level of the soft part 13 of the insertion unit 6. An insertion unit included in the other second endoscope 102 does not have the hardness adjustment function for adjusting the hardness level of a soft part 113 but has flexibility of the same degree as the flexibility of an ordinary endoscope. The second endoscope has the same components as the first endoscope, though the second endoscope does not include the hardness adjustment function. The second endoscope 102 will be explained briefly below.

The second endoscope 102 comprises an insertion unit 106, operation unit 107, and universal cord 108. A connector 109 to be freely detachably attached to the light source apparatus 3 is attached to the tip of the extending universal cord 108. The insertion unit 106 is joined with the operation unit 107. An anti-bending member 110 is formed at the joint end of the insertion unit. The insertion unit 106 is made by concatenating a distal part 111, bending portion 112, and soft part 113 in that order from the distal end. A light guide and other contents are incorporated in the insertion unit 106. The operation unit 107 has a bending knob 139, grip portion 131, and treatment appliance insertion port 132. The connector 109 of the universal cord 108 includes a light guide connector 115 and a connector 122 for electrical coupling. An external cable 23 extending to the signal processing apparatus 4 is linked to the electrical-coupling connector 122.

Next, the constituent features of this embodiment will be described.

Figure 5:
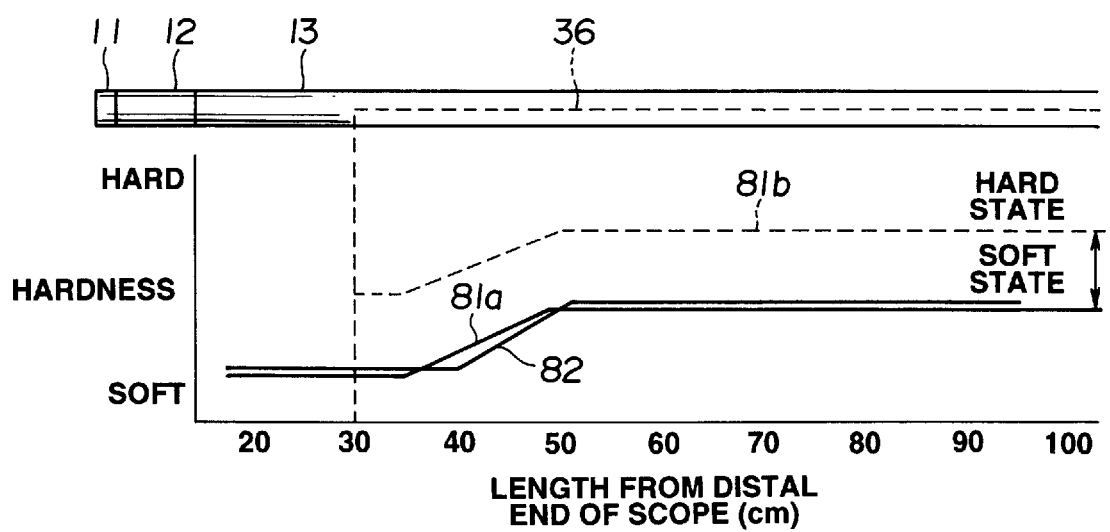

FIG. 5 is a diagram expressing the characteristic balance in hardness of the soft part 13 of the insertion unit 6 of the first endoscope 2 having the hardness adjustment mechanism and the characteristic balance in hardness of the soft part 113 of the insertion unit 106 of the second endoscope 102 not having the hardness adjustment mechanism by indicating hardness levels in relation to lengths from the distal ends of the endoscopes. The characteristic balance in hardness softening the soft part 13 of the first endoscope 2 is expressed with a solid line 81a, and the characteristic balance in hardness hardening the soft part 13 is expressed with a dot line 81b. The characteristic balance in hardness of the soft part 113 of the second endoscope 102 is expressed with a solid line 82. The characteristic balances in hardness 81a, 81b, and 82 imply that the distal sides of the endoscopes are softer and the succeeding portions thereof that succeed the distal sides are harder.

As mentioned above, the characteristic balance in hardness 82 of the second endoscope 102 of this embodiment can be neither adjusted nor varied but merely produces a determined hardness level. Moreover, when the soft part 13 of the first endoscope 2 is adjusted to become softest, the characteristic balance in hardness 81a produces nearly the same hardness level as the hardness level of the second endoscope 102 devoid of the hardness adjustment mechanism. Furthermore, since the distal end of the coil 36 is located at a position about 30 cm away from the tip of the endoscope within the soft part 13, the rise of the dot line expressing the characteristic balance in hardness 81b hardening the soft part to the greatest extent is observed at a scale near the scale of 30 cm indicating the position of the distal end of the coil 36.

Incidentally, in this embodiment, the distal end of the coil 36 is located at the position about 30 cm away from the tip of the endoscope. The position of the distal end of the coil 36 may be any other position, for example, at a position about 20 to 40 cm away from the tip of the endoscope.

Referring to FIG. 6, an example of a procedure for inserting the first endoscope 2 or second endoscope 102 into the large intestine will be described.

To begin with, a procedure for inserting the first endoscope 2 will be described.

Figure 6A:
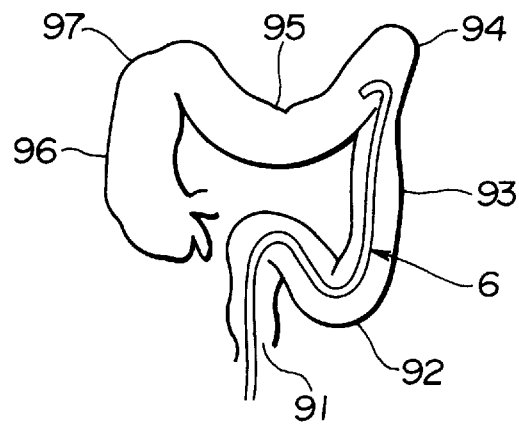
FIGS. 6A to 6C are diagrams for explaining states in which the first endoscope or second endoscope included in the endoscope system of this embodiment is inserted into the large intestine through the anus.
Figure 6B:
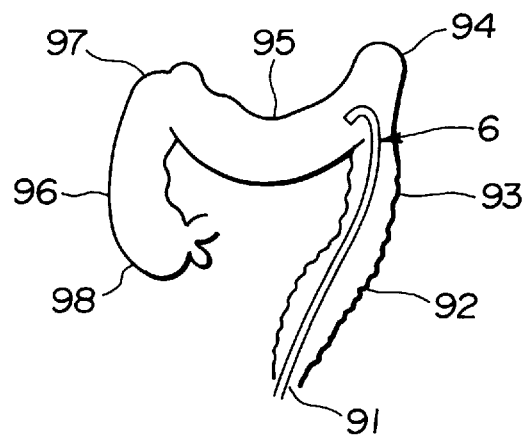
Figure 6C:
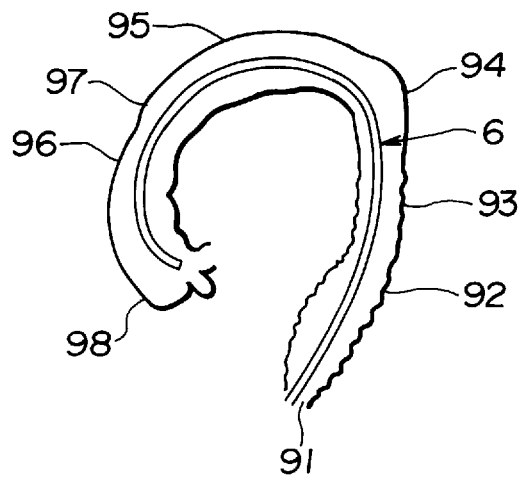

First, with the soft part 13 softened, the distal part 11 of the insertion unit 6 is, as shown in FIG. 6A, inserted through the anus 91, passed through the tortuous sigmoid colon 92 and descending colon 93, and routed to a position near the splenic curvature 94. By manipulating the endoscope proximally, the soft part 13 is pulled while being twisted and thus substantially straightened. Accordingly, as shown in FIG. 6B, the tortuous part of the sigmoid colon 92 is collapsed to be contracted and thus substantially straightened. The adjustment knob 34 is then rotated in order to harden the coil 36 of the hardness adjustment mechanism. The soft part 13 is then hardened and the insertion unit 6 is thrust forward. The insertion unit 6 can, as shown in FIG. 6C, be passed through the sigmoid colon 92 and transverse colon 95 but not be deflected largely as shown in FIG. 6A. While a manipulating force can be conveyed reliably from the proximal side of the soft part 13 to the distal side thereof, the insertion unit can be inserted smoothly to a deep region in the large intestine.

Next, a procedure for inserting the second endoscope 102 will be described.

First, similar to the procedure for inserting the first endoscope 2, the distal part 111 is routed to a position near the splenic curvature 94. The endoscope is manipulated to pull the soft part 113 while twisting the soft part. The sigmoid colon 92 is collapsed to be contracted. Thereafter, the distal part is inserted to the deep region shown in FIG. 6C. At this time, as much attention as possible should be paid for fear the sigmoid colon 92 and transverse colon 95 be deflected as shown in FIG. 6A. However, since the second endoscope 102 does not have the function for hardening the soft part 113, there is a possibility that during insertion of the second endoscope 102, the sigmoid colon 92 and transverse colon 95 may be deflected again as shown in FIG. 6A depending on an individual difference of one patient from another or a difference in skill of one operating technician from another. It may therefore become difficult to insert the endoscope.

Incidentally, the first endoscope 2 and second endoscope 102 are different from each other in terms of not only the hardness adjustment function but also image quality and the size of a treatment appliance channel. For example, one of the endoscopes can provide normal image quality while the other can provide high image quality, or one of the endoscopes includes a treatment appliance channel of a normal size while the other includes a large treatment appliance channel. Moreover, the first and second endoscopes may be mutually different in terms of any other function.

As mentioned previously, when endoscopes have different functions, it may take place that the same operator uses the first endoscope to examine a certain patient and uses the second endoscope 102 to examine another patient, and thus uses the first endoscope 2 and second endoscope 102 for different purposes. When the number of examinations to be conducted per day increases, it may become necessary to prepare two endoscopes of the first endoscope 2 and second endoscope 102 for use within the endoscope system 1 so as to thus improve examination efficiency. Such a situation may arise that when the first endoscope 2 is used to examine a certain patient, while the first endoscope 2 is cleaned and sterilized, the second endoscope 102 is used to examine another patient. For coping with the situation, it is thinkable that the second endoscope 102 which has been available in the past is purchased first, and thereafter, the first endoscope 2 which has been put on the market recently is purchased or vice versa.

Under the circumstances, it will presumably become a matter of common practice that the same user uses a plurality of endoscopes having different functions, such as, the first endoscope 2 and second endoscope 102.

As indicated with the solid line in FIG. 5, when the characteristic balance in hardness 81a of the first endoscope 2 and the characteristic balance in hardness 82 of the second endoscope 102 are nearly identical to each other, the endoscopes 2 and 102 can be used for different purposes without a sense of incompatibility.

However, assume that the characteristic balance in hardness of the second endoscope 102 greatly deviates from an adjustable range or a range of hardness levels within which the characteristic balance in hardness of the first endoscope 2 can be adjusted, that is, a range of hardness levels defined with the solid line 81a and dot line 81b, for example, assume that the characteristic balance in hardness 81a softening the first endoscope 2 produces a higher hardness level than the characteristic balance in hardness 82 of the second endoscope 102. In this case, when an operator who is familiar with the second endoscope 102 having the characteristic balance in hardness 82 purchases and operates the endoscope 2 newly, (i.e. shortly after purchasing) the endoscope 2 may be an endoscope having hardness which the operator has not experienced. When using an endoscope whose insertion unit is harder than that of an endoscope familiar to an operator, the operator must pay close attention in inserting the endoscope into a patient. Otherwise, the operator may cause the patient to feel a great pain. Although the patient may not feel any pain because of anesthesia, the possibility of damaging the large intestine increases.

However, in the endoscope 2 of this embodiment, as shown in FIG. 5, the characteristic balance in hardness 81a softening the first endoscope 2 and the characteristic balance in hardness 82 of the second endoscope 102 produce nearly the same hardness levels. An operator who is familiar with the second endoscope 102 can make the most of the first endoscope that is softened without a sense of incompatibility. When the operator gets accustomed to the first endoscope 2 that is softened, the characteristic balance in hardness of the first endoscope 2 is adjusted little by little in order to harden the first endoscope. Thus, the operator can get accustomed to the hardened endoscope. If the operator fails to insert the hardened endoscope, the operator should merely re-set the endoscope to the familiar soft state and try to insert the endoscope again. Thus, the characteristic balance in hardness of the first endoscope can be returned right away to the same characteristic balance in hardness as that of the familiar second endoscope 102. The operator can therefore use the newly-purchased first endoscope 2 without concern.

On the contrary, when an operator who has become accustomed to the hardness adjustment mechanism of the first endoscope 2 intends to newly use the second endoscope 102 later, since the operator familiar with the first endoscope 2 has some experience in the range of hardness levels from the hardness level produced by the characteristic balance in hardness softening the first endoscope 2 to the hardness level produced by the characteristic balance in hardness hardening the first endoscope, the operator can make the most of the second endoscope 102 without having a sense of incompatibility. For example, the characteristic balance in hardness 82 in FIG. 5 is similar to the characteristic balance in hardness 81a softening the first endoscope. The second endoscope 102 can therefore be utilized without a sense of incompatibility.

When the soft part of the second endoscope 102 is hardened, if the characteristic balance in hardness 82 of the second endoscope produces a higher hardness level than the characteristic 81b balance in hardness hardening the first endoscope 2, even an operator familiar with the first endoscope 2 has no experience in the hardness produced by the characteristic balance in hardness 82. Under these circumferences, as mentioned previously, the operator is likely to cause a patient to feel a great pain or the possibility of damaging the large intestine increases.

The hardness levels produced by the characteristic balances in hardness of the first endoscope 2 ranging from the characteristic balance in hardness softening the first endoscope to the characteristic balance in hardness hardening the first endoscope, and the hardness level produced by the characteristic balance in hardness of the second endoscope 102 must be set carefully for fear such an event might occur.

Talking of the hardness level of the soft part 13, the hardness of the portion of the soft part from the distal end thereof to a position near the distal end of the coil 36 counts most. This is because when the soft part 13 works on a living body, the distal side thereof first works and then the subsequent part thereof does. In particular, the portion of the soft part near the distal end of the hardness variation coil 36 is the first portion whose hardness can be varied intentionally by an operator. It has therefore a significant meaning how well the hardness of the soft part at a position about 30 cm away from the tip of the endoscope is familiar to the operator.

As shown in FIG. 5, the characteristic balance in hardness 82 of the portion of the soft part 13 or 113 extending from a position about 40 cm away from the tip of the endoscope to a position about 50 cm away from it is plotted outside the range defined by the characteristic balance in hardness 81*a* softening the endoscope and the characteristic balance in hardness 81*b* hardening the endoscope. The characteristic balance in hardness 82 apparently produces a lower hardness level than the characteristic balance in hardness 81*a* of the same portion. What is important is the characteristic balance in hardness of the portion of the soft part distal to the position about 30 cm away from the tip of the endoscope. The characteristic balance in hardness falls within the range defined by the characteristic balance in hardness 81*a* softening the endoscope and the characteristic balance in hardness 81*b* hardening the endoscope (can be said to be nearly identical to the characteristic balance in hardness 81*a* softening the endoscope). Consequently, an effect of allowing an operator to feel familiar with the endoscope in terms of usage can be exerted fully.

Moreover, the hardness variation mechanism of the first endoscope 2 is used to adjust the characteristic balance in hardness of the soft part 13 so as to select the values of the hardness level produced by the characteristic balance in hardness. In this case, after the adjustment knob 34 is rotated for adjustment and then released, it should preferably be held (locked) at the adjusted position. After rotated, the adjustment knob 34 may be held at any other position by utilizing friction occurring due to sliding of, for example, angular rotational contacts shown in FIG. 2. Alternatively, a locking mechanism to be operated by manipulating a lock lever or knob that is not shown may be used to lock the adjustment knob at any other position.

Moreover, the adjustment knob may be locked by trapping the pins 54 into the recesses 64*a* formed in the cam grooves 52*a* and 52*b* as shown in FIG. 4*b*. This enables an operator to perceive a click and helps the operator realize that the same hardness level as that produced by the characteristic balance in hardness 82 is attained.

The description of this embodiment has proceeded on the assumption that the characteristic balance in hardness 82 of the second endoscope 102 produces nearly the same hardness level as that produced by the characteristic balance in hardness 81*a* softening the first endoscope. Alternatively, the characteristic balance in hardness 82 may produce nearly the same hardness level as the characteristic balance in hardness 81*b* hardening the first endoscope. Even in this case, an operator feels familiar with two types of endoscopes in terms of usage.

As mentioned above, in the endoscope system of this embodiment, an operator can use two endoscopes with and without a hardness variation mechanism while feeling familiar with both of them. Moreover, since the hardness variation mechanism is incorporated in an endoscope, when a component for preventing the hardness level of an insertion unit from getting higher is included, the endoscope can be set to the same hardness level as an endoscope whose insertion unit is devoid of the hardness variation mechanism.

Figure 7:
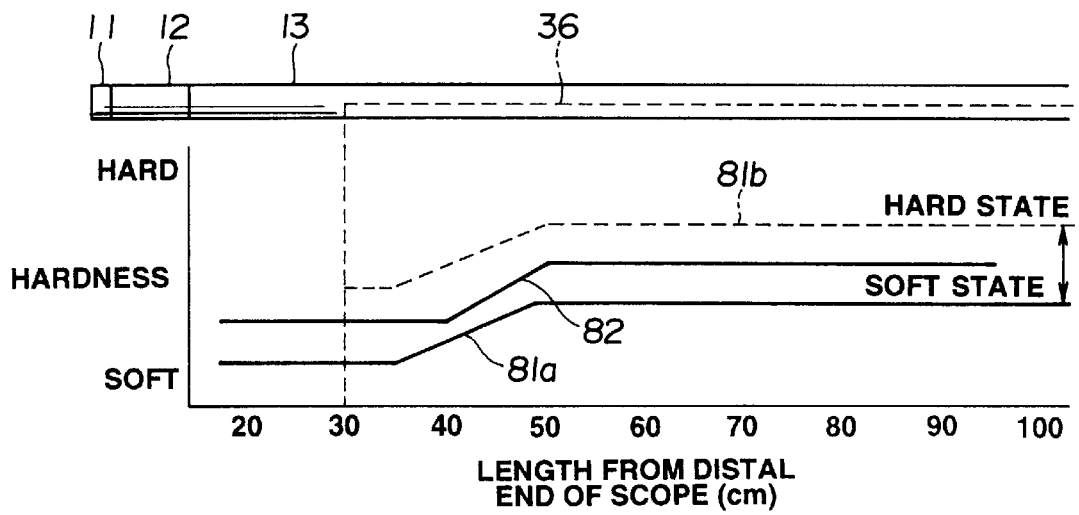
FIG. 7 is a diagram expressing the characteristic balances in hardness of endoscopes included in an endoscope system in accordance with the second embodiment of the present invention.

Referring to FIG. 7, the second embodiment of the present invention will be described.

In an endoscope system of this embodiment, the characteristic balance in hardness of the second endoscope 102 is defined to produce an intermediate hardness level between those produced by the characteristic balance in hardness 81*a* softening the soft part 13 of the first endoscope 2 and the characteristic balance in hardness hardening the soft part 13 of the first endoscope 2. The other components are identical to those in the first embodiment.

When the characteristic balance in hardness of the first endoscope 2 is adjusted using the hardness variation mechanism so that the characteristic balance in hardness will produce nearly the same hardness level as the characteristic balance in hardness 82 of the second endoscope 102, even if the adjustment knob 34 is released, the adjustment knob 34 can be locked in the rotated state. In this case, when rotated, the adjustment knob 34 may be held at any position by utilizing friction occurring due to sliding of, for example, rotational contacts. Alternatively, as shown in FIG. 4B, the adjustment knob 34 may be locked by trapping the pins 54 into the recesses 64*a* of the cam grooves 52*a* and 52*b,* so that the characteristic balance in hardness of the first endoscope 2 will be defined to produce a hardness level close to the hardness level produced by the characteristic balance in hardness 82 of the second endoscope 102. In this case, an operator perceives a click made by the recesses 64*a* to realize that the characteristic balance in hardness of the first endoscope 2 has been defined to produce the same hardness level as the hardness level produced by the characteristic balance in hardness 82 of the second endoscope 102.

When an operator familiar with the second endoscope 102 exhibiting the characteristic balance in hardness 82 intends to newly use the first endoscope 2 exhibiting the characteristic balance in hardness 81*a,* the first endoscope 2 that is softened and exhibits the characteristic balance in hardness 81*a* is apparently softer than the second endoscope 102 exhibiting the characteristic balance in hardness 82 and therefore incompatible with the second endoscope 102. However, although the first endoscope 2 and second endoscope 102 are incompatible with each other, as long as the first endoscope 2 is softer, it will hardly take place that a patient feels a great pain or the large intestine is damaged. Consequently, the operator may feel the first endoscope 2 too soft initially and have difficulty in inserting it swiftly. However, there is not problem in terms of patient's safety.

When the operator wants to set the first endoscope to the same hardness level as the hardness level of the second endoscope 102 exhibiting the characteristic balance in hardness 82 and familiar to the operator, he/she manipulates the adjustment knob 34 for adjustment. Thus, the balance in hardness of the proximal side of the soft part beyond the position about 30 cm away from the tip of the endoscope can be defined to produce a hardness level resembling the one produced by the characteristic balance in hardness 82.

On the other hand, when an operator familiar with the first endoscope 2 intends to newly use the second endoscope 102, he/she has no experience in the hardness of a portion of the soft part near a position about 20 cm away from the tip of the endoscope. The operator must therefore pay attention initially. However, since the hardness of a portion proximal to the position 30 cm away from the tip of the endoscope falls within the range of hardness levels the operator has experienced while using the first endoscope 2, he/she will find the second endoscope compatible with the first endoscope even from the viewpoint of ease of use. Moreover, the operator will find the endoscope considerably easier to use than an endoscope whose soft part is unfamiliar to the operator.

Aside from the procedure described in conjunction with FIG. 6 in which the hardness level of the soft part 13 is changed in the course of insertion, there is a procedure for inserting the first endoscope 2 into the large intestine by selecting a hardness level suitable for a patient from the beginning. Specifically, the large intestine is considerably different from patient to patient. This becomes a great factor making it difficult to insert the endoscope into the large intestine. For example, as far as the sigmoid colon is concerned, a procedure for inserting a soft insertion unit while looping it may be suitable for a certain patient, and a procedure for inserting a hard insertion unit while striving not to loop it may be suitable for another patient.

Assuming that the second endoscope 102 has an intermediate hardness level permitting the endoscope to be used for examination of both the patients, since the first endoscope 2 can be softened or hardened more greatly than the second endoscope 102, an operator familiar with the second endoscope 102 can enjoy excellent insertional smoothness suitable for every patient.

An operator familiar with the first endoscope 2 finds the hardness of the second endoscope 102 of this embodiment intermediate. Compared with when the hardness of the second endoscope 102 of the first embodiment is set to an extreme level such as a level at which the second endoscope is softened or hardened to the greatest extent, any patient can be examined to some extent using the first and second endoscopes of this embodiment.

As mentioned above, according to the endoscope system of this embodiment, the first endoscope and second endoscope are a lineup making it possible to cope with individual differences among patients and are easy for an operator to use.

Figure 8:
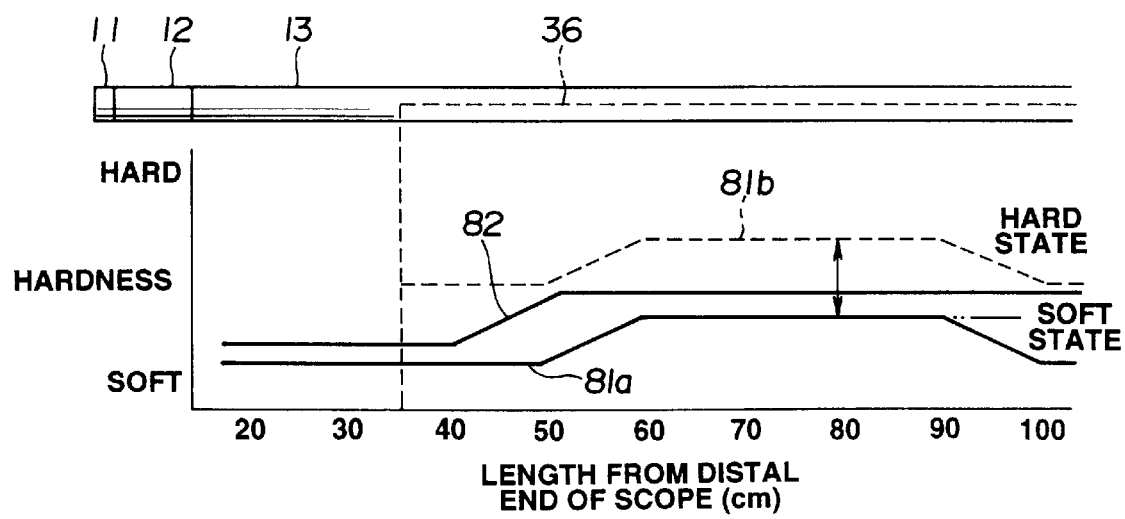

Referring to FIGS. 8 and 9, the third embodiment of the present invention will be described.

As shown in FIG. 8, a constituent feature of this embodiment is the characteristic balance in hardness 81*a* hardening the soft part 13 of the first endoscope 2. A proximal side of the soft part 13 beyond a position 90 cm away from the tip of the endoscope is soft. All the characteristic balances in hardness ranging from the characteristic balance in hardness softening the soft part to the one hardening the soft part are adjusted to exhibit such a decrease in hardness in relation to larger lengths from the tip of the endoscope.

For defining the balances as mentioned above, presumably, when at least part of the soft tube 37 forming the soft part 13 is made of a resin, the composition of the resin may be made different between both sides of the soft tube distal and proximal to a position about 90 cm away from the tip of the endoscope, for example, the composition of the resin to be made into the proximal side may provide higher-level softness, and thus the property of the material of the soft tube 37 may be changed between both the sides thereof. Otherwise, the property of the coil 36 may be changed, or the contents of the soft tube 37 may be modified properly.

Figure 9A:
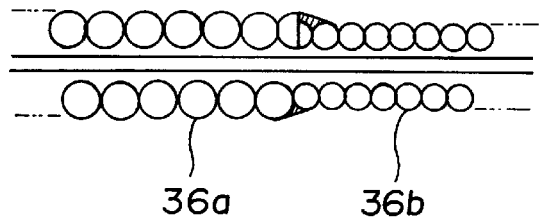
FIG. 9A is an explanatory diagram showing an example of a hardness adjustment coil in a first embodiment.
Figure 9B:
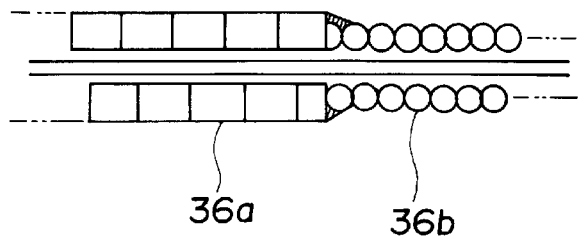

For modifying the structure of the coil 36 properly, for example, as shown in FIGS. 9A and 9B, the coil 36 is divided into a distal coil 36*a* and proximal coil 36*b* or structured by concatenating a plurality of coils. In FIG. 9A, the plurality of coils 36*a* and 36*b* having substantially the same inner diameter but different outer diameters are concatenated. In FIG. 9B, the inner and outer diameters of the coils are substantially the same but the shape of the cross section of the wire of one coil is different from that of the other coil. In FIG. 9B, the cross section of the distal coil 36*a* is nearly rectangular while that of the proximal coil 36*b* is spherical.

In this embodiment, the characteristic balance in hardness 81*b* hardening the first endoscope 2 is defined so that the hardness level of the proximal side beyond a position about 100 cm away from the tip of the endoscope will be nearly the same as the hardness level produced by the characteristic balance in hardness 82 of the second endoscope 102.

In this embodiment, the portion of the soft part 13 extending from a position 90 cm away from the tip of the endoscope to a position 100 cm away from it is gradually softened. Alternatively, the portion may be sharply softened. The other components are identical to those in the first embodiment.

When an endoscope is inserted into the large intestine, the soft part 13 of the insertion unit 6 may be twisted. In this embodiment, when the proximal side of the soft part 13 is softened to exhibit the hardness level indicated with the solid line expressing the characteristic balance in hardness 81*a* in FIG. 8, if the soft part 13 is twisted by gripping a portion extending from a position 50 cm away from the tip of the endoscope to a position 90 cm away from it, the proximal side of the soft part beyond the gripped position is likely to loop according to the magnitude of twisting. That is to say, since a quantity of force required for twisting is small, an operator can twist the soft part easily.

As far as the characteristic balances in hardness shown in FIG. 7 are concerned, when the soft part is hardened, the characteristic balance in hardness 81*b* produces a considerably higher hardness level for the proximal side of the soft part than the characteristic balance in hardness 82. During twisting, therefore, an operator will feel the soft part heavier than when the soft part exhibits the characteristic balance in hardness 82. However, in this embodiment, even when the characteristic balance in hardness 81*b* hardening the endoscope is adopted as a characteristic balance in hardness, the proximal side beyond a position about 100 cm away from the tip of the endoscope has the same hardness as when the proximal side exhibiting the characteristic balance in hardness 82. Twisting smoothness is therefore as good as that ensured by the characteristic balance in hardness 82.

Moreover, as far as the structures shown in FIGS. 9A and 9B are concerned, when the coil is bent, a contact point at which wires come into contact with each other does not become very hard because the coil 36*b* is located closer to the center axis than the coil 36*a* is and the coil 36*b* is harder than the coil 36*a*.

In this case, the characteristic balance in hardness 81 softening the endoscope is expressed with an alternate long and two short dashes line in FIG. 8. According to the characteristic balance in hardness hardening the endoscope, the portion beyond a position about 100 cm away from the tip of the endoscope does not become very hard.

As for the second endoscope 102, the characteristic balance in hardness 82 to be exhibited by the soft part 113 may be defined so that the proximal side beyond a position about 90 cm away from the tip of the endoscope will be softer. For inserting the endoscope into a deep region in the large intestine, when the soft part 113 is inserted into a living body by 90 cm or larger in length, the proximal side of the soft part 113 is likely to deflect inside the living body. There arises a possibility that a manipulation made proximally may be hardly conveyed to the distal part of the endoscope. Once the characteristic balance in hardness of the first endoscope 2 is set to the characteristic balance in hardness hardening the first endoscope, the soft proximal side becomes as hard as a proximal side exhibiting the characteristic balance in hardness 82. When the endoscope is inserted into the deep region, it can therefore be prevented that the soft part deflects more readily than a soft part exhibiting the characteristic balance in hardness 82. As long as the coil 36 is placed to extend ahead of the soft proximal side within an area of which characteristic balance in hardness is adjustable, the effect of preventing deflection can be exerted.

As mentioned above, according to the endoscope system of this embodiment, the smoothness in twisting the soft part that is hardened can be improved.

Figure 10:
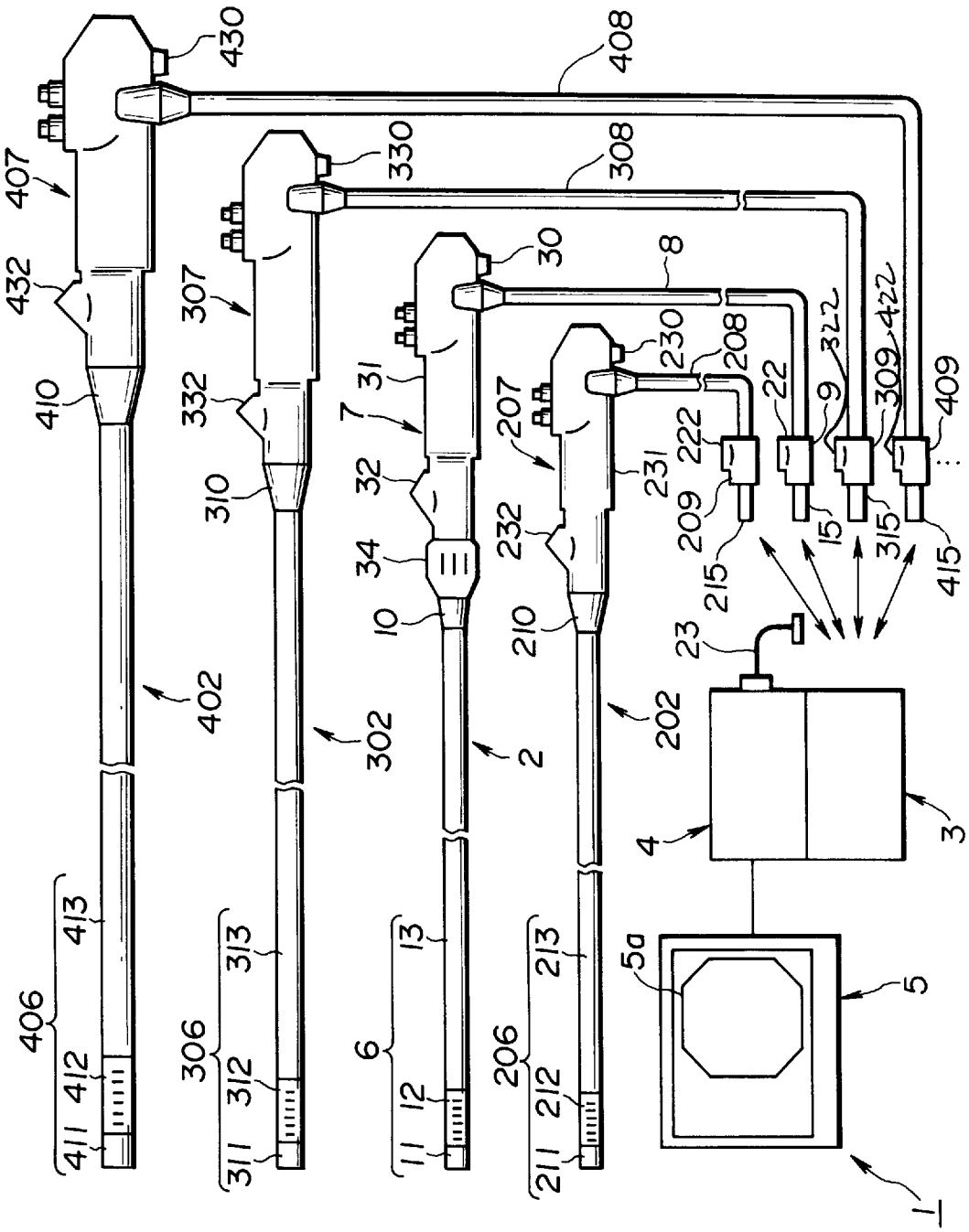
FIGS. 10 and 11 are diagrams for explaining the fourth embodiment of the present invention.
Figure 11:
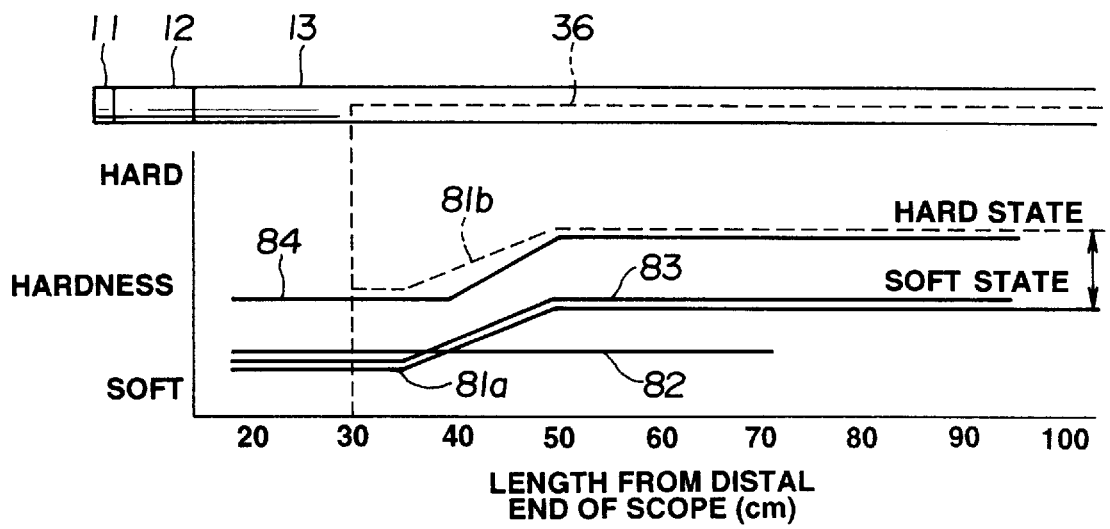

Referring to FIGS. 10 and 11, the fourth embodiment of the present invention will be described.

As shown in FIG. 10, the endoscope system of this embodiment has endoscopes 202, 302, and 402 in addition to the first endoscope 2 and is an example having a large number of types of endoscopes. Incidentally, a larger number of endoscopes may be included.

The endoscopes 202, 302, and 402 have insertion units 206, 306, and 406, operation units 207, 307, and 407, and universal cords 208, 308, and 408. Connectors 209, 309, and 409 freely attachable or detachable to or from the light source apparatus 3 are attached to the universal cords 208, 308, and 408 respectively. The connectors 209, 309, and 409 have light guide connectors 215, 315, and 415, and connectors for electrical coupling 222, 322, and 422 respectively. The insertion units 206, 306, and 406 are joined with the operation units 207, 307, and 407 respectively. Anti-bending members 210, 310, and 410 are formed at the joint ends of the insertion units respectively. The operation units 207, 307, and 407 have bending knobs 230, 330, and 440, and treatment appliance insertion ports 232, 332, and 432 respectively. Furthermore, the insertion units 206, 306, and 406 are composed of distal parts 211, 311, and 411, bending portions 212, 312, and 412, and soft parts 213, 313, and 413 respectively in that order from the distal ends thereof.

The characteristic balances in hardness of the soft parts 13, 213, 313, and 413 of the endoscopes 2, 202, 302, and 402 are expressed with solid and dot lines 81 to 84 in FIG. 11. The insertion unit 206 of the endoscope 202 is relatively short, and the soft part 213 thereof is relatively soft over the whole length. As far as the distal sides of the endoscope 202 and first endoscope 2 are concerned, the characteristic balance in hardness 82 of the endoscope 202 produces nearly the same hardness level as the characteristic balance in hardness softening the first endoscope 2 or a slightly higher hardness level. Moreover, the insertion unit 306 of the endoscope 302 has a relatively small diameter. The characteristic balance in hardness 83 of the endoscope 302 produces as a whole nearly the same hardness as the characteristic balance in hardness 81a softening the endoscope 2. Furthermore, the insertion unit 406 of the endoscope 402 has a larger diameter than the insertion unit 306 of the endoscope 302. As far as the proximal sides of the endoscopes 402 and 2 are concerned, the characteristic balance in hardness 84 of the endoscope 402 produces nearly the same hardness as the characteristic balance in hardness 81b hardening the endoscope 2.

When an operator familiar with the endoscopes 202, 302, and 402 intends to newly purchase and use the endoscope 2 afterwards, the characteristic balance in hardness 81a softening the newly-purchased endoscope 2 is nearly identical to the characteristic balance in hardness 83 of the endoscope 302. The characteristic balance in hardness 81b hardening the endoscope 2 is nearly identical to the characteristic balance in hardness 84 of the endoscope 402. The operator can easily use the endoscope exhibiting the characteristic balance in hardness 81a in the soft state and the characteristic balance in hardness 81b in the hard state without a sense of incompatibility.

Moreover, the characteristic balance in hardness 81a softens the distal side of the soft part beyond a position 35 cm away from the tip of the endoscope to such an extent that the distal side will be softer than the corresponding part of the endoscope 202 exhibiting the characteristic balance in hardness 82. Safety of a patient can therefore be guaranteed.

On the other hand, when an operator familiar with the endoscope 2 newly uses the endoscopes 202, 302, and 403, as long as he/she remembers the feelings of the hardness levels ranging from the hardness level produced by the characteristic balance in hardness softening the second endoscope 2 to the characteristic balance in hardness hardening the second endoscope 2, he/she can use the endoscopes without a sense of incompatibility.

As mentioned above, the characteristic balance in hardness of an endoscope can reproduce hardness similar to the hardness levels of the soft parts of a plurality of other types of endoscopes. When an indicator indicating a hardness level is formed on the outer surface of the adjustment knob 34 so that a hardness level can be adjusted by setting the adjustment knob 34 to a certain indication, adjustment work can be carried out easily. Moreover, when an operator can designate an indication reading a hardness level similar to the hardness of a certain type of endoscope, he/she can grasp the relationship of one type of endoscope with another type of endoscope. Moreover, it becomes easy to select and adjust a hardness level.

In the endoscope system of this embodiment, the characteristic balances in hardness softening and hardening the endoscope 2 to the greatest extent correspond to the characteristic balances in hardness 83 and 84 of the other types of endoscopes 302 and 402. The characteristic balances in hardness 83 and 84 can be more easily understood by an operator than the characteristic balances in hardness that are intermediate between the characteristic balances in hardness softening and hardening the endoscope 2. The limits of rotation of the adjustment knob 34 indicate the characteristic balances in hardness 83 and 84 respectively. The hardness levels produced by the characteristic balances in hardness 83 and 84 can therefore be recognized without a look at the indicator.

Moreover, when both the characteristic balances in hardness 83 and 84 are intermediate between the characteristic balances in hardness softening and hardening the endoscope 2 (the characteristic balance in hardness 84 produces higher-level hardness than the characteristic balance in hardness 83), if the adjustment knob 34 can be held at any position or can be locked at the position, the endoscope can be used easily while retained to exhibit a characteristic balance in hardness similar to the characteristic balance in hardness 83 or 84.

When an operator uses endoscopes having different hardness levels according to an individual difference in the large intestine of one patient from another or a plurality of operators use the same endoscope system, the endoscopes having different hardness levels may be employed according to a difference in insertion procedure or likes of an operator. Since the range of levels of the adjustable hardness of the endoscope 2 include the hardness levels of a plurality of different types of endoscopes to be operated within the same system, the hardness adjustment mechanism of the endoscope 2 can be utilized sufficiently within the endoscope system.

As mentioned above, owing to the foregoing endoscope system of this embodiment, an endoscope with a hardness variation mechanism becomes compatible with a larger number of types of endoscopes. The ease of use further improves.

Figure 12:
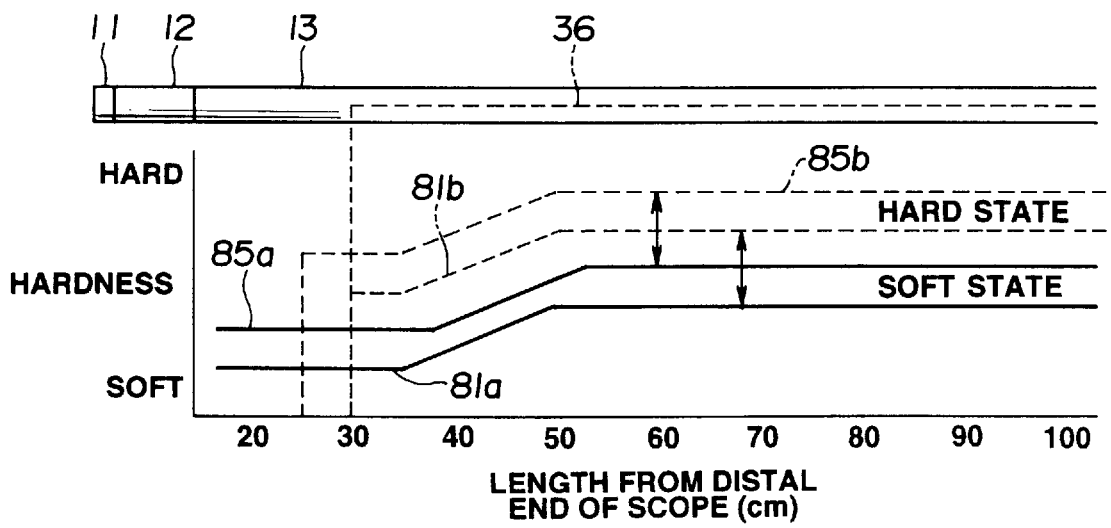
FIG. 12 is a diagram expressing the characteristic balances in hardness of endoscopes included in an endoscope system in accordance with the fifth embodiment of the present invention.

Referring to FIG. 12, the fifth embodiment of the present invention will be described.

This embodiment is an example in which an endoscope system includes a plurality of types of endoscopes each having a hardness variation mechanism. As shown in FIG. 12, the characteristic balances in hardness 81a and 81b of one endoscope, and the characteristic balances in hardness 85a and 85b of the other endoscope are expressed with solid lines and dot lines. Widths between the characteristic balances in hardness hardening and softening the endoscopes overlap.

Since the hardness of the soft part of an endoscope is partly different, when an operator familiar with one endoscope uses the other endoscope, if both the endoscopes have areas whose hardness levels are the same, he/she will find the other endoscope compatible with one endoscope. Moreover, since the endoscopes have areas whose hardness levels are mutually different, hardness levels that cannot be covered by one endoscope can be covered by the other endoscope. Using the two endoscopes in combination, therefore, an operator can use the endoscopes for different purposes within a very wide range of hardness levels. If an operator has difficulty in inserting an endoscope having unfamiliar hardness, he/she can set the endoscope to a familiar hardness level which is shared with the other endoscope.

As mentioned above, according to the endoscope system of this embodiment, a plurality of endoscopes each having a hardness variation mechanism can be made mutually compatible. At the same time, a wide range of hardness levels uncovered by one endoscope having the hardness variation mechanism can be produced by one endoscope system.

Figure 13:
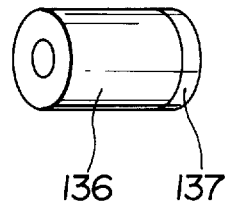
FIGS. 13 and 14 are diagrams for explaining an example of a sheath of a hardness adjustment mechanism.
Figure 14:
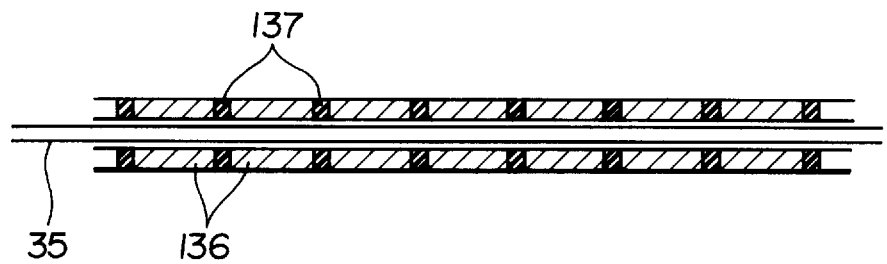

In the foregoing endoscope system of this embodiment, the hardness variation mechanism is composed of a coil and wire. Alternatively, a shape memory alloy may be adopted, fluid pressure may be utilized, or a coil that is as large as to enclose the other contents may be employed. Otherwise, other various means may be usable. Instead of the coil, annulus rings 136 like the one shown in FIG. 13 may be lined up with the wire 35 passed through them as shown in FIG. 14 in order to produce flexibility.

The annulus rings 136 are each made of, for example, stainless steel and has a member having elasticity, such as a rubber ring 137 attached to one end thereof using an adhesive or the like. When the wire is not towed, the adjoining annulus rings 136 are loosely in contact with each other with the ring 137 between them. In this state, the annulus rings 136 with the rubber rings 137 among them can be bent freely and thus the endoscope is softened. When the wire 35 is towed, the rings 137 among the adjoining annulus rings 136 are compressed, and the annulus rings 136 are hard to bend. In this state, the endoscope is less flexible and hardened. The other structures are identical to those in the aforesaid embodiment. For example, the tip of the wire 35 is fixed to the linking tube 38. The leading annulus ring 136 is fixed to the wire 35 at a position a little behind the position at which the tip of the wire is fixed. The backward movement of the trailing annulus ring 136 is restricted by the coil stopper 40. The wire 35 lying through the annulus rings 136 is extending behind the coil stopper 40.

Figure 15:
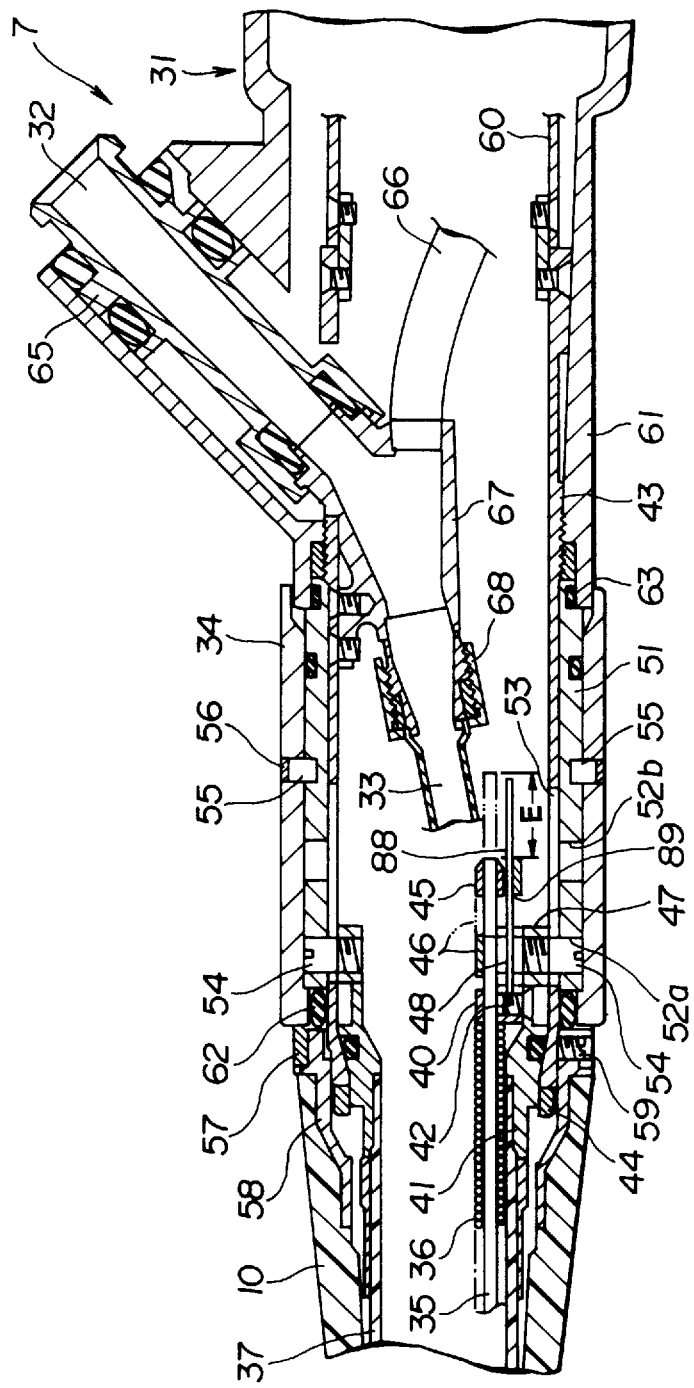
FIG. 15 is a diagram for explaining a structure in which one end of a bar member is fixed to a coil stopper lying in an operation unit.

When a tensile force is applied to the wire 35 formed with a strand, the wire attempts to rotate in a direction in which the wire is untwisted. When the wire rotates in that way, the strand is untwisted and the wire 35 is stretched. While tension is repeated, the wire 35 may not be able to return to an original state. This leads to a deteriorated hardness variation function. One end of a bar member 88 is, as shown in FIG. 15, fixed to the coil stopper 40. The bar member 88 extends backwards through the groove 48 of the coil stopper 40 and a hole 89 of the wire stopper 45. The coil stopper 40 and towing member 46 can slide over the bar member 88. This enables the wire stopper 45 at the back end of the wire 35 to slide without rotating. It can therefore be prevented that the strand forming the wire 35 is untwisted and stretched. The other components are identical to those shown in FIG. 2. The same reference numerals will be assigned to the same members. The description of the members will be omitted.

Figure 16:
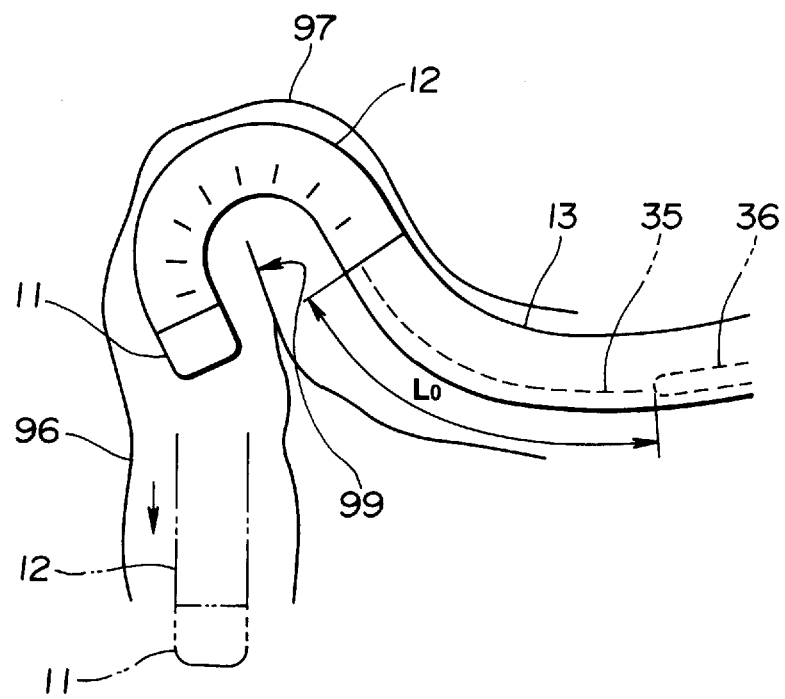
Figure 17A:
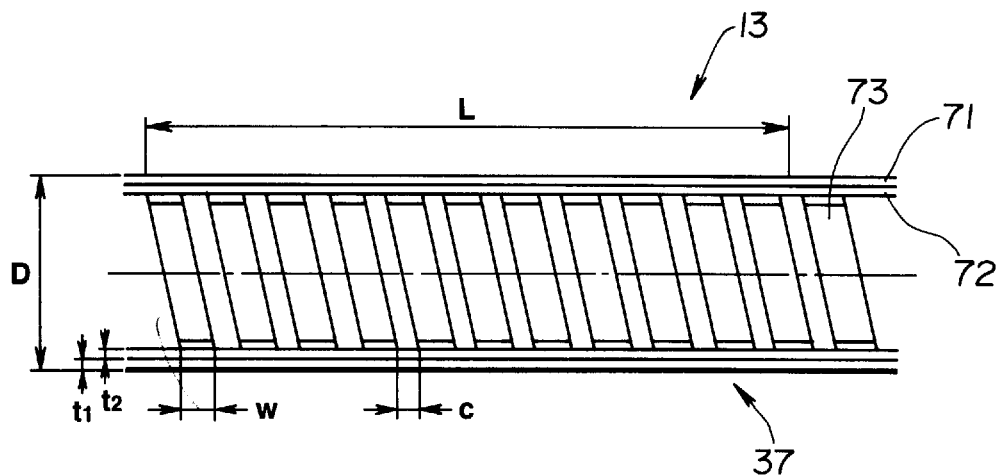
FIG. 17A is a diagram showing the schematic structure of a soft tube forming the soft part and the dimensions thereof.
Figure 17B:
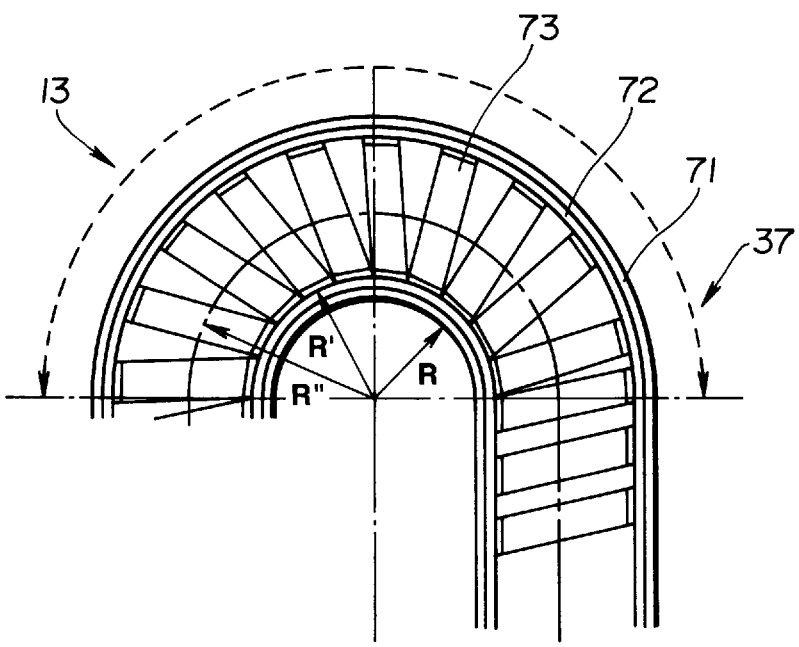
FIG. 17B is a diagram showing a state in which the soft part is bent.
Figure 18:
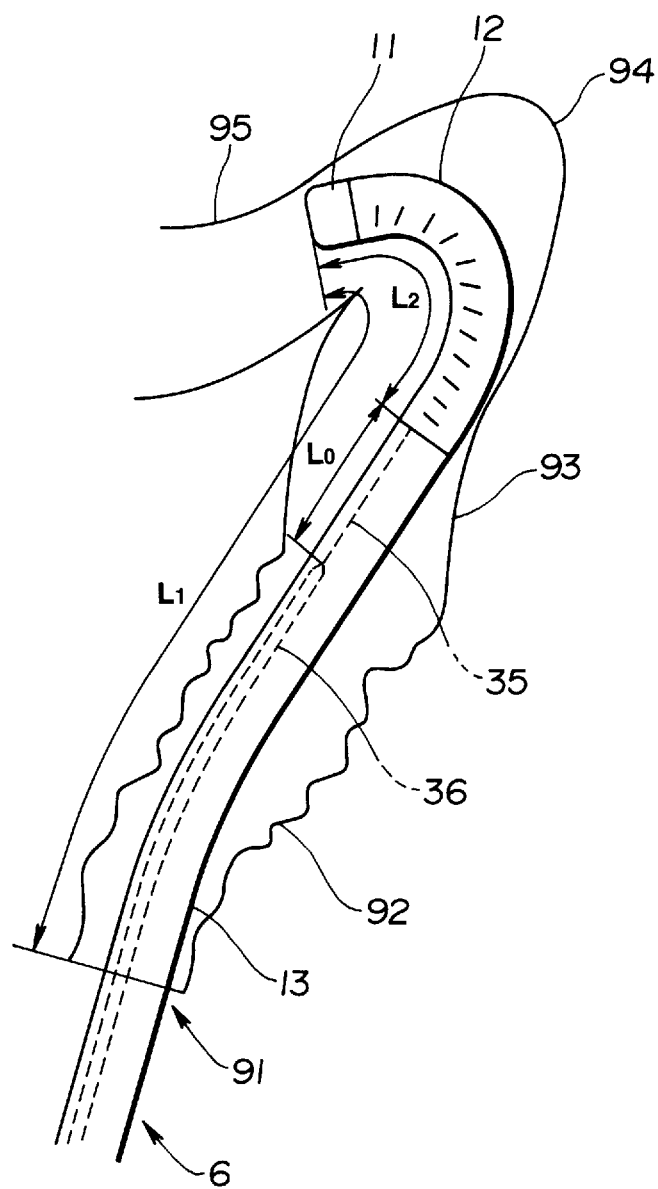

Referring to FIGS. 16 to 18, the relationship between the position of the distal end of the coil 36 of the hardness variation mechanism included in the soft part 13 and insertional smoothness will be described.

Inserting the insertion unit 6 into the splenic curvature 97 that is very sharply bent will be described in conjunction with FIG. 16.

As illustrated, the very sharply bent state of the splenic curvature 97 is a sharply bent state in which, for example, the inner wall 99 of the curvature is nearly folded. When an angle is used as a term "bending angle" to express the bent state, the bending angle is about 180°. At this time, since the splenic curvature 97 and its surroundings are locked in body walls, it may be difficult to forcibly alleviate the sharply bent state. In particular, when the folded portion of the inner wall 99 of the curvature is closely folded, it is quite difficult to alleviate the bent state.

In general, a recently available colonoscope has a bending portion 12 that can be bent by a maximum of 180°, and can therefore pass through a region that is bending about 180° as illustrated. When the bending portion 12 surmounts the bent region and advances to the ascending colon 96 as indicated with an alternate long and two short dashes line, the soft part 13 is located in the hepatic curvature 97. In other words, the distal side of the soft part 13 must be able to cope with the sharp bend of about 180° of the hepatic curvature 97. However, as mentioned above, when the colonoscope is inserted into a deep region, the coil 36 is hardened. When the distal end of the coil 36 is located at the distal end of the soft part 13, the soft part 13 may not be able to cope with the bent state of the hepatic curvature 97 or may have difficulty in coping with it.

In this embodiment, therefore, the soft part 13 has a soft area having a length L0 defined between the distal end of the soft part 13 and the position of the distal end of the coil 36.

The length L0 is large enough to cope with the hepatic curvature 97 bending about 180° or cope with a maximum angle by which the bending portion 12 can be bent. The condition for determining the length LO is that the length L0 is equal to or larger than a length L required for the soft part 13 to bend by 180° with a minimum radius of curvature or for the bending portion 12 to bend by a maximum angle.

How to determine the length L will be described.

As shown in FIG. 16, the distal end of the coil 36 does not reach the bending portion 12 but lies in a middle area of the soft part 13. In other words, a hardness invariable area whose hardness is not varied by a hardness variation means is formed in the distal side of the soft part 13. Specifically, the length from the distal end of the soft part 13 to the distal end of the coil 36 is the length L0.

As shown in FIG. 17A, the soft tube 37 serving as an armor of the soft part 13 has a three-ply structure of an armor resin 71, reticulate tube 72, and spiral tube 73. Herein, the width of each band of the spiral tube 73 shall be w, a gap between bands shall be c, the thickness of the armor resin 71 shall be t1, the thickness of the reticulate tube 72 shall be t2, and the outer diameter of the soft tube 37 shall be D.

As shown in FIG. 17B, when the soft tube 37 is bent, the adjoining bands of the spiral tube 73 abut on one another. Consequently, a radius of curvature with which the soft tube is bent is restricted.

A minimum radius of curvature to be attained when the soft tube 37 is bent in the smallest state shall be R, a minimum radius of curvature at a point on the spiral tube 73 shall be R1, and a minimum radius of curvature at a point on the center of the soft tube 37 shall be R2. A range defined by arrows linked by a dashed line in FIG. 17B is a range required for the soft tube 37 to bend by 180° or to become smallest. The range corresponds to the length L, which is shown in FIG. 17A, measured when the soft tube 37 is straightened. The lengths L0 and L have a relationship of L0≧L.

The above radii of curvatures have geometrically the following relationships:

$$L \approx n(w+c) \approx \pi R2 \approx \pi(R-D/2) \quad (1)$$

$$nw \approx \pi R1 \approx \pi(R+t1+t2) \quad (2)$$

where n is the number of turns of the band forming the spiral tube calculated within the length L.

Assuming, for example, that w is 3 mm, c is 1.2 mm, t1 is 0.4 mm, t2 is 0.3 mm, and D is 13 mm, L is approximately 64 mm according to the expressions (1) and (2).

The length L0 in the distal side of the soft part 13 defines an area whose length is equal to or larger than the length L shown in FIG. 17 and whose hardness is invariable and which is always soft. If the area is too long, when the endoscope is inserted into a deep region, obedience deteriorates. A length close to the length L is therefore preferable.

Moreover, as far as an endoscope of which portion having the coil 36 is always hard (hardness is invariable) from the beginning is concerned, the endoscope cannot cope with the tortuous sigmoid colon 92 shown in FIG. 6A. The structure is therefore unpreferable. In FIG. 6A, a portion extending from a position 30 cm away from the tip of the endoscope to a position 70 cm away from it is staying in the sigmoid colon 92. The portion is requested to be apparently softer than it is when the coil 36 is hardened.

Moreover, as shown in FIG. 18 that is an enlarged view of a region extending from the anus 91 to the splenic curvature 94 shown in FIG. 6B, assuming that a length from the distal-end surface of the endoscope 2 to a position near the anus 91 is L1, the length L1 is generally said to be about 40 cm. Assuming that a length from the distal end of the endoscope 2 to the tip of the soft part 13 is L2, the relationship of L0+L2<40 cm is established. At this time, since the length L1 is about 40 cm, even when the coil 36 extends proximally from a position 40 cm away from the tip of the endoscope, the distal end of the coil 36 does not lie in the large intestine. As seen from FIG. 18, the area with the length L1 hardly works on a living body (large intestine).

The distal end of the coil 36 should therefore be located at a position in the distal side beyond the position 40 cm away from the tip of the endoscope. Even in the state shown in FIG. 18, at least part of the large intestine can be held straightened.

The lengths L0 and L2 are determined so that the relationship of L0+L2<L1 (40 cm) will be established. At this time, needless to say, the relationship of L0≧L is still satisfied.

As mentioned above, since an always-soft area with the length L0 is defined between the distal end of the soft part 13 and the distal end of the coil 36, the endoscope can be used to examine such a case that, for example, the hepatic curvature is bent very sharply. Excellent insertional smoothness can be realized.

Referring to FIGS. 19 to 25, an example of the structure of an endoscope having a harness adjustment mechanism will be described.

Figure 19:
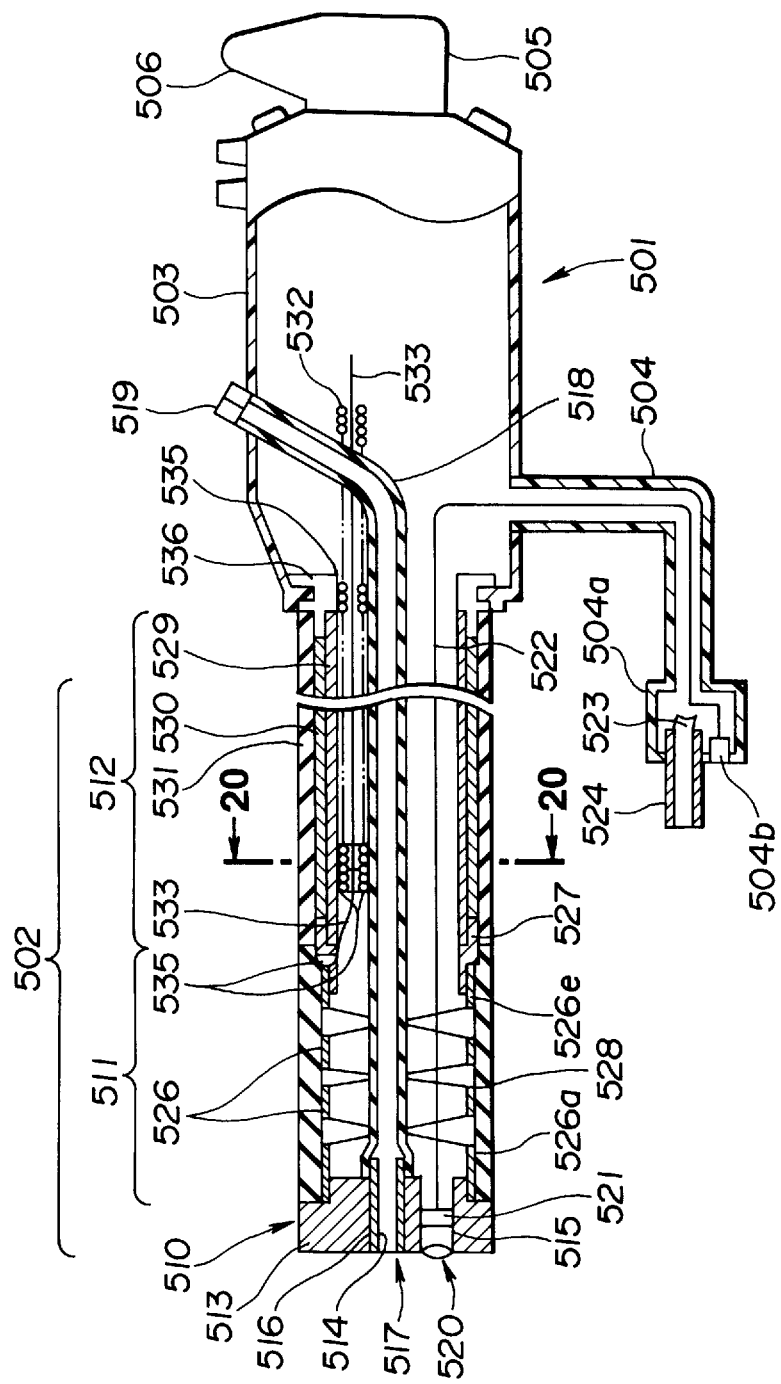

As shown in FIG. 19, an electronic endoscope (hereinafter endoscope) 501 of this embodiment comprises an elongated insertion unit 502 having flexibility, an operation unit 503 joined with the back end of the insertion unit 502, and a universal cable 504 extending from a flank of the operation unit 503. The universal cable 504 has a connector 504a to be linked to a light source apparatus for supplying illumination light which is an external apparatus of the endoscope 501.

The insertion unit 502 has a hard distal part 510 in the distal side thereof. A bending portion 511 that can be bent adjoins behind the distal part 510, and a soft part 512 that has flexibility and is like a soft tube is succeeding the bending portion 511.

The distal part 510 has a distal body 513 formed by shaping a hard member substantially like a cylinder. A forceps channel bore 514 and observation bore 515 are formed in the distal body 513 in parallel with the longitudinal direction of the insertion unit 502.

A connecting tube 516 is embedded in the forceps channel bore 514. A distal end of a forceps channel tube 518 forming a forceps channel 517 and having flexibility is coupled with the back-end portion of the connecting tube 516 jutting out of the back-end surface of the distal body 513. The forceps channel tube 518 is passed through the insertion unit 502, and routed into the operation unit 503, and has the back end thereof communicating with a treatment appliance insertion port 519 formed in the operation unit 503.

An objective lens system 520 is located at the distal end of the observation bore 515. A solid-state imaging device 521 is located on the image plane of the objective lens system 520. A signal cable 522 over which input and output signals are transmitted is linked to the solid-state imaging device 521. The signal cable 522 is passed through the insertion unit 502, and linked to an electrical contact 504b formed in the connector 504a by way of the operation unit 503 and universal cable 504.

The connector 504a has a light guide connector 524 along which illumination light emitted from a light source to illuminate a region to be observed propagates to fall on the end of a light guide 523 passing through the insertion unit 502. The light guide 523 passes through the universal cable 504, operation unit 503, and insertion unit 502, and has the distal end thereof located in a light guide bore (not shown) in the distal body 513.

A plurality of substantially annular joint pieces 526 are concatenated within the bending portion 511 in the longitudinal direction of the insertion unit 502 so that they can rotate freely. A first joint piece 526a located at the extremely distal end among the joint pieces 526 is engaged with and fixed to the back end of the distal body 513. A joint piece 526e located at the extremely back end is fitted in and fixed to the distal end of an annular linking tube 527 located at the distal end of the soft part 512. The bending portion 511 formed by concatenating the plurality of joint pieces 526 is bent vertically or laterally by manipulating a bending knob, which is not shown, formed on the operation unit 503.

An angle wire guide 541 (See FIG. 20) fixed to the back end of the distal body 513 and formed with a metallic coil pipe is held and locked in the linking tube 527. An angle wire 542 (See FIG. 20) that is towed or slackened by manipulating the bending knob formed on the operation unit 503 and is formed with a strand, extends through the angle wire guide 541. Specifically, when the bending knob is manipulated, the angle wire 542 is towed or slackened to bend the bending portion 511. The distal part 510 located in front of the bending portion 511 is thus oriented in a desired direction. The plurality of joint pieces 526 constituting the bending portion 511 are sheathed with a soft armor 528.

The soft part 512 is composed of a spiral tube 529, reticulate tube 530, and armor tube 531 in that order from the inside. A coil 532 forming a hardness variation mechanism for varying the hardness of the soft part 512 extends in the longitudinal direction on the inner wall of the spiral tube 529. A wire 533 for use in adjusting the hardness of the soft part 512 to desired hardness lies through the coil 532.

A middle point of the wire 533 is fixed firmly to the distal end of the coil 532 using a fixing member such as a brazing filler 535. The distal end of the wire 533 jutting out of the distal end of the coil 532 toward the distal end of the endoscope is fixed firmly to part of the linking tube 527 using the brazing filler 535 or the like. By the way, the proximal side of the coil 532 is fixed firmly to a back base 536 using the brazing filler 535 or the like.

In other words, the wire 533 is unfixed and movable with respect to the coil 532 except the middle point thereof that is fixed to the distal end of the coil 532 using the brazing filler 535.

The end of the wire 533 extending beyond the proximal end of the coil 532 is linked to a hardness adjustment knob 505 formed on the operation unit 503 and having the capabilities of a fixing means and manipulation mechanism. A finger rest 506 juts out of the hardness adjustment knob 505. The finger rest 506 is grabbed and manipulated in order to tow the wire 533. The coil 532 is then compressed, whereby the rigidity of the coil in a direction of bending improves. Thus, the hardness of the soft part 512 can be adjusted arbitrarily between a level at which the soft part is softened to the greatest extent and is not loaded and a level at which the soft part is hardened to the greatest extent and the wire 533 is towed to the greatest extent.

The finger rest 506 jutting out of the hardness adjustment knob 505 helps improve rotational smoothness and has the ability to notify an operator of the current hardness (compressed state) of the coil 532. Specifically, when the finger rest 506 is directed upwards in the drawing, the wire 533 is not towed. In this state, the coil 532 and soft part 512 are softest. By contrast, when the hardness adjustment knob 505 is rotated by, for example, 180° in order to direct the finger rest 506 downwards in the drawing, the wire 533 is towed to the greatest extent. The coil 532 and soft part 512 are hardest. When an operator discerns the angled state of the finger rest 506, he/she can judge the compressed state or hardness level of the coil 532 incorporated in the soft part 512.

Figure 20:
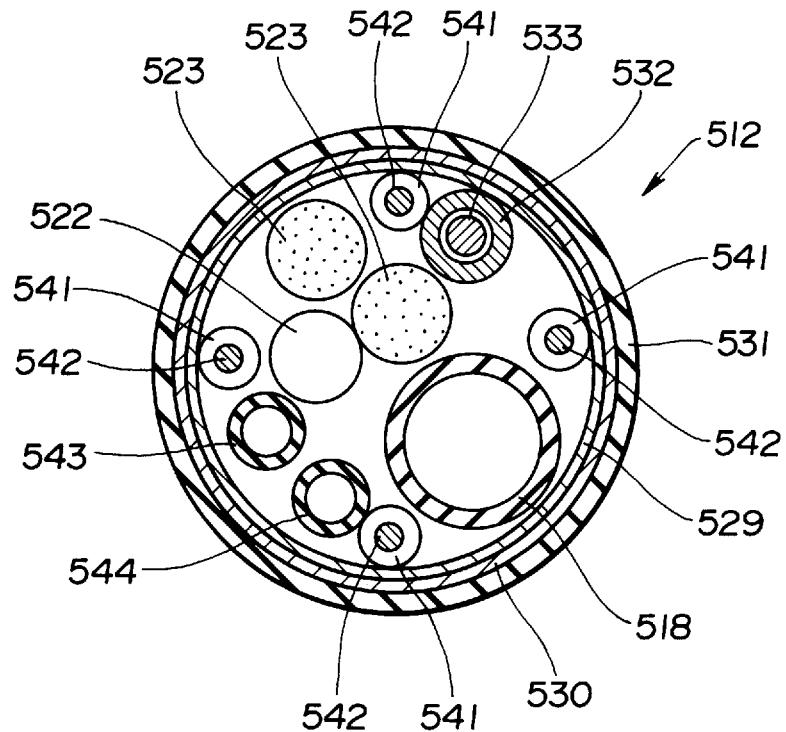

What is referred to as "upwards in FIG. 20" corresponds to "the Up direction of the endoscope 501." What is referred to as the Up direction of the endoscope 501 is a direction in which the distal part 510 is bent when the upward bending knob of the bending knob formed on the operation unit 503 is manipulated. The Up direction corresponds to the upper side (anti-gravity side) of the display screen of a monitor. As illustrated, the coil 532 and wire 533 are arranged in the Up direction of the endoscope 501. Reference numeral 543 denotes an aeration tube forming an aeration channel, and 544 denotes a perfusion tube forming a perfusion channel.

The distal ends of the tubes communicate with aeration and perfusion bores (not shown) in the distal body 513.

To begin with, the position of the coil 532 will be described more practically in relation to the longitudinal section of the soft part 512.

Figure 21:
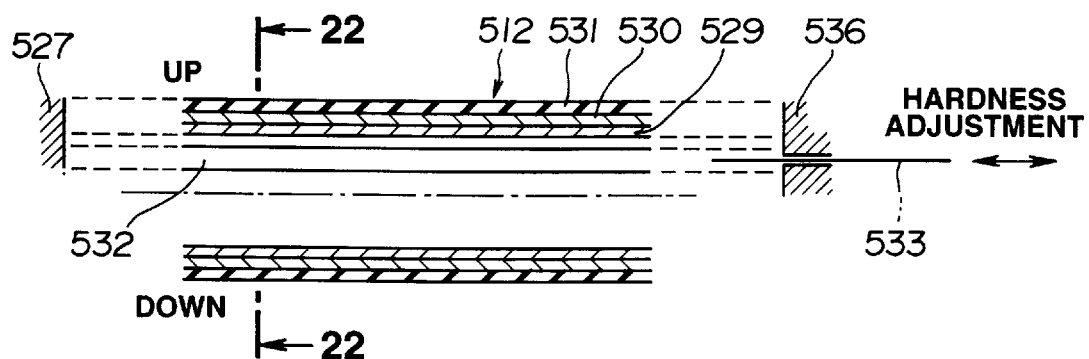

As shown in FIG. 21, the distal end of the coil 532 lying in the longitudinal direction of the inner wall of the soft part 512 of the endoscope 501 is, as mentioned above, fixed to the wire 533 using the brazing filler 535. The distal end of the wire 533 extending beyond the distal-end surface of the coil 532 is fixed to the linking tube 527. The proximal end of the coil 532 is fixed to the back base 536 using the brazing filler 535. The distal ends of the spiral tube 529, reticulate tube 530, and armor tube 531 constituting the soft part 512 are fixed firmly and unitedly to the distal end of the back base 536, whereby a tubular state is attained.

Figure 22:
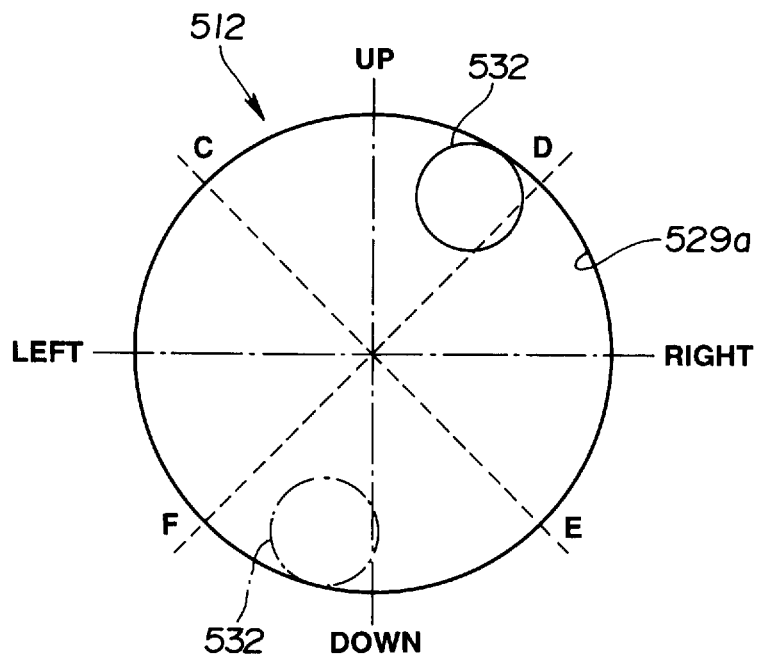

As shown in FIG. 22, when the cross section of the spiral tube 529 is quartered as indicated with dashed lines, the center position of the coil 532 placed on the inner wall surface of the spiral tube 529 included in the soft part 512 is found on a wall surface 529a in an Up-side area defined with Letters C and D or a Down-side area defined with Letters E and F.

When the tubular soft part 512 composed of the spiral tube 529, reticulate tube 530, and armor tube 531 is bent by itself, the portions of the spiral tube 529, reticulate tube 530, and armor tube 531 forming an inside arc of the bent area of the soft part 512, which is inside the center axis thereof, bend while contracting. The portions of the spiral tube 529, reticulate tube 530, and armor tube 531 forming an outside arc of the bent area of the soft part 512, which is outside the center axis thereof, bend while stretching.

Assume, for example, that the wire 533 lying through the soft part 512 is towed in order to compress and harden the coil 532, and the soft part 512 is bent in the Up direction in this state. The portions of the tube 529, reticulate tube 530, and armor tube 531 forming an inside arc of the bent area of the soft part on the Up side of the endoscope 501, which is inside the center axis thereof, attempt to contract. However, the hardened coil 532 located in the Up-side area and drawn with a solid line in FIG. 22 suppresses contraction of the portions of the tube 529, reticulate tube 530, and armor tube 531. The soft part 512 is bent in this state.

By the way, when the coil 532 is located on the Down side as indicated with a dot-dash line in FIG. 22, when the soft part 512 is bent in the Up direction, the portions of the tube 529, reticulate tube 530, and armor tube 531 forming an outside arc of the bent area of the soft part, which is outside the center axis thereof, attempt to stretch. However, since the coil 532 is located in the Down-side area and hardened, the stretch of the portions of the tube 529, reticulate tube 530, and armor tube 531 is suppressed. The soft part is bent in this state.

Next, the position of the coil 532 in the longitudinal direction of the soft part 512 and the operation thereof will be described particularly.

Figure 23:
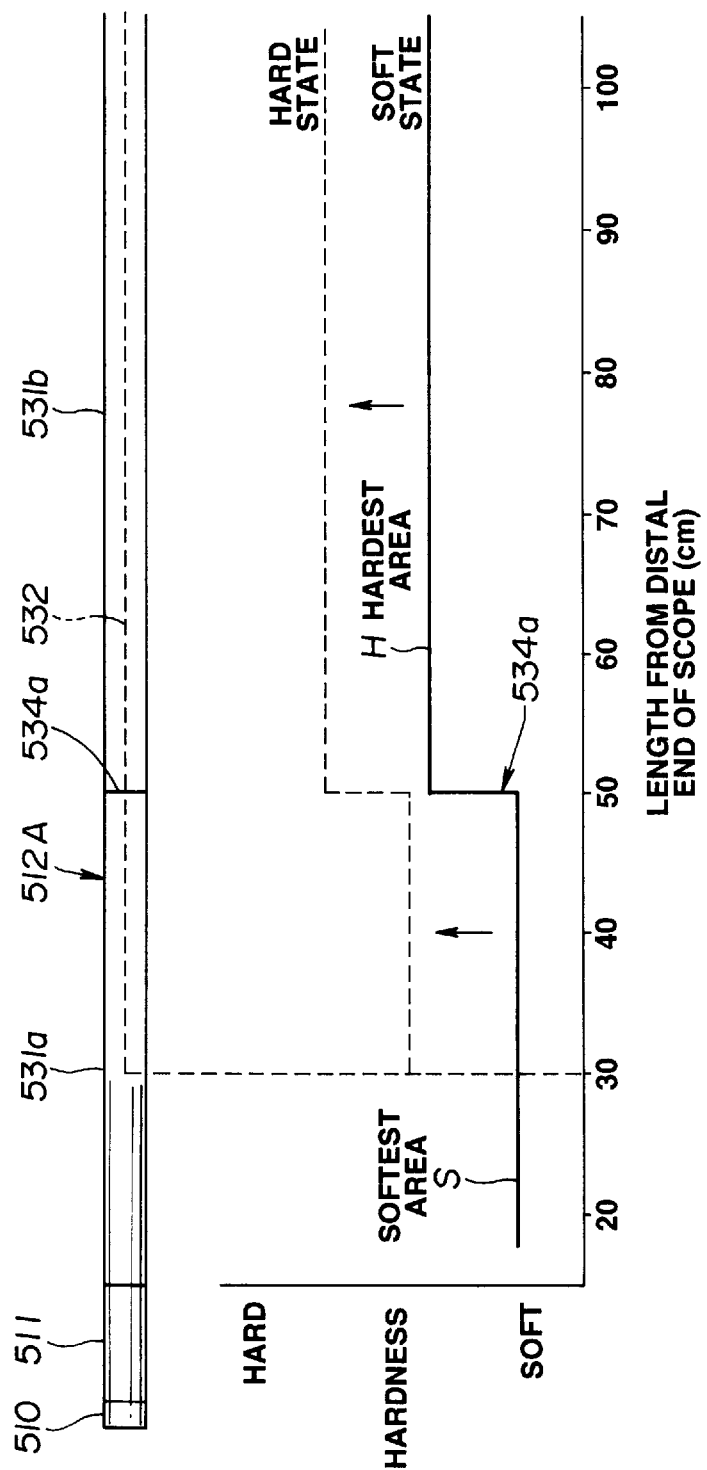
Figure 24:
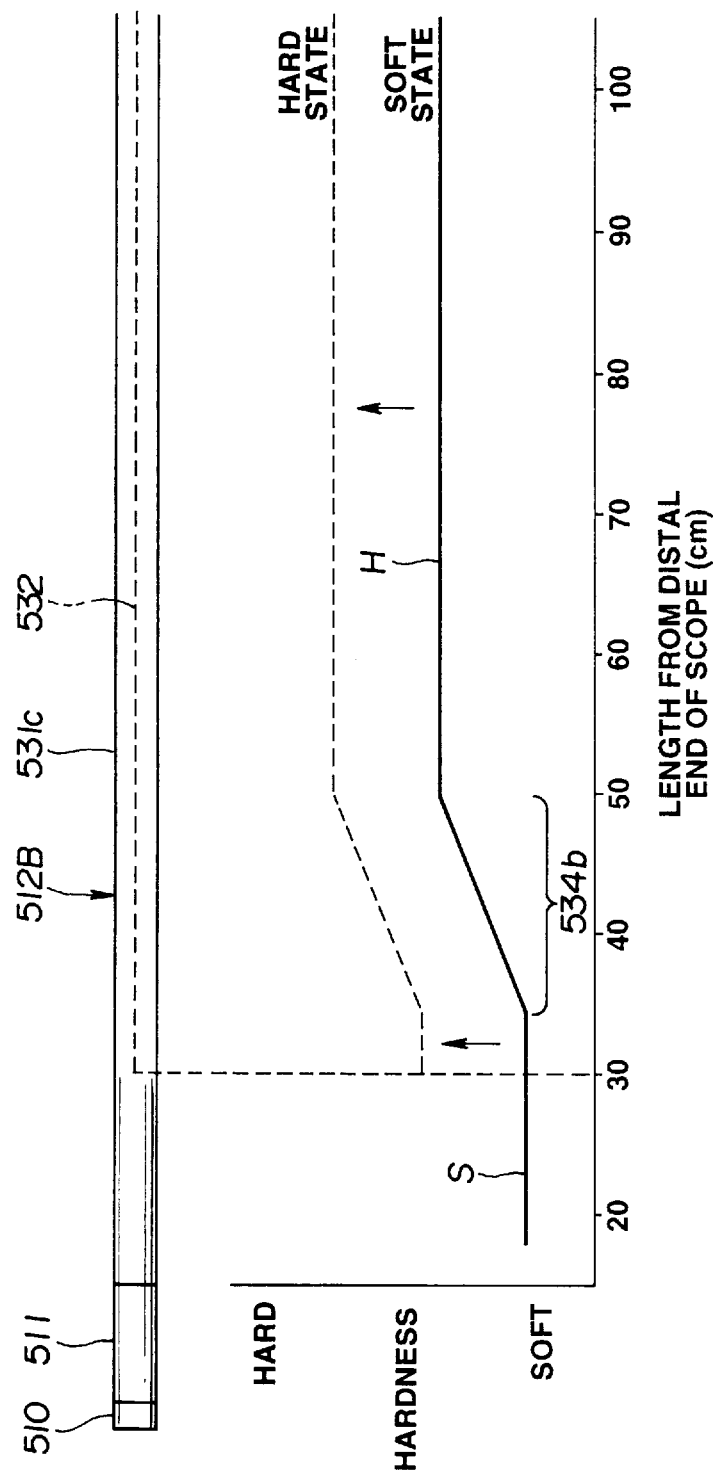

The soft part of the endoscope 501 of this embodiment is realized with, as shown in FIG. 23, a soft part 512A formed by linking two separate armor tubes 531a and 531b exhibiting different hardness levels, or, as shown in FIG. 24, a soft part 512B formed with an armor tube 531c having a hardness variation area 534b whose hardness varies gradually.

The soft part 512A shown in FIG. 23 is composed of a first soft part extending from the distal end of the soft part to a position about 50 cm away from the tip of the endoscope, and sheathed with a flexible soft armor tube 531a, and a second soft part extending from the position about 50 cm away from the tip of the endoscope to the proximal end of the soft part, and sheathed with a hard armor tube 531b that is soft but nevertheless slightly harder than the soft armor tube 531a. In other words, the hardness level of the proximal side of the soft part 512A beyond a hardness variation point 534a located at the position about 50 cm away from the tip of the endoscope is set to be higher than that of the distal side thereof.

The distal end of the coil 532 lying through the soft part 512A is located distally to the second soft part, that is, in the first soft part on the side of the distal part 510 beyond the hardness variation point 534a located at the position substantially 50 cm away from the tip of the endoscope.

As shown in FIG. 23, when the hardness variation mechanism is softened, that is, the wire 533 lying through the coil 532 is not towed, the characteristic balance in hardness of the soft part 512A is expressed with a solid line in FIG. 23. Moreover, when the wire 533 is towed to the greatest extent and the coil 532 is compressed to the greatest extent, the characteristic balance in hardness of the soft part 512A is expressed with a dashed line in FIG. 23. In short, when the wire 533 is towed properly, the hardness level of the soft part 512A varies within a range defined by the solid line and dashed line.

Moreover, since the distal end of the coil 532 is not extending to an area distal to a position 30 cm away from the tip of the endoscope, the hardness of the area of the first soft part extending from the distal end of the soft part to the position 30 cm way from the tip of the endoscope cannot be adjusted. Moreover, a distal side exhibiting the lowest hardness level indicated with the solid line shall be a softest area S, and a proximal side exhibiting the highest hardness level indicated with the solid line shall be a hard area H.

The soft part 512B shown in FIG. 24 is formed with the armor tube 531c having a hardness variation area 534b which extends from a position about 34 cm away from the tip of the endoscope to the position about 50 cm away from it and whose hardness level varies gradually from a level at which the soft part is softened to a level at which the soft part is hardened. In other words, an area of the soft part 512B extending from the distal end thereof to the position about 34 cm away from the tip of the endoscope serves as a first soft part that is the softest area S. An area thereof extending from the position 34 cm away from the tip of the endoscope to a position about 50 cm away from it is the hardness variation area 534b whose hardness varies gradually from the level at which the soft part is softened to the level at which the soft part is hardened. An area extending from the position 50 cm away from the tip of the endoscope to the proximal end of the soft part is a second soft part that is the hard area H.

The distal end of the coil 532 lying through the soft part 512B is located in the first soft part on the side of the distal part 510 beyond the hardness variation area 534b starting at the position substantially 34 cm away from the tip of the endoscope.

The solid line in FIG. 24 expresses the characteristic balance in hardness of the soft part 512 attained when the wire 533 lying through the coil 532 is not towed. The dashed line in FIG. 24 expresses the characteristic balance in hardness hardening the soft part 512 by towing the wire 533 to the greatest extent and compressing the coil 532 to the greatest extent. In the illustrated endoscope, the hardness of the distal side beyond the hardness variation area 534b extending from the position about 34 cm away from the tip of the endoscope to the position about 50 cm away from it can be varied.

The hardness variation area 534b is manufactured by mixing a hard resin material in a soft resin material to be made into a distal area in the course of manufacturing, increasing the ratio of the hard resin material to the soft resin material, and thus applying the mixture to the reticulate tube 530.

The operation of the endoscope 501 having the foregoing components will be described with reference to FIG. 25.

Figure 25A:
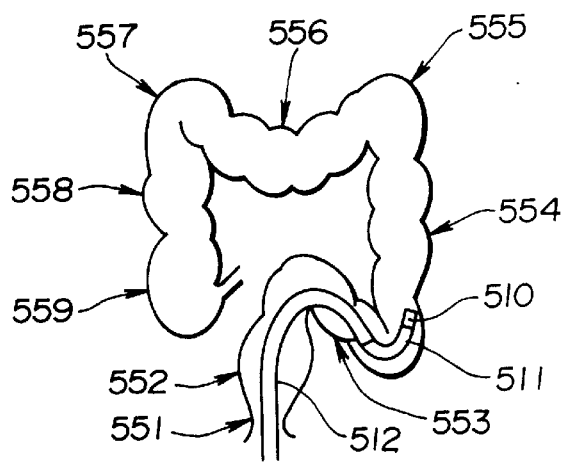

To begin with, the insertion unit 502 of the endoscope 501 is, as shown in FIG. 25A, inserted through the anus 551, passed through the rectum 552, and thrust forward in the tortuous sigmoid colon 553. At this time, the soft part 512A is softened. The area from the distal end of the soft part to the position about 50 cm away from the tip of the endoscope is therefore soft. The soft part is therefore inserted while looping in line with the bending shape of the sigmoid colon 553 without giving a patient any pain.

Some operators may adopt such a procedure that the wire 533 is manipulated in order to compress the coil 532 gradually so that the soft part 512 will not be looped too greatly in the sigmoid colon 553 but can be straightened and inserted while causing the sigmoid colon 553 to collapse and contract. In this case, the coil 532 is compressed in order to set the soft part 512A to an operator's desired hardness level. Thus, a delicate manipulation such as a push and pull or a twist is conveyed to the distal end of the endoscope. The endoscope is then inserted smoothly.

Figure 25B:
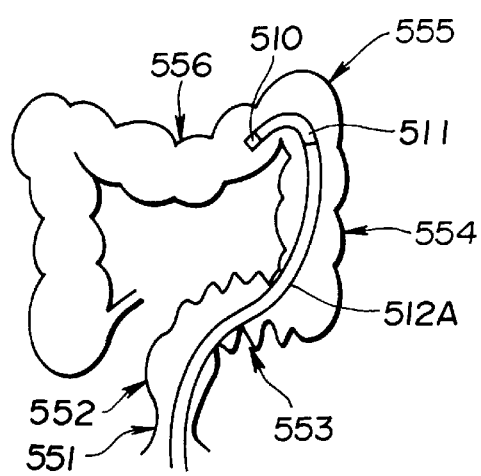

Next, when the distal part 510 of the endoscope 501 overpasses the sigmoid colon 553 and reaches the descending colon 554 or a region near the splenic curvature 555, the soft part 512A is, as shown in FIG. 25B, pulled while being twisted in order to resolve the loop, and thus straightened as perfectly as possible. This causes the sigmoid colon 553 to collapse. Moreover, when the soft part 512A is softened, the wire 533 is manipulated properly in order to set the soft part to a desired hardness level. The distal part 510 is thus inserted smoothly into the transverse colon 556, hepatic curvature 557, ascending colon 558, and cecum 559 because the manipulation is conveyed sensitively to the distal part 510.

Figure 25C:
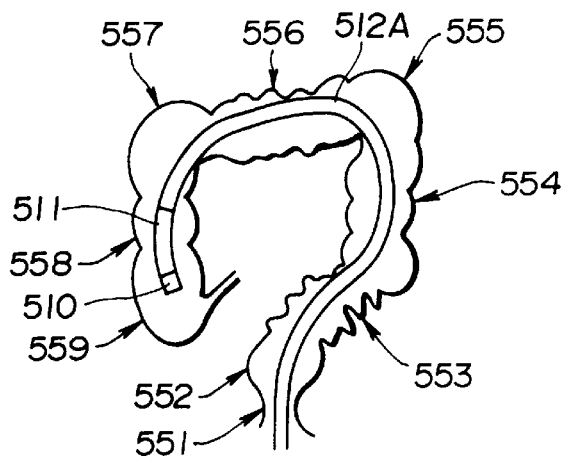

The shapes of the transverse colon 556 and hepatic curvature 557 may differ from patient to patient. For example, when a patient has the transverse colon 556 and hepatic curvature 557 whose shapes are not so complex, the transverse colon 556 is collapsed by manipulating the endoscope proximally so that the endoscope can pass through the hepatic curvature 557 without looping in the transverse colon 556. The endoscope is, as shown in FIG. 25C, substantially straightened, whereby the distal part 510 can be routed to the cecum 559. Thus, in the case of the patient having the transverse colon 556 and hepatic curvature 557 whose shapes are not so complex, the distal part 510 can be inserted swiftly to the cecum merely by adjusting the soft part 512A according to desired hardness.

Figure 25D:
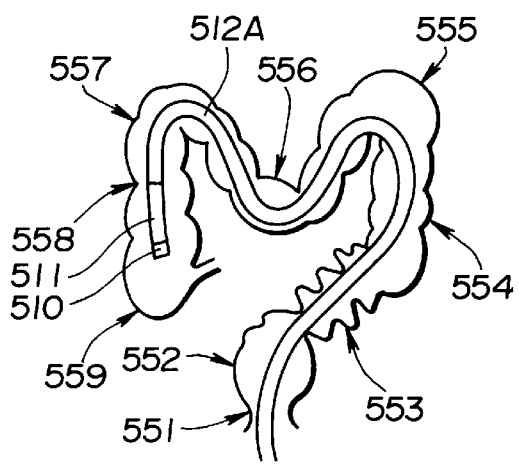

However, in the case of a patient whose transverse colon 556 is very long or shaped complexly, an operator may find it difficult to collapse the transverse colon 556 by manipulating the endoscope proximally and fail to do it. In this case, the endoscope is looped and thrust forward in the transverse colon 556 by manipulating it proximally. The distal part 510 is thus inserted while being slided over the intestinal wall. According to this inserting procedure, when the soft part 512 is hardened, the soft part may not be advanced in line with the tortuous shapes of the transverse colon 556 and hepatic curvature 557. There is the fear of deteriorating insertional smoothness. The wire 533 is therefore manipulated properly in order to soften the soft part 512A. The endoscope is thrust forward while, as shown in FIG. 25D, the first soft part in the distal side is advanced in line with the shapes of the transverse colon 556 and hepatic curvature 557.

When one operator inserts an endoscope into the large intestine, he/she usually bends the endoscope in the Up direction so as to pass the endoscope through a tortuous region in the large intestine. In other words, the endoscope is hardly bent in the Down, Left, and Right directions. A direction of insertion is determined by bending the endoscope in the Up direction and twisting the soft part 512. The soft part 512 is passed through the tortuous regions in the large intestine while bending in the Up direction.

As shown in FIGS. 23 and 24, even when the soft part is softened, the proximal side of the soft part beyond the position 50 cm away from the tip of the endoscope is set to a higher hardness level than the distal side thereof. As shown in FIG. 25B, therefore, it is prevented that the contracted sigmoid colon 553 deflects and loops again and a manipulation made proximally is not conveyed to the distal part 510.

Furthermore, the position of the distal end of the coil 532 is set near the distal side of the soft part 512A or 512B. This leads to improved obedience. Even when an endoscope is inserted according to the inserting procedure shown in FIG. 25C, the endoscope can be thrust forward while the insertion unit 502 is bent in line with the bends of the transverse colon 556 and hepatic curvature 557. The distal end of the coil 532 is located at the position 30 cm away from the tip of the endoscope and the area extending from the distal end of the soft part to the position 30 cm away from the tip of the endoscope is left as the softest area S so that the endoscope can be thrust forward in line with the bends without being looped.

As mentioned above, since the distal end of a coil is located in the softest area of the soft part, the hardness of at least part of the softest area can be adjusted to be varied. This leads to the greatly improved obedience of the insertion unit of an endoscope. The endoscope can be coped with various inserting procedures adopted by operators. Moreover, when the endoscope is inserted as shown in FIG. 25C, if the distal end of the coil is located at a position proximal to a position 50 cm away from the tip of the endoscope, since the hardness of the softest area S extending from the distal end of the soft part to the position 50 cm away from the tip of the endoscope cannot be varied, a manipulation made proximally cannot be conveyed to the distal part. This drawback can be overcome.

Moreover, since a coil is located in the longitudinal direction of the inner wall of a spiral tube included in a soft part in the Up-side or Down-side area, desired bending hardness can be produced by minimizing a tractive force required for towing a hardness adjustment wire or shortening a distance by which a movement is made. Since the coil is placed on the inner wall, the rigidity of the soft part against bending in the Up or Down direction increases. The hardness of the soft part can be set to a higher level without the necessity of imposing a large load. This obviates the need of largely expanding a range of levels of the adjustable hardness of a coil unit. A load to be imposed on the coil and wire diminishes and the durability of the coil and wire improves.

Furthermore, since the position of the distal end of the coil is set distally to a hardness variation point or hardness variation area, it can be prevented that the soft part is bent sharply because of the abrupt variation of hardness at the hardness variation point or in the hardness variation area. The soft part can therefore be inserted into a body cavity while being bent smoothly.

Figure 26:
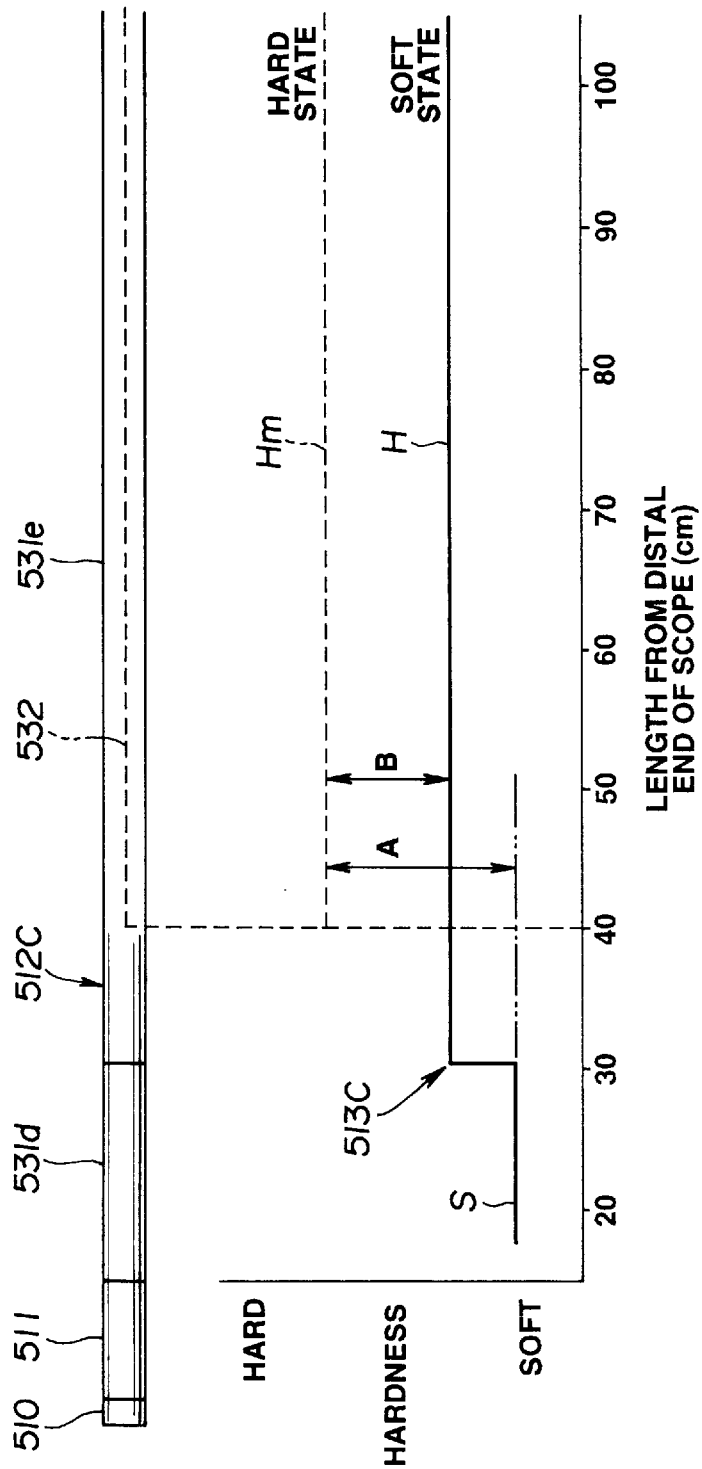
Figure 27:
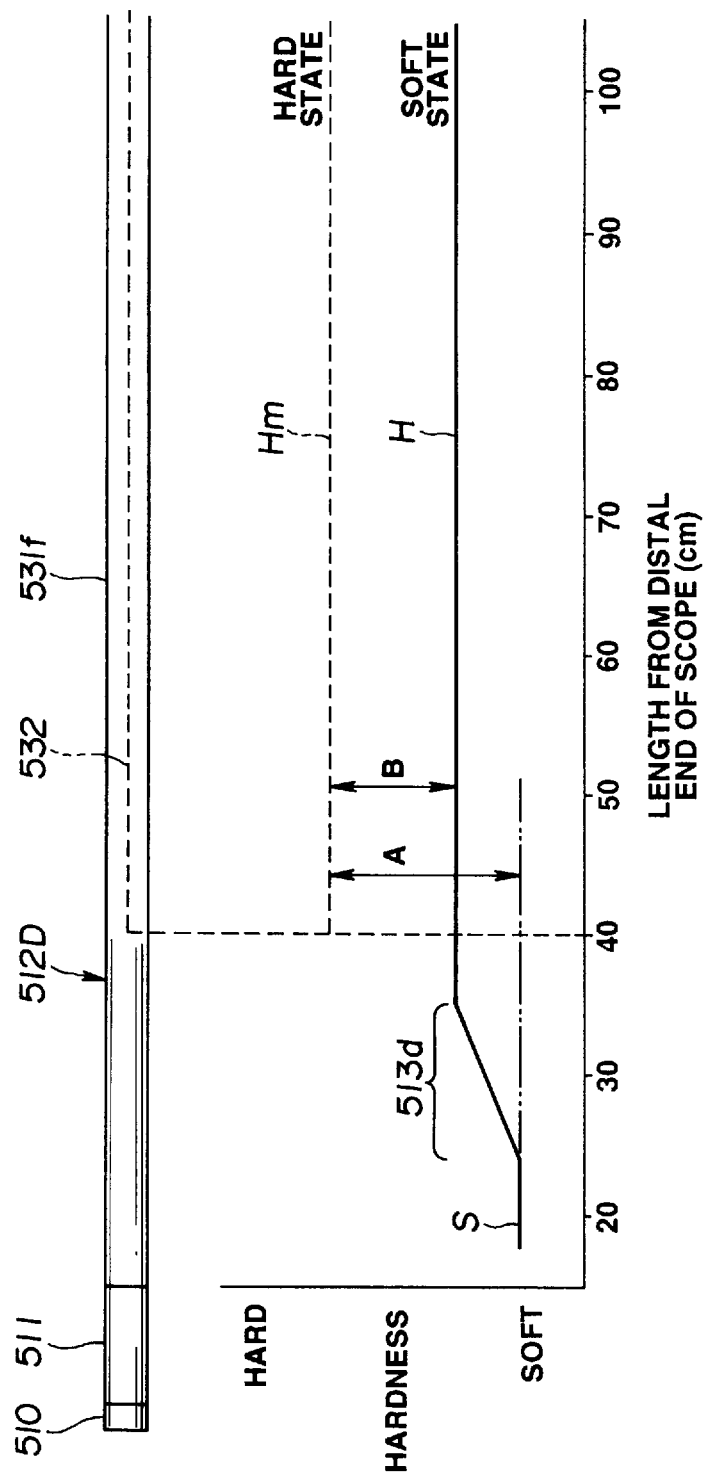

Referring to FIGS. 26 to 28, another example of the structure of an endoscope having a hardness adjustment mechanism will be described.

The soft part of the endoscope 501 of this embodiment is realized with, as shown in FIG. 26, a soft part 512C formed by linking two separate armor tubes 531d and 531e exhibiting different hardness levels, and having the junction between the tubes as a hardness variation point 513c, or, as shown in FIG. 27, a soft part 512D formed with an armor tube 531f having a hardness variation area 513d whose hardness varies gradually and continuously in a direction from the distal side to proximal side.

The soft part 512C shown in FIG. 26 is composed of a first soft part ending at a position about 30 cm away from the tip of the endoscope and sheathed with a soft armor tube 531d whose hardness is low, and a second soft part extending proximally from the position 30 cm away from the tip of the endoscope and sheathed with a soft armor tube 531e that is soft but harder than the soft armor tube 531d. In short, the proximal side of the soft part 512C bordered by the hardness variation point 513c located at the position 30 cm away from the tip of the endoscope exhibits a higher hardness level than the distal side thereof.

The distal end of the coil 532 incorporated in the soft part 512C is located at a position about 40 cm away from the tip of the endoscope within the second soft part.

As shown in FIG. 26, when the coil 532 is softened or unloaded, that is, when the wire 533 lying through the coil 532 is not towed, the characteristic balance in hardness of the soft part 512C is expressed with a solid line. By contrast, when the wire 533 is towed to the greatest extent and the coil 532 is loaded and compressed to the greatest extent, the characteristic balance in hardness of the soft part 512C is expressed with a dashed line and defines a hardest area Hm. In other words, when the wire 533 is towed properly, the hardness level of the soft part 512C varies within a range defined by the solid line and dashed line.

Since the distal end of the coil 532 does not extend distally beyond the position 40 cm away from the tip of the endoscope, the hardness levels of the first soft part and of the portion of the second soft part beyond the position 40 cm away from the tip of the endoscope do not vary. Moreover, the distal side exhibiting the lowest hardness level indicated with the solid line shall be the softest area S, and the proximal side exhibiting the highest hardness level shall be the hard area H.

On the other hand, the soft part 512D shown in FIG. 27 is formed with an armor tube 531f extending from a position about 25 cm away from the tip of the endoscope to a position about 35 cm from it and having a hardness variation area 513d whose hardness level varies gradually in a direction from the softest area S to hard area H. An area of the soft part 512D ending at the position about 25 cm away from the tip of the endoscope is the softest area S and serves as a first soft part. An area of the soft part 512D extending from the position about 25 cm away from the tip of the endoscope to the position about 35 cm away from it is the hardness variation area 513d whose hardness varies from the hardness of the softest area S to that of the hard area H. An area of the soft part 512D extending proximally from the position about 35 cm away from the tip of the endoscope is the hard area H and serves as a second soft part.

The distal end of the coil 532 incorporated in the soft part 512D is located proximally to the hardness variation area 513d at a position about 40 cm away from the tip of the endoscope within the second soft part.

A solid line in FIG. 27 indicates the hardness level of the soft part 512D attained when the wire 533 lying through the coil 532 is not towed. A dashed line in the drawing expresses the characteristic balance in hardness of the soft part 512D attained when the wire 533 is towed to the greatest extent and the coil 532 is compressed to the greatest extent. In this endoscope, the hardness level of the proximal side of the soft part beyond the hardness variation area 513d extending from the position about 25 cm away from the tip of the endoscope to the position about 35 cm away from it can be varied. The hardness variation area 513d of the armor tube 531f is manufactured by mixing a hard resin material in a soft resin material to be made into the distal side of the armor tube in the course of manufacturing, increasing the ratio of the hard resin material to the soft resin material, and thus applying the mixture to the reticulate tube 530.

The operation of the endoscope 501 having the foregoing structure will be described with reference to FIG. 28.

Figure 28A:
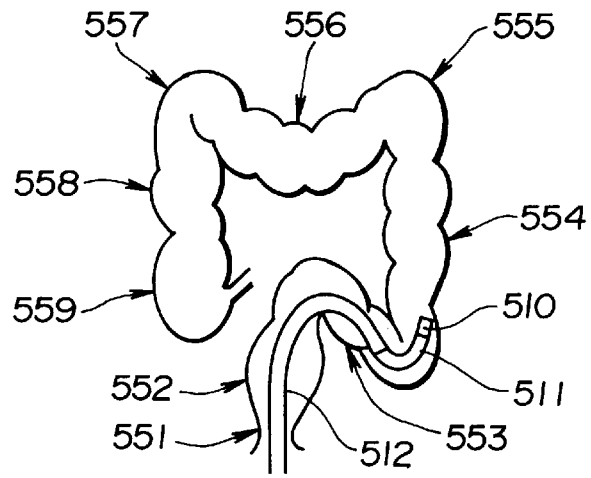

To begin with, the insertion unit 502 of the endoscope 501 is, as shown in FIG. 28A, inserted through the anus 551, passed through the rectum 552, and inserted into the tortuous sigmoid colon 553. At this time, the soft part 512 is softened and inserted while being looped in line with the bending shape of the sigmoid colon 553.

Figure 28B:
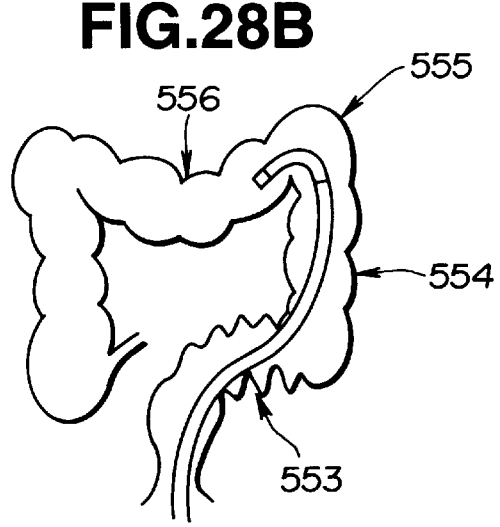

When the distal part 510 of the endoscope 501 overpasses the sigmoid colon 553 and reaches the descending colon 554 or a region near the splenic curvature 555, the soft part 512 is, as shown in FIG. 28B, pulled while being twisted by manipulating the endoscope proximally. The soft part 512 is thus released from the looped state set in the sigmoid colon 553, and in turn straightened. At this time, the sigmoid colon 553 is substantially straightened together with the soft part 512 while being collapsed.

By rotating the hardness adjustment knob 505 properly in order to compress the wire 533, the hardness of the soft part 512 is changed to a desired level. A push and pull or a twist made proximally is conveyed sensitively to the distal part 510. This causes the distal part 510 to overpass the transverse colon 556, hepatic curvature 557, and ascending colon 558 and smoothly reach the cecum 559.

The shapes of the transverse colon 556 and hepatic curvature 557 may differ from patient to patient. For example, when the transverse colon 556 and hepatic curvature 557 are bending sharply, even if the soft part 512 is hardened, the soft part 512 is not hardened over the whole length thereof but the area ending at the position about 30 cm away from the tip of the endoscope is softened so that the soft part 512 can clear the sharply-bent shapes.

What is concerned about most in the procedure for inserting the endoscope 501 into a deep region in the large intestine is that the sigmoid colon 553 and soft part 512 straightened as shown in FIG. 28B should not be deflected as shown in FIG. 28A. Supposing the sigmoid colon and soft part in the state shown in FIG. 28B are deflected again, when the distal part 510 is passed through the transverse colon 556 or hepatic curvature 557, a manipulation made proximally can hardly be conveyed to the distal part 510.

For preventing the soft part from looping again in the sigmoid colon 553, the proximal side of the soft part 512 beyond an intermediate position thereof may be hardened very greatly from the beginning for insertion. However, while the soft part is looped largely in the sigmoid colon 553, when the distal part 510 is passed through the sigmoid colon 553 and routed to the descending colon 554 and splenic curvature 555, a portion of the insertion unit 502 of 90 cm to 1 m long from the distal end thereof stays in a living body.

Figure 28C:
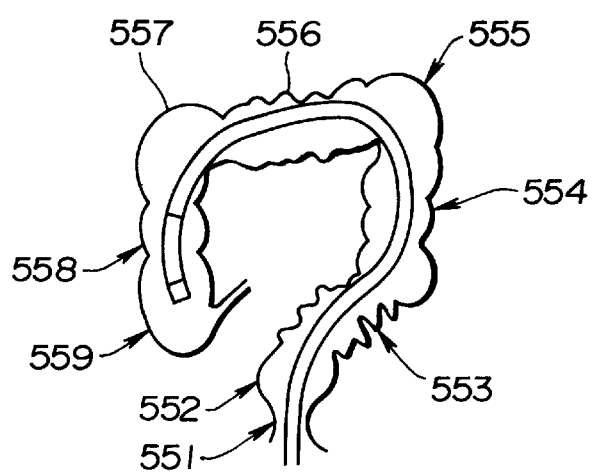

As mentioned above, when the endoscope 501 is inserted while being looped, the soft part 512 that is made softer can be inserted more smoothly. If the soft part 512 is rather hard, it often causes a patient's pain. Assuming that a half of the soft part 512 of, for example, 90 cm long from the border of the distal part is hardened so as not to be deflected in the sigmoid colon 553, it becomes impossible to pass the distal part through the sigmoid colon 553 while looping the soft part. Furthermore, as shown in FIGS. 28B and 28C, when the distal part 510 reaches the cecum 559 with the soft part hardly looped, a portion of the insertion unit 502 staying in a living body is about 90 cm long from the distal-end surface of the endoscope. At this time, even if the proximal side of the soft part beyond the position 90 cm away from the distal-end surface of the endoscope is hardened very greatly, while the insertion unit is passed through the transverse colon 556 and hepatic curvature 557, the hardened proximal side of the soft part hardly proves useful.

However, in this embodiment, the hardness of the soft part 512 is variable. Specifically, when the insertion unit 502 of the endoscope 501 is inserted into, for example, the cecum through the anus, the soft part 512 remains softened until it passes through the sigmoid colon 553. After the soft part passes through the sigmoid colon 553, the hardness adjustment knob 505 is rotated in order to set the hardness of the soft part 512 to a rather high level. Then, the soft part is inserted into a deep region in the large intestine.

At this time, the hardness of the hardest area Hm of the soft part 512 indicated with a dashed line in FIG. 26 or FIG. 27 is high enough to prevent the soft part from looping again in the sigmoid colon 553. A difference between the hardness level of the hardest area Hm indicated with the dashed line and the hardness level of the softest-state area S indicated with a solid line is indicated with an arrow A in the drawing. However, the soft part 512C or 512D has the hardness variation point 513c or hardness variation area 513d in the middle thereof. The hardness level of the soft part 512C or 512D therefore varies in three steps, that is, from the hardness level of the softest area S indicated with the solid line, that of the hard area H indicated with the solid line, and that of the hardness area Hm indicated with the dashed line in that order from the distal-side surface. In other words, when the hardness adjustment knob 505 is rotated, since the soft part 512 of this embodiment has the hard area H, of which hardness level is indicated with the solid line, between the softest area S and hardest area Hm, a difference the hardness level of the hardest area Hm is a difference indicated with an arrow B and smaller than the difference in hardness level between the hardest area Hm and softest area S.

As mentioned above, the distal end of the coil is located in the second soft part of the soft part. When the hardness adjustment knob is rotated in order to tow the hardness adjustment wire and thus compress the coil, the hardness of the soft part varies in three steps from the hardness of the softest area S through that of the hard area H to that of the hardest area Hm. Thus, the magnitude of variation of hardness can be reduced. Consequently, when the hardness adjustment knob is manipulated in order to compress a pipe, since the hardness of the soft part varies stepwise, the sharp bending of the soft part occurring when the hardness varies sharply at the hardness variation point or in the hardness variation area can be prevented. Eventually, it can be prevented that the contents are damaged or insertional smoothness deteriorates.

When a comparison is made between the soft part 512C having the hardness variation point 513c shown in FIG. 26 and the soft part 512D having the hardness variation area 513d shown in FIG. 27, the insertion unit 502 whose soft part 512D has the hardness variation area 513d can bend in a smoother form than the insertion unit 502 whose soft part 512C has the hardness variation point 513c.

Figure 29:
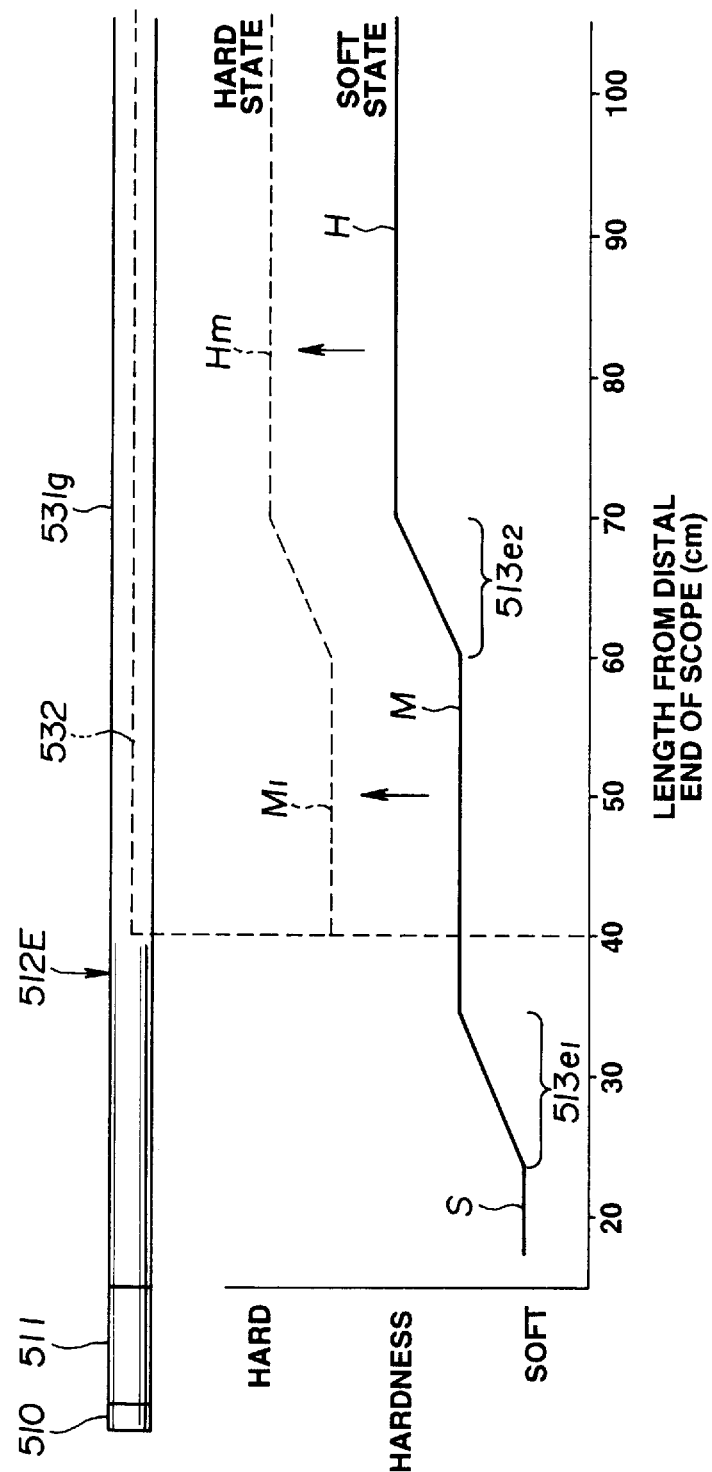
FIGS. 29 and 30 are explanatory diagrams showing other examples of the structure of an endoscope having a hardness adjustment mechanism and employed in an endoscope system in accordance with the present invention.
Figure 30:
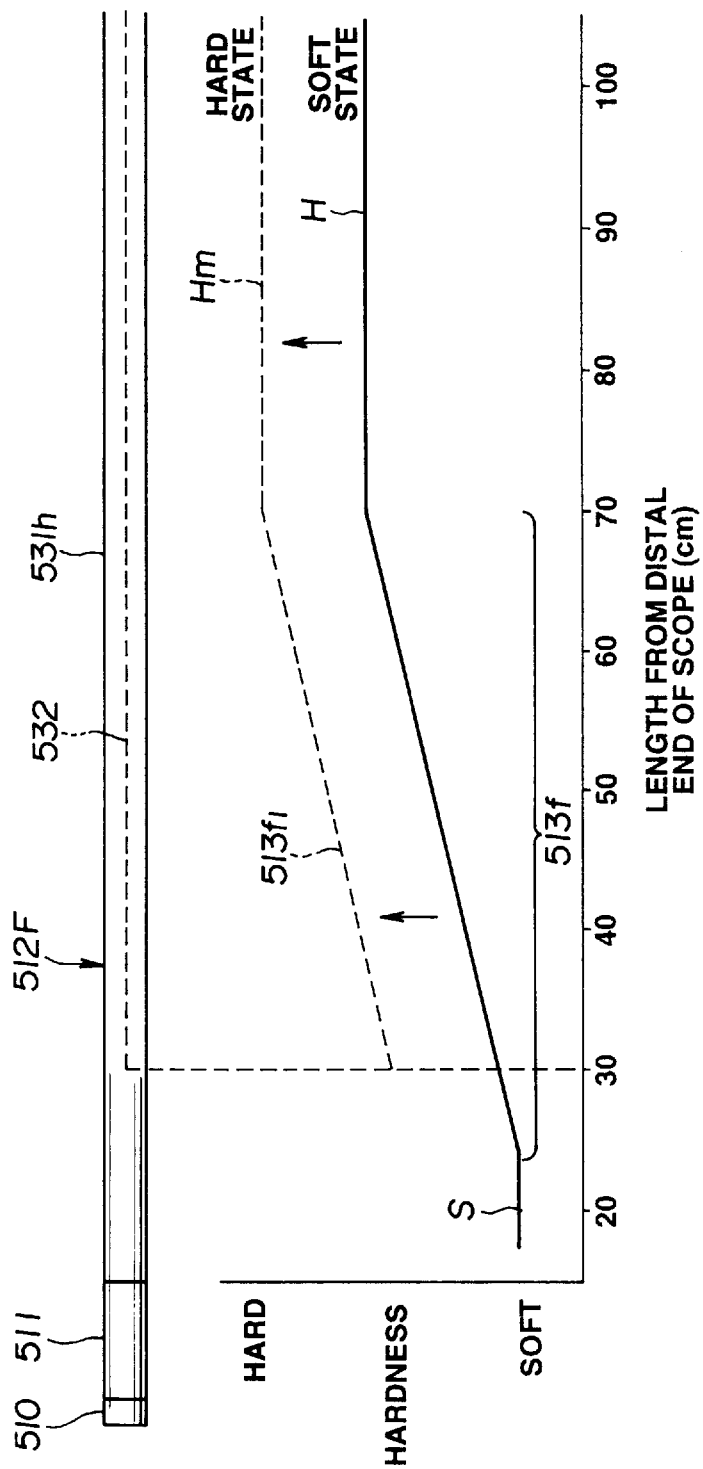

Referring to FIGS. 29 and 30, still other examples of the structure of an endoscope having a hardness adjustment mechanism will be described.

In this embodiment, the number of variation steps to be set between the softest area S to hardest area Hm of the soft part is made larger than that in the aforesaid embodiment. Thus, the sharp bending of a portion of the soft part near the hardness variation area thereof is prevented.

As shown in FIG. 29, a soft part 512E has an intermediate-hardness area M, of which hardness is of an intermediate level between the hardness levels of the softest area S and hard area H, between the softest area S and hard area H. In other words, the soft part 512E is formed with an armor tube 531g having a first hardness variation area 513e1, of which hardness varies continuously, between the intermediate-hardness area M and softest area S, and a second hardness variation area 513e2, of which hardness varies continuously, between the intermediate-hardness area M and hard area H. The hardness of the soft part 512E is thus varied in three steps. The distal end of the coil 532 incorporated in the soft part 512E is located at a position 40 cm away from the tip of the endoscope within the intermediate-hardness area M.

When the coil 532 is compressed to the greatest extent, the hardness of the soft part 512E varies in four steps from the hardness of the softest area S through the hardness of the intermediate-hardness area M indicated with a solid line and that of the intermediate-hardness area M1 indicated with a dashed line to the hardness of the hardest area Hm in that order from the distal end of the soft part. Consequently, the magnitude of variation of the hardness level of the soft part becomes smaller than that in the aforesaid embodiment.

On the other hand, in FIG. 30, a soft part 512F is formed with an armor tube 531h having a wide hardness variation area 513f, of which length in the longitudinal direction is as long as substantially 45 cm, between the softest area S and hard area H. The hardness of the soft part 512F is varied continuously within this rather long area. The distal end of the coil 532 incorporated in the soft part 512F is located at an intermediate position 30 cm away from the tip of the endoscope within the wide hardness variation area 513f.

When the coil 532 is compressed to the greatest extent, therefore, as illustrated, the hardness of the soft part 512F varies stepwise from the hardness of the softest area S indicated with a solid line through the hardness of the wide hardness variation area 513f indicated with a solid line and the hardness of a wide hardness variation area 513f1 indicated with a dashed line to the hardness of the hardest area Hm indicated with the dashed line in that order from the distal end of the soft part. In this embodiment, in particular, the wide hardness variation area 513f1 whose hardness is indicated with the dashed line is made so wide that the hardness level can be varied continuously. The magnitude of variation of the hardness level of the soft part is further reduced, that is to say, the hardness of the soft part varies smoothly.

The proximal side of the soft part 512E or 512F beyond a position about 70 cm away from the tip of the endoscope is defined as the hardest area Hm. This specification of the soft part 512E or 512F is suitable for such an inserting procedure that the endoscope is passed through the transverse colon 556 with the transverse colon 556 deflected to some extent, because the hardness of the distal side beyond the position about 70 cm away from the tip of the endoscope is lower than that of the proximal side.

For such an inserting procedure that an endoscope is passed through the transverse colon 556 with the transverse colon 556 collapsed in the middle thereof, as described in relation to the aforesaid embodiment, a specification according to which the hardness of the proximal side beyond a position about 40 cm away from the tip of the endoscope is set to the highest level so that a manipulation made proximally can be conveyed to the distal part more efficiently is suitable.

Moreover, when, for example, three separate armor tubes exhibiting different hardness levels are concatenated in an orderly fashion by placing the softest one adjacently to the distal part in order to vary the hardness level of the soft part 512E stepwise, the same operation as the operation of the armor tube 531g can be exerted.

Furthermore, the position of the distal end of the coil 532 is a bit different between the soft part 512E shown in FIG. 29 and the soft part 512F shown in FIG. 30. This is intended to cope with a difference in inserting procedure or inserting technique of one operator from another. FIGS. 29 and 30 show examples meeting operators' likes. In general, when the hard part of an endoscope is located closer to the distal end thereof, more advanced technique is required. When the hard part of an endoscope is located closer to the distal end thereof, obedience improves.

As mentioned above, since a soft part has a plurality of hardness variation areas or a wide hardness variation area, the magnitude of variation of the hardness level of the soft part can be further reduced and the bent shape of the soft part can be further smoothened. When an endoscope is inserted, the sharp bending of the soft part can be prevented more effectively. Excellent insertional smoothness can be provided, and the contents of the endoscope can be protected from being damaged. The other operations and advantages are identical to those in the aforesaid embodiment.

Figure 31:
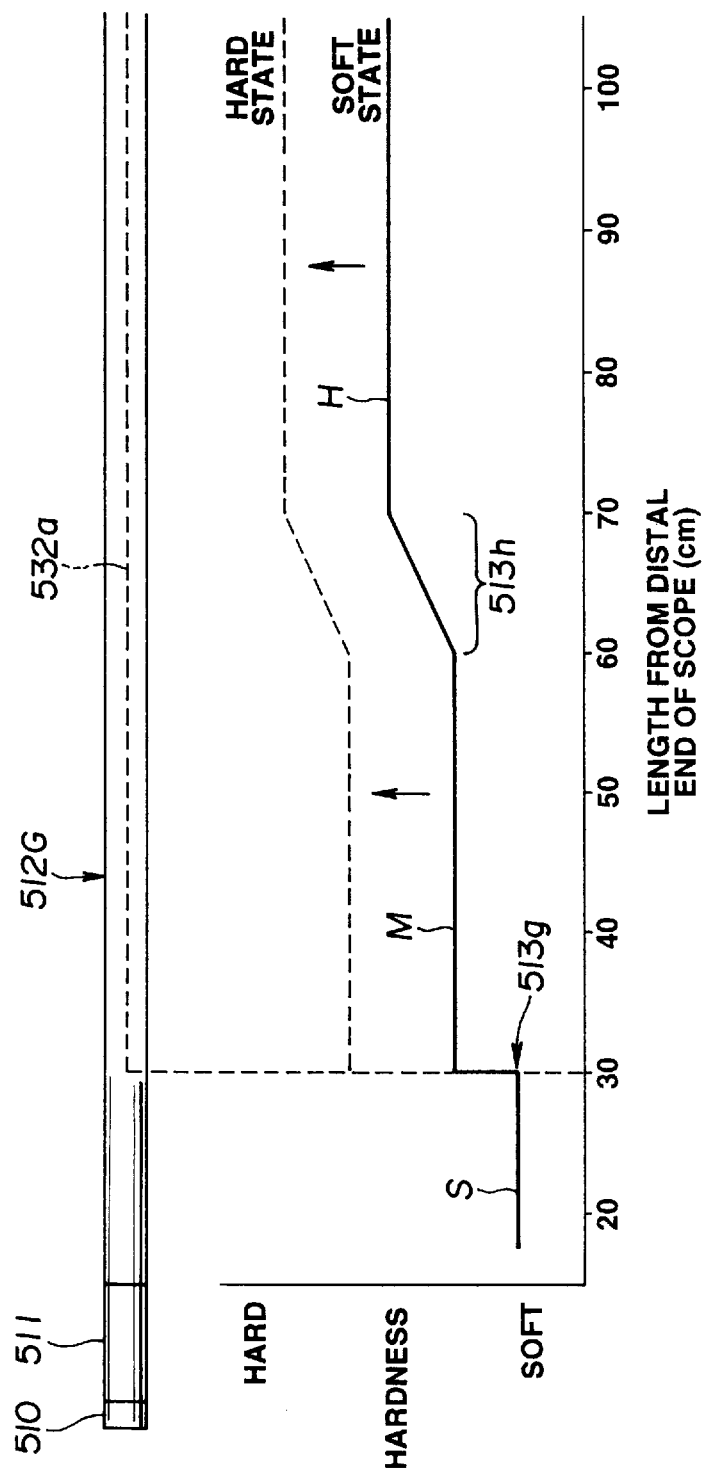
FIG. 31 is an explanatory diagram showing yet another example of the structure of an endoscope having a hardness adjustment mechanism and employed in an endoscope system in accordance with the present invention, that is, a diagram expressing the characteristic balance in hardness of an endoscope having a soft part that includes a variable hardness point and variable hardness area while showing the relationship between distances from the tip of the soft part and hardness levels.

Referring to FIG. 31, another example of the structure of an endoscope having a hardness adjustment mechanism will be described.

As illustrated, a soft part 512G in this embodiment has a hardness variation point 513g and hardness variation area 513h, and the hardness level of the soft part 512G thus varies stepwise. The hardness variation point 513g is located at the distal end of a coil 532a incorporated in the soft part 512G.

The coil 532a itself is formed with a wire whose diameter is larger than that of the coil 532. Thus, the hardness of a hardness variation mechanism is set rather high. The transition from the softest area S to intermediate-hardness area M in the distal side of the soft part 512G is not achieved by varying the hardness level of the armor tube 531 forming the soft part 512 but achieved by varying the hardness level of a content of the soft part 512.

Since the hardness level of the soft part is thus varied by varying the hardness level of a content of the soft part, a plurality of hardness variation points at which one hardness level is changed to another can be defined easily. A plurality of separate armors exhibiting different hardness levels need not be prepared but the hardness level of the soft part can be varied stepwise. The number of armors can therefore be reduced, and the manufacturing process can be simplified.

As shown in FIG. 29, when an armor is molded to have two hardness variation areas, the larger the difference in hardness between the softest area and hardest area is, the more difficult it becomes to vary the hardness stepwise. When one of hardness variation areas is, as shown in FIG. 31, formed by embedding a content therein, stepwise variation of hardness can be realized easily. Moreover, the content for varying the hardness of the soft part is not limited to a coil but may be an aeration tube or perfusion tube. The thickness of the aeration tube or perfusion tube is varied in order to vary the hardness of the soft part.

Figure 32:
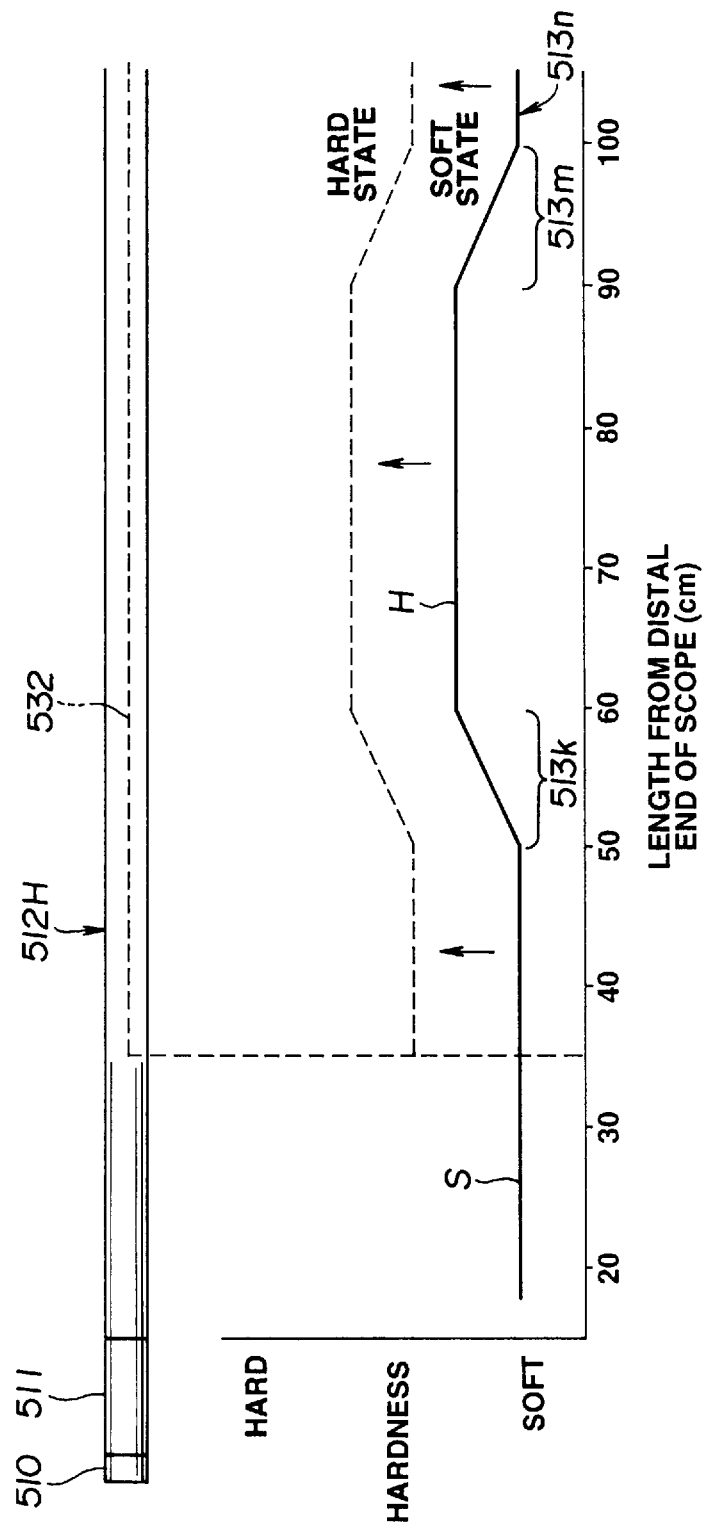
FIG. 32 is an explanatory diagram showing yet another example of the structure of an endoscope having a hardness adjustment mechanism and employed in an endoscope system in accordance with the present invention, that is, a diagram expressing the characteristic balance in hardness of an endoscope having a soft part that includes two variable hardness areas while showing the relationship between distances from the tip of the soft part and hardness levels.

Referring to FIG. 32, yet another example of the structure of an endoscope having a hardness adjustment mechanism will be described.

As illustrated, in this embodiment, a soft part 512H has a front hardness variation area 513k and back hardness variation area 513m. The front hardness variation area 513k is defined to make a transition from the softest area S to the hard area H, while the back hardness variation area is defined to make a transition from the hard area H to a proximal soft area 513n that is soft.

As mentioned above, the proximal soft area is defined beyond the back hardness variation area so that a transition can be made smoothly from the hardest area to the soft area in the proximal side of the soft part. When the soft part is softened to be inserted into the sigmoid colon, the operation unit need not be twisted forcibly. By merely twisting the soft part, the soft proximal soft area is deflected to absorb the deflection of the soft part. The magnitude of deflective force can be reduced. This leads to improved efficiency in twisting the soft part.

When the distal part of an endoscope is inserted to a deep region in the large intestine, there is the fear that even the proximal soft area 513n located proximally to the hard area H is inserted and deflected. However, the proximal soft part 513n has the coil 532 incorporated therein. The softness of the proximal soft area 513n can be compensated by improving the rigidity of the coil 532, whereby it is prevented that the proximal soft area 513n is deflected in a living body.

Figure 33:
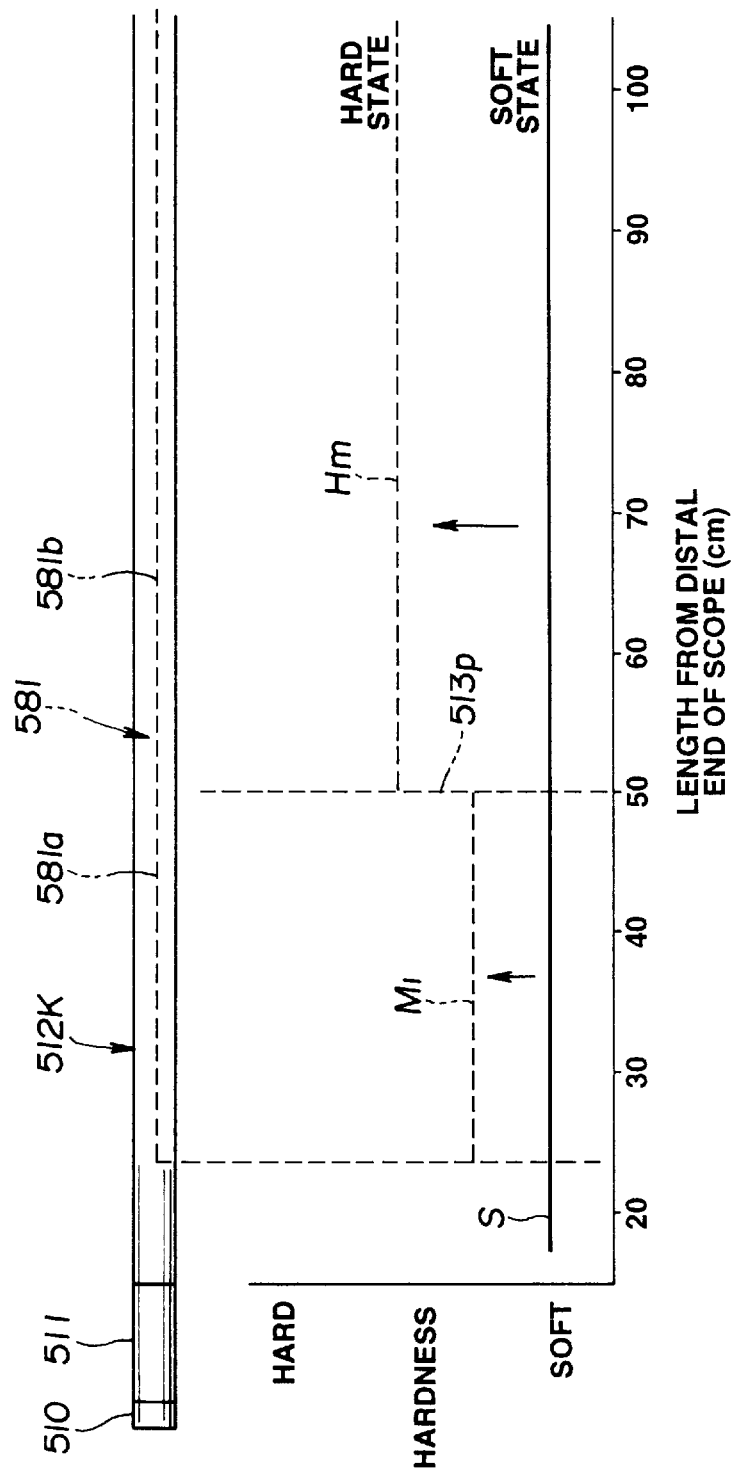
FIG. 33 is an explanatory diagram showing yet another example of the structure of an endoscope having a hardness adjustment mechanism and employed in an endoscope system in accordance with the present invention, that is, a diagram expressing the characteristic balance in hardness of an endoscope having a soft part that has a plurality of variable hardness points formed using a coil pipe while showing the relationship between distances from the tip of the soft part and hardness levels.

Referring to FIG. 33, another example of the structure of an endoscope having a hardness adjustment mechanism will be described.

As indicated with a solid line in the drawing, according to this embodiment, when a coil 581 is not compressed, the hardness of a soft part 512K is set to the level of the softest area S over its entire length. However, when the coil 581 is compressed to the greatest extent, the hardness of the soft part 512K varies in three steps from the hardness of the softest area S, the hardness of an intermediate-hardness area M1 indicated with a dashed like, to the hardness of the hardest area Hm indicated with a dashed line.

The coil 581 lying through the soft part 512K and having the distal end thereof located at a position 25 cm away from the tip of the endoscope is composed of a distal side and proximal side having different strengths. The distal side of the coil 581 is formed with a small-diameter coil 581a having a small diameter, and the proximal side thereof is formed with a large-diameter coil 581b having a large diameter. The border between both of the sides located at a position 50 cm away from the tip of the endoscope serves as a hardness variation point 513p at which the hardness of the soft part 512K varies.

As mentioned above, the distal side and proximal side of the coil included in the hardness variation mechanism are formed with coils exhibiting different hardness levels, and the coil is incorporated in the soft part. The hardness of the soft part having the simplest structure can be varied in a plurality of steps without the necessity of varying the hardness of an armor tube. The armor can therefore be manufactured very simply.

Figure 34:
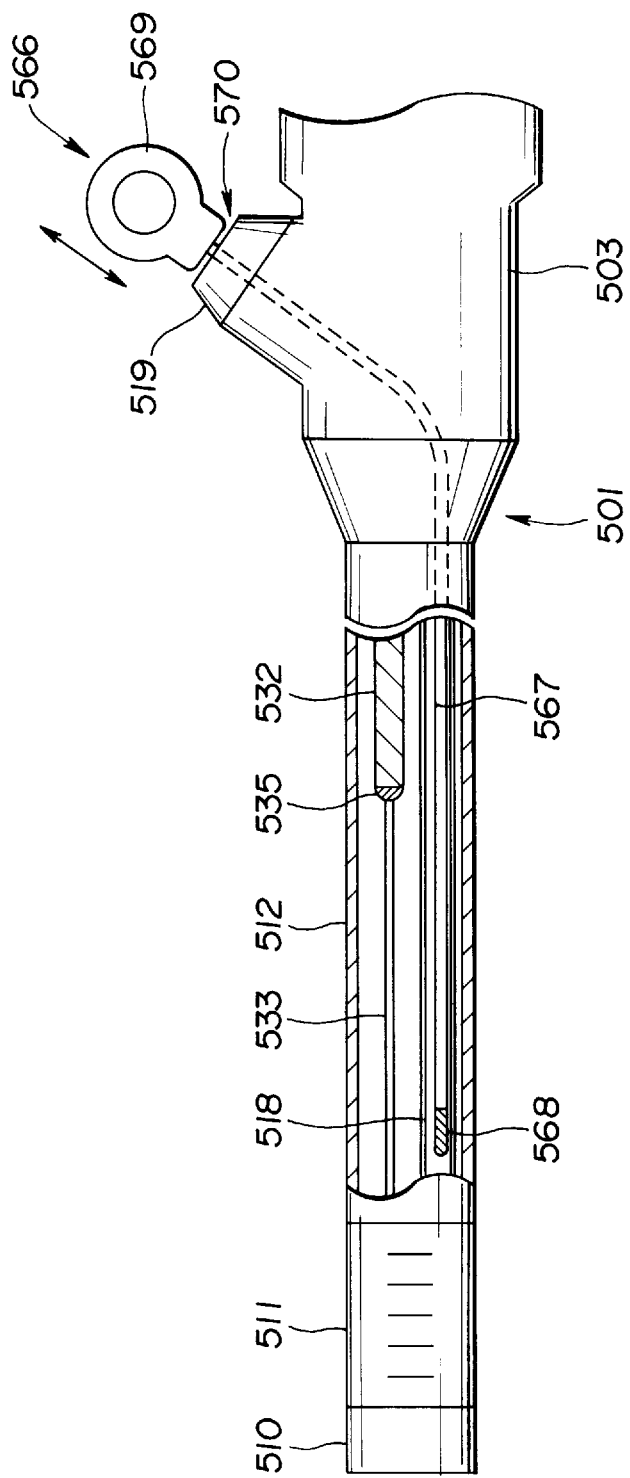
FIG. 34 is an explanatory diagram showing yet another example of an endoscope having a hardness adjustment mechanism and employed in an endoscope system in accordance with the present invention, that is, a diagram for explaining a stylet to be passed through a forceps channel tube included in an endoscope having a soft part that includes a variable hardness point or variable hardness area.

Referring to FIG. 34, yet another structure of an endoscope having a hardness adjustment mechanism will be described.

In this embodiment, a stylet 566 is inserted into a forceps channel tube 518 incorporated in the endoscope 501. The stylet 566 consists of a distal soft part 568, hard stylet body 567, and a handle 569.

The handle 569 has a stopper 570 that abuts on a treatment appliance insertion port 519. When the stylet 566 is inserted into the forceps channel tube 518, the stopper 570 abuts on the treatment appliance insertion port 519. At this time, the tip of the stylet body 567 is, as illustrated, located distally to the distal end of the coil 532.

Since the stylet body 567 is located distally to the distal end of the coil 532, the softest area S of the soft part 512 distal to the distal end of the coil 532 can be hardened if necessary.

Moreover, the hardness of the stylet body 567 of the stylet 566 is determined so that the stylet body has rigidity making the soft part 512 about 1.2 times or more harder.

As mentioned above, since a stylet can be passed through the forceps channel if necessary, the hardness of the softest area S in the distal side of the soft part, which cannot be varied in a normal use state, can be set to a higher level. A manipulation made proximally can be conveyed reliably to the distal part, and excellent insertional smoothness can be guaranteed.

Referring to FIGS. 35 to 42, the structure of an endoscope making it possible to protect the contents of the endoscope from being damaged by functioning a hardness variation mechanism even in a use situation in which an insertion unit is bent with a given minimum radius of curvature.

Figure 35:
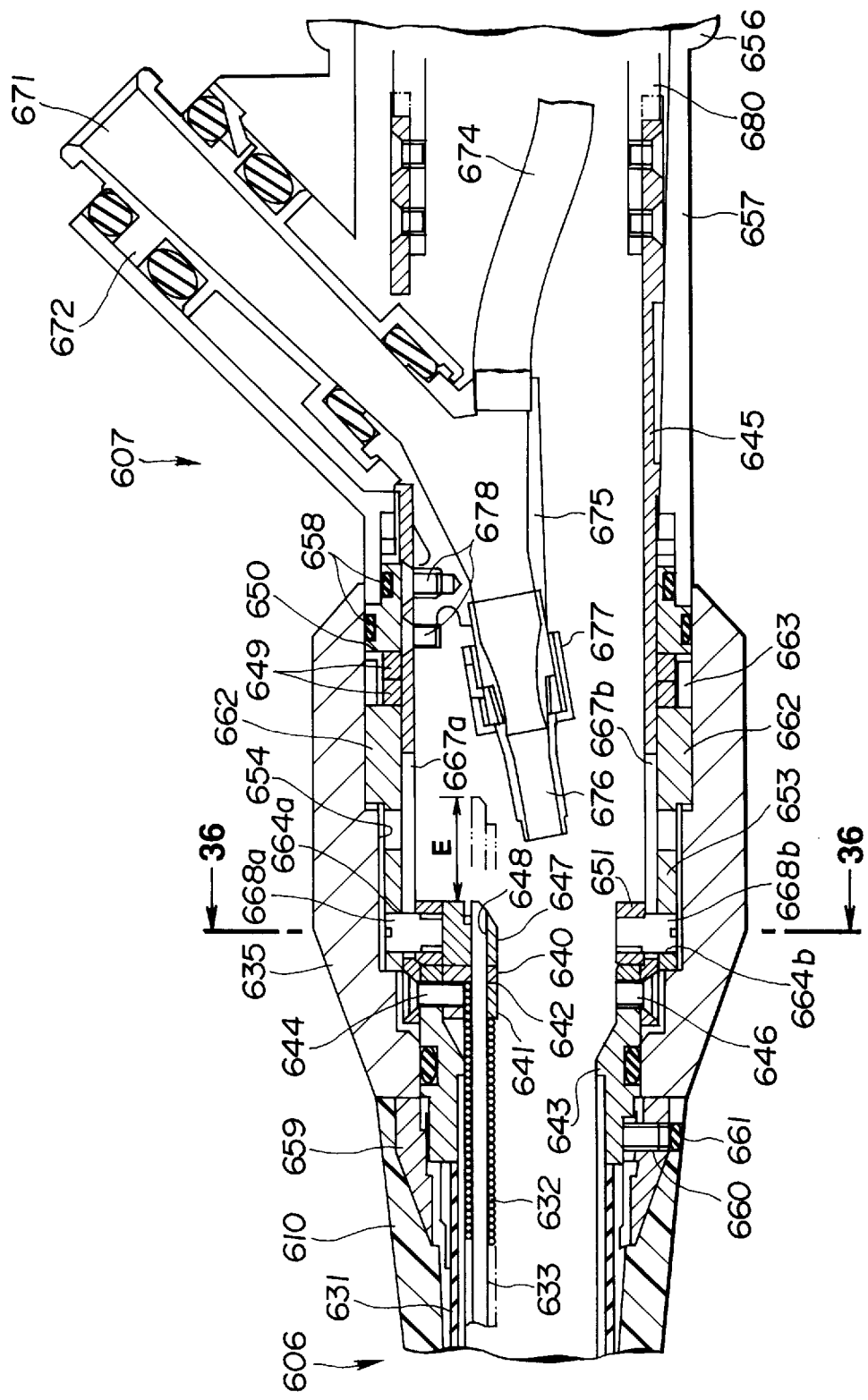

As shown in FIG. 35, an operation unit 607 has a hardness adjustment mechanism for use in adjusting the hardness level of a soft part. The hardness adjustment mechanism includes a cylindrical hardness adjustment knob 635 located on the front end of the operation unit 607 adjoining an anti-bending tube 610 and to be manipulated for adjusting hardness. The hardness adjustment knob 635 is rotated in order to manipulate an adjustment mechanism to be described later, whereby a coil 632 and wire 633 incorporated in a soft part 613 are set to certain states. Finger rest ditches 636 are formed along the outer circumference of the hardness adjustment knob 635.

The practical structure of the adjustment mechanism will be described. The proximal end of the coil 632 is attached on a fixed basis to a coil stopper 640 locked in the front end of the operation unit 607. Specifically, the proximal end of the coil 632 is fitted into a hole 641 bored in the coil stopper 640, abutted on the end surface of a front-end stepped hole 642 in the hole 641, and secured by pouring a brazing filler such as solder or an adhesive into the front-end stepped hole 642. Since the back end of the coil is thus attached to the coil stopper 640, the back end of the coil 632 is restrained (hindered) from moving backwards from the secured position and from rotating. Moreover, the coil 632 is attached to the axis of the insertion unit 606 in a state in which the coil will not rotate. By the way, the wire 633 lying through the coil 632 penetrates through the hole 641 of the coil stopper 640, juts backwards, and is movable back and forth freely relative to the coil 632.

The coil stopper 640 is fixed to a back base 643, which fixes the back end of a soft tube 631 to the operation unit 607, by means of a screw 644. The back base 643 is locked in the vicinity of the front end of a cylindrical tube 645 placed on the outer circumference of the back base 643 by means of the screw 644 and another screw 646.

Figure 36:
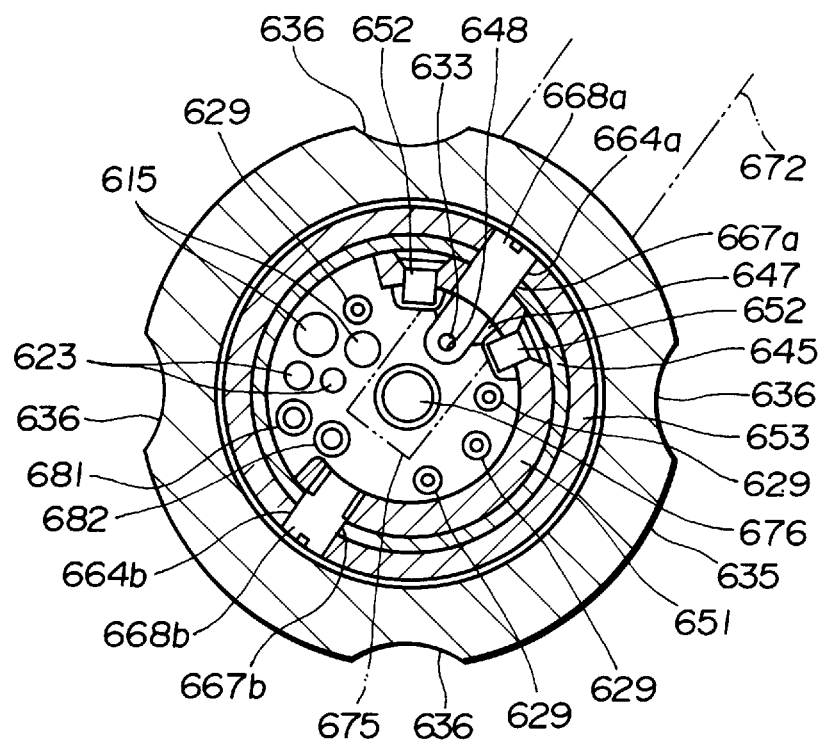

The proximal end or back end of the wire 633 is fitted into a linking bore 648 bored in a towage member 647, and fixed firmly to the towage member 647 by performing brazing or the like. The towage member 647 is united with the wire 633 and can be moved back and forth together with the wire 633. As shown in FIG. 36, the towage member 647 is fixed to a movable ring 651, which is formed with a notched cylindrical ring member while being joined with the inner wall surface of the movable ring 651, by means of a screw 652.

The outer circumferential surface of the movable ring 651 is matched with the inner surface of a cylindrical tube 645 of the operation unit 607 and therefore closely engaged with the inner surface thereof, thus permitting the back-and-forth movement of the movable ring 651. In short, the outer circumferential surface of the movable ring 651 serves as a guiding means for helping the movable ring 651 move linearly back and forth. The towage member 647 is movable back and forth while united with the movable ring 651 and wire 633.

A cam cylinder 653 engaged with the outer circumferential surface of the cylindrical tube 645 and mounted to be freely rotatable is placed outside the cylindrical tube 645. The cam cylinder 653 is fitted into a stepped hole 654 bored in the inner surface of the hardness adjustment knob 635. The front end of the cam cylinder 653 is abutted on the front end of the stepped hole 654 and thus restrained from advancing. Moreover, the back end of the cam cylinder 653 is abutted on a seal ring 650 engaged with the cylindrical tube 645 and thus restrained from withdrawing. The cam cylinder 653 is supported by the seal ring 650 via a plurality of rings 649.

The seal ring 650 is abutted on the front end of a cylinder 657 forming a grip portion 656 of the operation unit 607, and thus locked and positioned not to be able to withdraw. The front half of the seal ring 650 is embedded in the inner surface of the back end of the hardness adjustment knob 635, while the back half of the seal ring 650 is fitted in the inner surface of the front end of the cylinder 657. A seal member 658 is interposed between the outer circumference of the front half of the seal ring 650 and the hardness adjustment knob 635, and between the outer circumference of the back half of the seal ring 650 and the cylinder 657.

The front end of the hardness adjustment knob 635 abuts on the back end of an annulus ring-like support member 659 for supporting the anti-bending tube 610, whereby the forward movement of the hardness adjustment knob is restrained. The support member 659 is screwed into the back base 643, fastened to the back base 643 by means of a screw 660, and thus restrained from rotating. An attachment hole for the screw 660 is sealed with a filler 661.

The hardness adjustment knob 635 is engaged with the outer circumferential surface of the cylindrical tube 645 via the cam cylinder 653. As mentioned above, the cam cylinder 653 can be rotated while being in contact with the outer circumferential surface of the cylindrical tube 645 and rotatable about the cylindrical tube 645 with the back-and-forth movement thereof restrained.

A plurality of locking projections (convex parts) 662 are formed partly on the outer circumference of the cam cylinder 653. The projections 662 are fitted into ditches (concave parts) 663 formed in the inner surface of the hardness adjustment knob 635. Since the projections 662 are fitted into the ditches 663, the cam cylinder 653 and hardness adjustment knob 635, which are separate bodies, are joined with each other in such a way that they cannot rotate. The cam cylinder 653 is rotated together with the hardness adjustment knob 635.

Figure 37A:
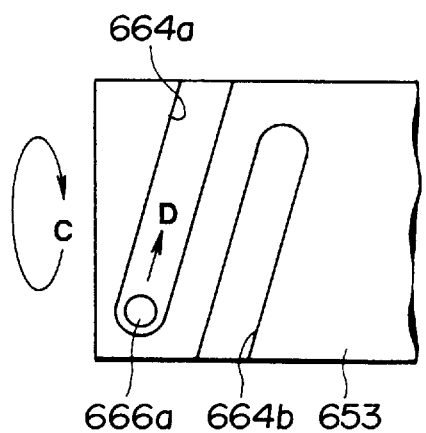
FIGS. 37A and 37B are diagrams for explaining a cam cylinder included in the hardness adjustment mechanism.
Figure 37B:
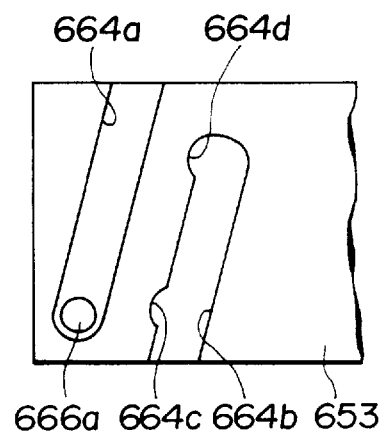

Two cam grooves 664a and 664b having the same orientation and the same length are formed spirally in the cam cylinder 653 in such a way that they are opposed to and separated from each other. FIG. 37A shows the shapes of the cam grooves 664a and 664b in the cam cylinder 653. The cam grooves 664a and 664b constitute a double-groove cam and have the same shape. The cam grooves 664a and 664b are located at such symmetrical positions that when one of the cam grooves is rotated 180° with respect to the axis of the cam cylinder 653, the cam groove will coincide with the other cam groove. In FIG. 37A, the cam grooves 664a and 664b have a simple and smooth contour or are smoothly spiraling. Instead of the structure, as shown in FIG. 37B, for example, a recess 664c may be formed in the middle of the groove 664b or a recess 664d may be formed at the end of the groove 664b. By adopting this structure, when pins 666a and 666b are fitted into the recesses, an operator can perceive a click.

Moreover, elongated long holes 667a and 667b are bored in the cylindrical tube 645 along the axis of the center of rotation of the hardness adjustment knob 635 so that the long holes are opposed to and separated from each other. Two pins 668a and 668b are screwed to the movable ring 651. The pins 668a and 668b are fitted in the associated long holes 667a and 667b and the associated cam grooves 664a and 664b. The length between the front and back ends of each of the long holes 667a and 667b along the center axis is set to a length covering a range within which the back end of the wire 633 should be moved (area E in FIG. 35). The cam grooves 664a and 664b in the cam cylinder 653 have a length larger than the above length along the center axis.

When the hardness adjustment knob 635 is rotated, the hardness adjustment knob 635 moves the pins 668a and 668b forwards or backwards along the long holes 667a and 667b while moving along the cam grooves 664a and 664b in the cam cylinder 653. This causes the towage member 647 to move forwards or backwards. The hardness adjustment knob thus serves as a manipulation mechanism for advancing or withdrawing the wire 633 lying through the coil 632 whose back end is attached to the towage member 647. A force exerted to withdraw the towage member 647 is applied as a compression force to the coil 632, whereby the hardness of the coil 632 is adjusted. To begin with, when the towage member 647 is not moved backwards, the towage member 647 abuts on the coil stopper 640. The coil 632 whose backward movement is restricted has the highest flexibility, that is, is softened to bend most readily or have the lowest hardness.

Moreover, when the towage member 647 moves backwards in this state, the back end of the wire 633 moves backwards at the same time. As a result, the coil stopper 640 exerts the operation of compression so as to thrust the coil 632 forwards. That is to say, when a force for moving the wire 633 backwards is applied to the back end of the wire 633, a compressing force is applied to the coil 632. With the compressing force, the coil 632 having elasticity becomes less flexible, that is, gets hardened not to bend readily and to have high hardness (or more accurately, hardness against bending). In this case, the magnitude of compressing force to be applied to the coil 632 can be changed according to a distance by which the towage member 647 is moved backwards. Thus, a hardness adjustment means for changing the degree of flexibility of the coil 632 (hardness level) is realized.

By the way, as shown in FIG. 35, an insertion port frame 672 defining the treatment appliance insertion port 671 is located at a position adjacent to and in front of the grip portion 656 of the operation unit 607. The insertion port frame 672 is joined inside the operation unit 607 with a branching member 675 branched into a portion leading to the treatment appliance insertion port 671 and a suction channel 674. The proximal end of a treatment appliance channel tube 676 incorporated in the insertion unit 606 is linked to the front end of the branching member 675 by means of a linkage 677. The branching member 675 is fixed to the cylindrical tube 645 by means of a screw 678. The cylindrical tube 645 has the back end thereof linked to a frame 680, to which a bending mechanism included in the operation unit 607 is attached, using a screw 679. The cylindrical tube 645 is structured not to rotate even when the hardness adjustment knob 635 is rotated.

The insertion unit 606 and operation unit 607 have, as shown in FIG. 36, various contents. Specifically, the contents include four bending wires 629 located at vertically and laterally opposed positions, two signal lines 623 located near the center, two light guides 615 located above the center, the treatment appliance channel tube 676 located below the center, the coil 632 and wire 633 located at a right upper position, and the aeration tube 681 for supplying air and the perfusion tube 682 for supplying water which are located at left lower positions. The contents of the operation unit 607 become a little different from those of the insertion unit 606 especially near the branching member 675. This is attributable to a constituent feature of the present invention to be described later.

Figure 38A:
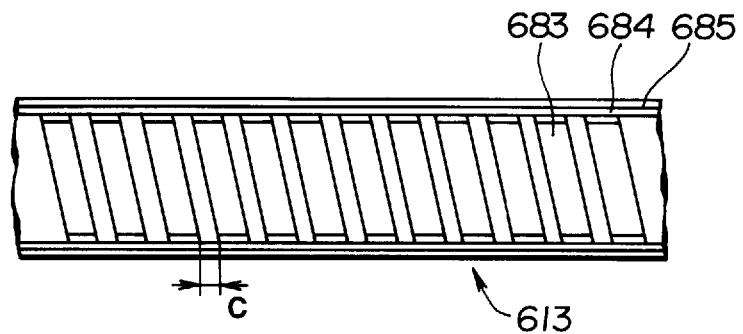
FIGS. 38A and 38B are sectional views for explaining the structure and operation of a soft tube forming a soft part of an insertion unit of the endoscope.
Figure 38B:
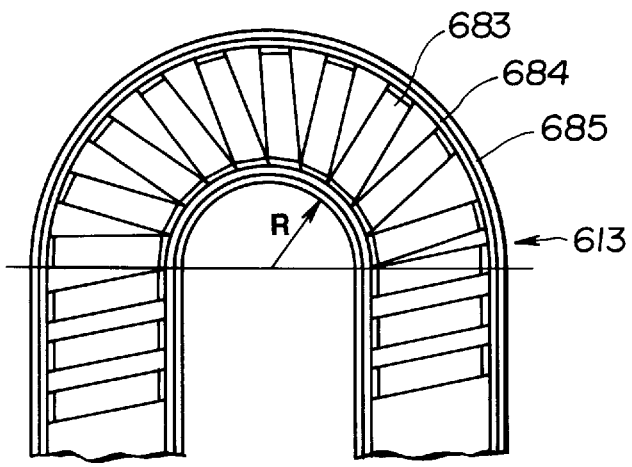

FIGS. 38A and 38B show the internal structure of a soft tube forming the soft part 613. The soft tube is made by placing a spiral tube 683 (two-ply or three-ply tube) as an innermost layer, a reticulate tube 684 outside the spiral tube, and an armor resin 685 as an outermost layer.

Figure 39:
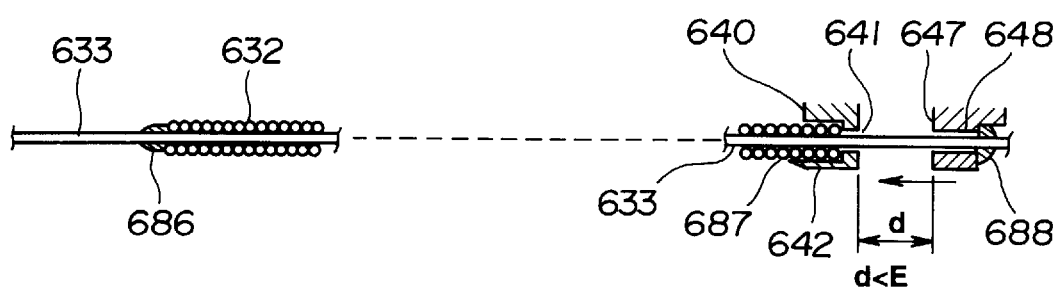

The constituent feature of the present invention will be described. FIG. 39 shows a fixed state of the coil 632 and wire 633 constituting a hardness adjustment mechanism. The tip of the coil 632 is fixed firmly to part of the distal end of the wire 633 using a brazing filler 686 or the like. The back end of the coil 632 is firmly fixed to the towage member 647 using a brazing filler 688 or the like. When the coil 632 and wire 633 are in their natural states, as shown in FIG. 39, there is a distance "d" between the back end of the coil stopper 640 and the front end of the towage member 647. For incorporating this assembly in the operation unit 607, the back end of the wire 633 is inserted into the coil 632 and the relevant members such as the towage member 647, movable ring 651, pins 688a and 688b, and cam cylinder 653 are assembled so that the distance will be nullified. In other words, when incorporated, the coil 632 is stretched and extended by a length corresponding to the distance "d." The coil 632 is a close-contact coil in its natural original form. When incorporated, as shown in FIG. 35, the coil 632 has a little space between turns of a wire. The distance "d" is smaller than the aforesaid distance "E." When the insertion unit 606 is straightened, a difference "E–d" is regarded as a stroke by which the wire 633 is towed in order to apply a compressing force to the coil 632, and shall be referred to as a hardness adjustment length. The hardness adjustment mechanism has the hardness adjustment length of the set so that the coil 632 formed with an elongated member will not buckle even when the soft part 613 of the insertion unit 606 is bent with a given minimum radius of curvature.

Figure 40:
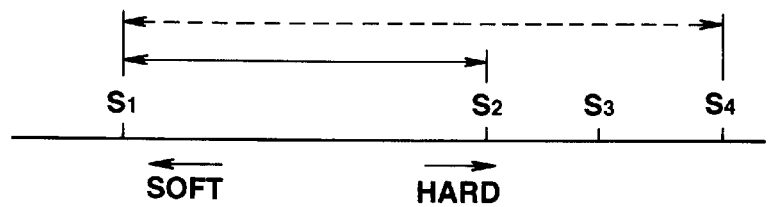

FIG. 40 shows a hardness variation range, that is, a range of levels within which the soft part 613 of the insertion unit 606 can be hardened using the coil 632 that is a hardness (flexibility) adjustment member by rotating the hardness adjustment knob 635. S1 indicates a hardness level at which the soft part is softened most, and S2 indicates a highest hardness level at which the soft part of the endoscope 602 is hardened most. S3 indicates a hardness level at which the hardened coil 632 starts buckling when the soft part 613 is bent with a minimum radius of curvature. S4 indicates an ideal highest hardness level. The endoscope 602 is not hardened to the level S4 but the hardness of the endoscope 602 is set within the hardness variation range defined with the levels S1 and S2. The levels S1 to S4 are hardness levels produced when the soft part 613 is substantially straightened.

In the operation unit 607, the towage member 647 jutting inside the movable ring 651 is, as shown in FIG. 36, located at an upper nearly-right position. The direction of the upper right position substantially agrees with the direction of the positions of the branching member 675, treatment appliance insertion port 671, and insertion port frame 672 (path extending from the treatment appliance insertion port 671 to the treatment appliance channel tube 676). That is to say, at least part of the towage member 647 lies above the branching member 675. In FIG. 36, the coil 632 and wire 633 are located at the upper nearly-right position.

Figure 41:
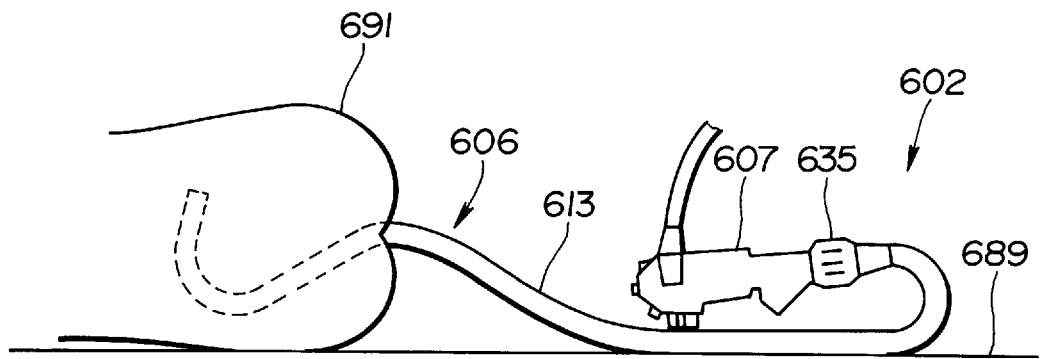

FIG. 41 shows a scene of use in which the electronic endoscope 602 is inserted into the large intestine of a patient 691.

First, the soft part 613 of the insertion unit 606 is softened. In this state, the insertion unit 606 is inserted along the tortuous sigmoid colon 92. As shown in FIG. 39, since the coil 632 is thrust by the distance "d," there is a little gap between turns of the wire of the coil 632. The coil 632 will therefore not be hardened naturally even when looped. Due to the gap between turns of the wire of the coil, the coil 632 attempts to contract. The wire 633 in the coil 632 loses its tension. Consequently, the elongated member composed of the coil 632 and wire 633 is softened as a whole.

Assuming that the thrust by the distance "d" is not given, that is, the coil 632 maintains a close-contact state, even when the coil stopper 640 and towage member 647 are assembled as shown in FIG. 35, if the insertion unit 606 remains straight, no force works on the wire 633. In this state, as mentioned above, the elongated member remains soft as a whole.

However, when the soft part 613 and insertion unit 606 loop (See FIG. 6A), even if the hardness adjustment knob 635 is not manipulated, the wire 633 in the coil 632 is tensed naturally. A tractive force works on the wire 633. The turns of the wire of the coil 632 come into close contact with one another and the coil 632 is hardened as a whole. In this case, if the insertion unit is inserted into the sigmoid colon 92 while being looped, the loop will expand and give the patient 691 a greater pain.

However, according to the present invention, as shown in FIG. 39, since the wire 633 is thrust by the distance "d" and thus initialized, even when the soft part 613 or insertion unit 606 loops, it will not be hardened.

When the tip of the insertion unit 606 passes through the descending colon 93 and reaches a region near the splenic curvature 94, the insertion unit 606 is pulled while being twisted (See FIG. 6B), and thus substantially straightened. This causes the sigmoid colon 92 to contract. At this time, the hardness adjustment knob 635 is manipulated in order to harden the soft part 613 of the insertion unit 606. In this state in which the distal part of the endoscope satisfactorily obeys a manipulation made optimally, the distal part is inserted into the transverse colon 95, hepatic curvature 97, ascending colon 96, and cecum 98. When the distal part is inserted into a deep region, since the soft part 613 is hardened, the sigmoid colon 92 will hardly deflect again. The soft part will hardly loop in the middle of the large intestine, and the distal part can be inserted into the cecum 98.

By contrast, when no compressing force is applied to the coil 632 (softened), the coil 632 is highly flexible. Even when the soft part 613 is bent to become smallest in size, the coil 632 inside the soft part will not be buckled or damaged at all. However, in general, something harder is more liable to hook when bent (to be plastically deformed). The same applies to the coil 632. The harder the coil 632 is, the more readily the coil buckles in such a way that part of the wire juts out (falls out) to form buckles 609 shown in FIG. 42. Once part of the wire of the coil falls out, the adjoining part thereof falls out consecutively responsively to compression. Sufficient hardness cannot therefore be produced any longer.

As shown in FIG. 6C, in a living body, the harder the soft part is, the larger magnitude of force the soft living body absorbs. A small bend will therefore not be created. Consequently, a phenomenon that the coil 632 buckles will not occur.

From a functional viewpoint, a hardness variation range or a range of levels within which the hardness of the soft part can be varied should be as wide as possible. Referring to FIGS. 6B and 6C, for preventing the sigmoid colon 92 from deflecting again, the insertion unit 606 is sheathed with, for example, a rigid tube referred to as a sliding tube, and then the tube is inserted into the sigmoid colon 92 so that the sigmoid colon 92 will remain straight while the tip of the insertion unit 606 travels from the splenic curvature 94 to the cecum 98. This procedure has been adopted in the past. When the sliding tube is used in combination with the soft part 613, the soft part becomes so hard that the sigmoid colon 92 will not deflect any longer. The coil 632 is hardened so that the insertion unit 606 can reproduce the hardness (or higher hardness). The hardness level is the ideal level S4 in FIG. 40.

Now, a phenomenon that may occur outside a living body will be discussed with reference to FIG. 41. The positions of the insertion unit 606 and operation unit 607 of the endoscope 602 outside a living body are determined by an operator. When the insertion unit 606 is inserted into a patient 691 lying down on a bed 689, part of the soft part 613 is often in contact with the bed 689. The operation unit 607 is usually held at a position at which the proximal side of the soft part 613 will not make a small bend. However, if an operator has difficulty in inserting an endoscope, though it hardly occurs, the operation unit 607 may, as shown in FIG. 41, be positioned above the soft part 613 unintentionally (the soft part 613 is interposed between the operation unit 607 and bed 689). At this time, the proximal side of the soft part 613 may bend with a minimum radius of curvature (about 180°). Thus, the soft part 613 may make a small bend artificially outside a living body.

Figure 42:
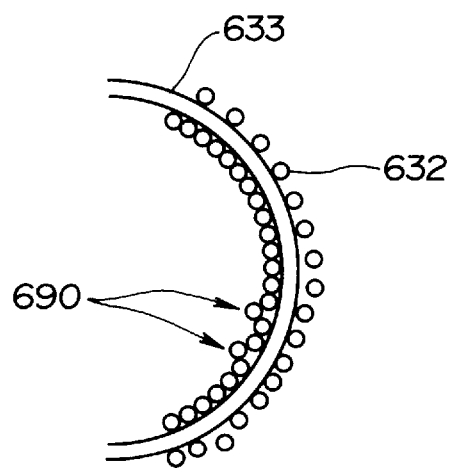

When the soft part 613 is set to a higher hardness level by manipulating the hardness adjustment knob 635, it becomes rarer that the soft part 613 makes a small bend. The phenomenon shown in FIG. 41 may be thought to result from abnormal usage, and may not be concerned about. A hardness variation range or a range of levels within which the hardness of the soft part 613 can be varied may be set so that the soft part 613 can be made as hard as possible. This is one of ways of thinking (however, supposing the phenomenon shown in FIG. 41 occurred when the soft part is hardened, the coil 632 would buckle as shown in FIG. 42).

However, there are large individual differences in expertise, habitual practice, and level of an inserting skill. It cannot therefore be said that as long as the soft part 613 is hardened to the greatest extent, the phenomenon resulting from abnormal usage which is shown in FIG. 41 will never occur.

According to the present invention, the abnormal usage is taken into account. Instead of setting the hardness variation range so that the coil 632 can be hardened to the greatest extent, the hardness variation range is set to a range (a range defined with the levels S1 and S2 in FIG. 40) in which the coil will not buckle even when the soft part 613 bends, as shown in FIG. 41, with a minimum radius of curvature (corresponding to an angle of about 180°). Consequently, when the soft part 613 is bent with the minimum radius of curvature, the hardened coil 632 lying in the soft part will not buckle. Thus, the ability to vary hardness is exerted even when the soft part 613 is bent with the minimum radius of curvature.

Referring to FIGS. 38A and 38B, the minimum radius of curvature, R, of the soft part 613 of the insertion unit 606 will be described. The smallest bent form of the soft part 613 is a form in which the soft part 613 is bent so that the bent edges of turns of the wire (band) forming the spiral tube 83a will come into contact with one another. Specifically, when the soft part is bent a gap, c, between turns of the band forming the spiral tube 83 which is attained when, as shown in FIG. 38A, the soft part is straightened is narrowed along the circle of curvature at an inside position on the bent area of the soft part (widened along the circle of curvature at an outside position thereon). A bent state attained when the gap c is nil (FIG. 38B) corresponds to the minimum bent form, and the radius of the inner circle of curvature is the minimum radius of curvature.

Moreover, the hardness variation means may be any elongated member other than the coil 632 and wire 633, for example, a thermosoftening resin or thermosetting resin and a heating means, or a shape memory alloy memorizing a linear state and a heating means. In any case, as mentioned above, any elongated member can be adopted as long as it has the nature that as it becomes harder, it can more readily deform plastically responsively to given bending.

As shown in FIG. 36B, the direction in which the towage member 647 lies with respect to the center of the insertion unit is substantially the same as the direction in which the branching member 675 (treatment appliance insertion port 671, insertion port frame 672) lies. A space inside the cylindrical tube 645 can therefore be utilized effectively. Without the towage member 647, all the contents except the treatment appliance channel tube 676 are arranged so as not to invade the branching member 647. If the towage member 647 is located in front of the branching member 675, when the towage member 647 is located in the direction in which the towage member and branching member 675 lie up and down, an extra space can be preserved for the other contents. Without the extra space, each of the contents is forced to run in an unnatural manner or likely to rub against the towage member 647, branching member 675, or movable ring 651. The possibility that the contents are damaged increases. When the towage member 647 is positioned in a direction in which at least part of the towage member 647 and the branching member 675 lie up and down, the space in the cylindrical tube 645 can be used effectively.

While the hardness variation function is used repeatedly, the wire 632 may be stretched (plastically deformed) gradually relative to the coil 632. In this case, one or two of the rings 649 are placed in front of the cam cylinder 653. In other words, the rings 649 are exchanged (i.e. change places) with the cam cylinder 653. Thus, the initial positions of the pins 668a and 668b and the towage member 647 can be shifted backwards. Thus, the hardness variation function can be repaired and optimized easily.

Assuming that the coil 632 is hardened, part of the hardened coil 632 may press part of the other contents such as the light guides 615, signal lines 623, bending wire 629, treatment appliance channel tube 676, aeration tube 681, and perfusion tube 682 because the the coil 632 can move inside the soft tube 631. The hardness of the coil 632 and the strengths of the other contents are determined so that even when the soft tube 631 is bent by a given magnitude, if the coil 632 presses the other contents, the other contents will not be hooked or crashed.

The given magnitude of bending is, as mentioned above, a maximum of 180°. The strengths of the other contents are determined by the sizes and materials of the contents. The hardness of the coil 632 is as shown in FIG. 40. A solid line indicates a range of measured levels, and a dashed line indicates a range of levels to which the hardness of the coil can be set. When the hardness level of the coil is equal to or larger than the level S2, the other contents may buckle with the above give magnitude of bending. A hardness variation range or a range of levels within which the hardness of the coil can be varied is set to a range allowing the contents to remain undamaged. As long as a channel such as the treatment appliance channel tube 676, aeration tube 681, or perfusion tube 682 is concerned, what is referred to as "remain undamaged" means that the channel will not be locally streaked or plastically deformed to be folded. As long as the signal lines 623 are concerned, it means that they will not be disconnected. As far as the light guides 615 are concerned, it means that a plurality of fibers out of a bundle of fibers will not be broken to bring about an abrupt decrease in amount of light. The sizes and materials of the contents as well as the highest hardness of the coil 62 are determined so that when the soft tube 631 is bent by the given magnitude, damage will not take place.

When the coil 632 is put in an endoscope, presumably, it may be pushed into the soft tube 631 tortuously or it may be pulled relative to the soft tube 631. However, if the magnitude of push or pull is too large, when the coil 632 is hardened and the soft tube 631 is bent, the possibility that the coil 632 further compresses the other contents and causes the other contents to buckle gets higher. When the soft tube is straightened and the coil 632 is hardened, the coil 632 should not be pushed into the soft tube 631 or pulled relative to the soft tube 631 too greatly. In other words, the length of the portion of the soft tube 631 containing the coil 632 should be substantially identical to the length of the hardened coil 632. Otherwise, when the soft tube 631 is bent by a given magnitude, the other contents would buckle.

By the way, an endoscope 701 is generally placed in a cleaner or sterilizer or stowed in a stowage case for transportation or storage except when it is used for examination. An example of the stowage case in which the endoscope 701 is stowed is a stowage member 753 shown in FIG. 43.

The illustrated stowage member 753 has a concave part 755 in which the whole or part of the endoscope 701 is stowed (fitted). In the drawing, the whole of the endoscope 701 is fitted in the concave part 755.

As mentioned above, an operation unit 707 of the endoscope 701 has a hardness adjustment knob 715. The hardness adjustment knob 715 has a freely rotatable finger rest 716. The finger rest 716 faces in the Up direction of the endoscope 701, so that a soft part 712 is softened. In this state, the hardness adjustment knob 715 is stowed in the concave part 755 of the stowage member 753.

When the hardness adjustment knob 715 is rotated 180° and the soft part 712 remains hard with the coil inside the soft part 712 compressed to the greatest extent, the finger rest 716 will not be stowed in the concave part 755. This causes a user to become aware of the fact that the coil 732 inside the soft part 712 is compressed.

The load imposed on the coil 732 is removed by rotating the hardness adjustment knob 715, whereby the hardness adjustment knob 715 is stowed at a given position in the stowage member 753.

As mentioned above, when an endoscope is stowed in the concave part of the stowage member, if the hardness adjustment knob is rotated in order to compress the coil, the finger rest of the endoscope juts out of the stowage member. This informs a user of the fact that the coil is compressed. Thus, it can be reliably prevented that an unnecessarily large load is kept imposed on a coil 732 and wire 733, and that the coil 732 and wire 733 deteriorate time-sequentially.

Figure 44:
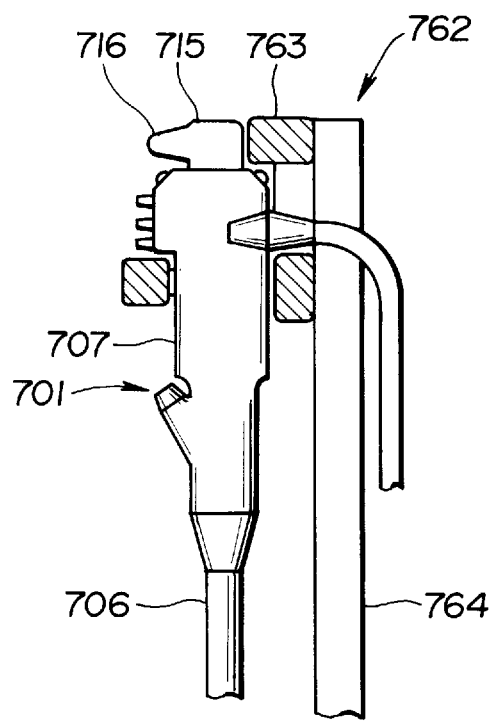
FIG. 44 is a diagram showing a state in which an endoscope having a hardness adjustment mechanism is hung on an endoscope hanger.

Referring to FIG. 44, an endoscope hanger 762 on which the endoscope 701 is hung will be described. As illustrated, the endoscope hanger 762 is composed of a support column 764 and a supporting member 763 located at an upper position of the support column 764. The endoscope 701 is supported mainly at three points on the supporting member 763.

Figure 43:
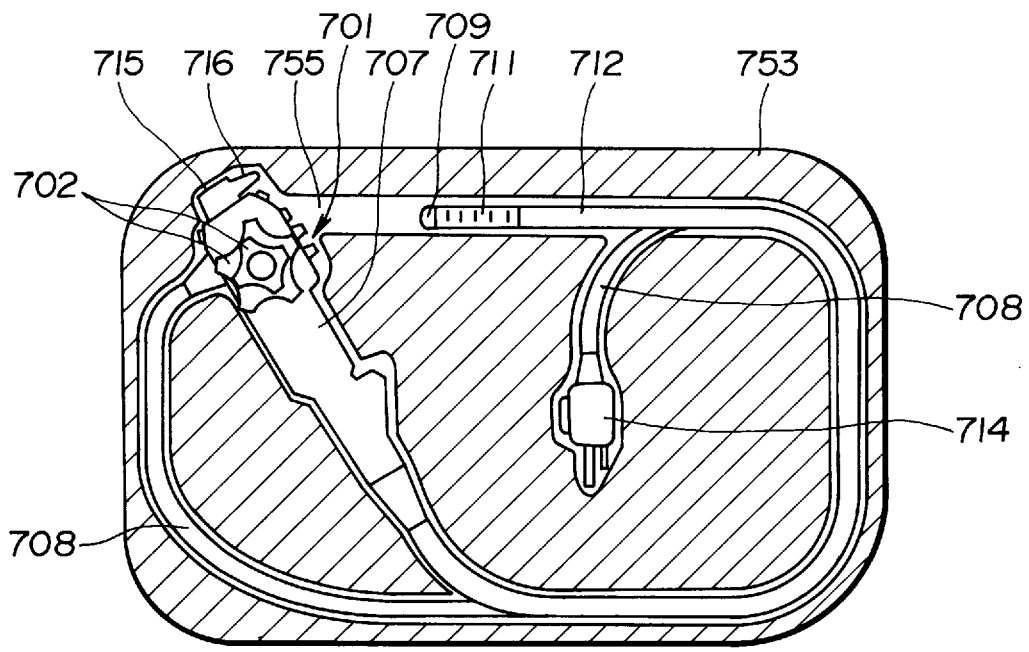
FIG. 43 is a diagram showing a state in which an endoscope having a hardness adjustment mechanism is stowed in a stowage case.

Using the endoscope hanger 762, like using the stowage member 753 described in conjunction with FIG. 43, only when the hardness adjustment knob 715 is returned to a soft-state position, the operation unit 707 of the endoscope 701 can be, as illustrated, placed on the supporting member 763.

Specifically, when the hardness adjustment knob 715 is rotated 180° in order to compress the coil 732, if the soft part 712 is softened, the finger rest 716 is oriented in a 180° opposite direction of the direction in which the finger rest is oriented in the drawing. The finger rest 716 abuts on the supporting member 763 to hinder the operation unit from being placed on the supporting member 763. This causes a user to become aware of the fact that the coil 732 inside the soft part 712 is compressed. The user then rotates the hardness adjustment knob 715 to remove the load from the coil 732. Thus, it can be prevented that an unnecessarily large load is kept imposed on the coil 732 and wire 733, and that the coil 732 and wire 733 deteriorate time-sequentially.

As mentioned above, when an endoscope is hung on the endoscope hanger, if the hardness adjustment knob is rotated in order to compress a coil pipe, since the finger rest of the endoscope abuts on the supporting member, it can be informed that the coil is compressed. It can therefore be prevented that an unnecessarily large load is kept imposed on the coil 732 and wire 733 and the coil 732 and wire 733 deteriorate time-sequentially. The hanger can be used in a cleaner and/or a sterilizer.

According to the present invention, it is apparent that a wide range of different embodiments can be formed on the basis of the present invention without a departure from the spirit and scope of the invention. This invention will be limited to the appended claims but not restricted to any specified embodiments.

What is claimed is:

1. An endoscope system, comprising:
    a first endoscope in which a hardness variation mechanism for use in adjusting a hardness level of a soft part of an insertion unit of said first endoscope is incorporated in said soft part; and
    at least one second endoscope having a soft part,
    wherein a range of levels of the adjustable hardness of said soft part of said first endoscope includes a hardness level of said soft part of said second endoscope.

2. An endoscope system, comprising:
    a first endoscope in which a harness variation mechanism for use in adjusting a hardness level of a soft part of an insertion unit of said first endoscope is incorporated in said soft part; and
    at least one second endoscope usable for examination of a region which is the same as a region examined by said first endoscope and having a soft part,
    wherein a range of levels of the adjustable hardness of said soft part of said first endoscope includes a hardness level of said soft part of said second endoscope.

3. An endoscope system according to claim 1, wherein the hardness level of said soft part of said second endoscope is the same as the hardness level of said soft part of said first endoscope which is adjusted to be one of hardest and softest.

4. An endoscope system according to claim 1, wherein the hardness level of said soft part of said second endoscope is intermediate between the hardness level of said soft part of said first endoscope which is adjusted to be hardest and the hardness level of said soft part thereof which is adjusted to be softest.

5. An endoscope system according to claim 1, wherein said second endoscope has a hardness variation mechanism for use in adjusting the hardness level of said soft part, and a range of levels of the adjustable hardness of said soft part of said first endoscope overlaps a range of levels of the hardness of said soft part of said second endoscope having said hardness variation mechanism.

6. An endoscope system according to claim 1, wherein said harness variation mechanism of said first endoscope is composed of an elongated sheath and a wire lying through a bore of said sheath, and said wire is towed in order to relatively compress said sheath and thus adjust the hardness level of said soft part.

7. An endoscope system according to claim 6, wherein said sheath included in said hardness variation mechanism has flexibility in a normal state, and becomes harder when compressed; and when a degree of compression is varied, the hardness of said sheath varies according to the degree of compression.

8. An endoscope system according to claim 6, wherein said sheath is a coil.

9. An endoscope system according to claim 6, wherein said sheath is made by lining up independent ring members in a longitudinal direction.

10. An endoscope system according to claim 6, wherein said wire included in said hardness variation mechanism is formed with a strand.

11. An endoscope system according to claim 10, wherein an end of said wire is fixed to said insertion unit so that said wire cannot be rotated.

12. An endoscope system according to claim 10, wherein an end of said wire selectively slides in a distal direction and proximal direction of said insertion unit and is arranged so that said wire cannot be rotated.

13. An endoscope system according to claim 1, wherein at least an area of said first endoscope in which said hardness variation mechanism lies is softer than a corresponding area of said second endoscope.

14. An endoscope system according to claim 13, wherein an area in which said hardness variation mechanism lies is made of a soft material.

15. An endoscope system according to claim 13, wherein an area in which said hardness variation mechanism lies is designed to have one of a smaller diameter and a smaller thickness than an adjacent area.

16. An endoscope system according to claim 1, wherein the hardness level of said soft part of said first endoscope can be set to a hardness level which is the same as that of said soft part of said second endoscope by adjusting said harness variation mechanism.

17. An endoscope system according to claim 1, wherein distal sides of said soft parts of said first endoscope and second endoscope are softer, and back sides succeeding said distal sides of said soft parts are set to a higher hardness level than that of the distal sides.

18. An endoscope system according to claim 1, wherein a distal end of said hardness variation mechanism is located at a position separated by a given distance from a tip of said first endoscope, and an area whose hardness does not vary is defined in a distal side of said soft part.

19. An endoscope system according to claim 18, wherein said given distance is sufficient to enable said soft part to bend 180°.

20. An endoscope system according to claim 18, wherein said given distance is a distance of less than 40 cm from the tip of said endoscope.

21. An endoscope system according to claim 1, wherein when said soft part of said first endoscope is hardened using said hardness variation mechanism, the hardness of a hardened proximal side of said first soft part being lower than that of a hardened distal side of said first soft part.

22. An endoscope system according to claim 1, wherein when said soft part of said first endoscope is softened using said hardness variation mechanism, a hardness of a proximal side of said first soft part being lower than that of a distal side of said first soft part.

23. An endoscope system according to claim 1, wherein a hardness variation range or a range of levels of a hardness of a proximal side of said soft part of said first endoscope which is varied by said hardness variation mechanism is narrower than a hardness variation range of a distal side thereof.

24. An endoscope system according to claim 1, wherein said second endoscope has a hardness level which is included in a range of levels of adjustable hardness of said soft part of said first endoscope which includes different hardness levels.

25. An endoscope system according to claim 1, wherein the hardness level of a proximal side of said soft part of said first endoscope, which is proximal in a longitudinal direction of said insertion unit of said first endoscope, is higher than a hardness level of a distal side thereof; a distal end of said hardness variation mechanism being located distally to a hardest area of a proximal side of said first soft part; and a hardness of at least part of said first soft part being varied by means of said hardness variation mechanism.

26. An endoscope system according to claim 25, wherein said soft part of said first endoscope is composed of a first soft part that has a given softness and forms a distal side of said first soft part, and a second soft part which communicates with said first soft part and whose hardness level is set to be a little higher than that of said first soft part; the distal end of said hardness variation mechanism being located in one of said first soft part and said second soft part; and the hardness level of said first soft part is varied in multiple steps by means of said hardness variation mechanism.

27. An endoscope system according to claim 26, wherein a hardness variation point at which the hardness level of said soft part of said first endoscope changes and an area of said soft part of which hardness level is varied by means of said hardness variation mechanism are located at different positions.

28. An endoscope system according to claim 25, wherein said hardness variation mechanism is located in the longitudinal direction along an inner wall of said soft part of said first endoscope in one of an up side and down side on a vertical cross section of said first soft part.

29. An endoscope system according to claim 1, wherein when the hardness of said soft part of said first endoscope is set to a highest level using said hardness variation mechanism, an intermediate-hardness area whose hardness is higher than that of a distal side of said first soft part and lower than that of a proximal side thereof is defined between a distal side having a lowest hardness and the proximal side whose hardness is set to a highest level by means of said hardness variation mechanism.

30. An endoscope system according to claim 29, wherein said intermediate-hardness area is defined as a hardness variation area whose hardness level varies continuously along a length thereof.

31. An endoscope system according to claim 29, wherein the hardness level of a proximal side of said soft part of said first endoscope bordered by said intermediate-hardness area increases to a value higher than that of a distal side thereof.

32. An endoscope system according to claim 1, wherein a hardness of a proximal side of a coil included in said hardness variation mechanism, which is proximal in a longitudinal direction of said insertion unit, is set to be higher than that of a distal side thereof, and a hardness level along a length of said soft part of said first endoscope is varied in multiple steps.

33. An endoscope system according to claim 1, wherein the hardness level of said soft part of said first endoscope is varied by adjusting a hardness of a content incorporated in said first soft part.

34. An endoscope system according to claim 1, wherein a forceps channel is incorporated in said insertion unit; and when a stylet extends through said forceps channel, a hard distal part of a stylet body of said stylet is located distally to said distal end of said hardness variation mechanism.

35. An endoscope system according to claim 1 wherein a range of levels of hardness of said soft part of said first endoscope is determined so that when said first soft part is hardened by means of said hardness variation mechanism and said insertion unit is bent to a given minimum radius of curvature, said hardness variation mechanism can be prevented from buckling.

36. An endoscope system according to claim 1, wherein the hardness level of said soft part of said first endoscope that is hardened to a greatest extent is determined so that when said first soft part is hardened by means of said hardness variation mechanism and said insertion unit is bent to a given minimum radius of curvature, other contents of said insertion unit of said endoscope are prevented from buckling.

37. An endoscope system according to claim 35 or 36, wherein an angle, at which said first soft part is bent to a minimum radius of curvature, is 180°.

38. An endoscope system according to claim 6, wherein a positional relationship between said sheath and wire constituting said hardness variation mechanism is adjusted in order to produce a given play, whereby when said soft part of said first endoscope is softened and bent, a softness of said first soft part is maintained.

39. An endoscope system according to claim 38, wherein said play is produced by pushing said wire into said sheath by a given magnitude.

40. An endoscope system according to claim 38, wherein said coil included in said hardness variation mechanism is a close-contact coil; and when said hardness variation mechanism is set to a low level, there is a gap between turns of a wire forming said close-contact coil.

41. An endoscope system according to claim 16, wherein when the hardness level of said first soft part is fixed by means of said hardness variation mechanism, said first endoscope cannot be hung on an endoscope hanger.

42. An endoscope system according to claim 16, wherein when the hardness level of said first soft part is fixed by means of said hardness variation mechanism, said endoscope system cannot be stowed in a stowage case for transportation or storage.

43. An endoscope system according to claim 16, wherein when the hardness level of said first soft part is fixed by means of said hardness variation mechanism, said endoscope cannot be put in one of an endoscope cleaner and a sterilizer.

* * * * *

UNITED STATES PATENT AND TRADEMARK OFFICE
CERTIFICATE OF CORRECTION

PATENT NO : 5,885,208
DATED : March 23, 1999
INVENTOR(S): Hiroki Moriyama

It is certified that error appears in the above-identified patent and that said Letters Patent are hereby corrected as shown below:

At column 8, line 47, insert "," after the word "behind".
At column 8, line 48, insert "," after the word "of".
At column 14, line 44, delete the word "circumferences" and insert therefor --circumstances--.

IN THE CLAIMS

Claim 24, column 46, line 29, insert the word --two-- before "different".
Claim 27, column 46, line 53, insert the word --first-- before the word "soft part".
Claim 28, column 46, line 58, insert the word --first-- before the word "soft part".
Claim 40, column 48, line 18, delete the word "coil" and insert therefor --sheath--.

Signed and Sealed this

Twenty-ninth Day of May, 2001

*Attest:*

NICHOLAS P. GODICI

*Attesting Officer*   Acting Director of the United States Patent and Trademark Office